(12) United States Patent
Tenhaef et al.

(10) Patent No.: US 12,312,608 B2
(45) Date of Patent: May 27, 2025

(54) D-XYLOSE DEHYDROGENASE FROM CORYNEFORM BACTERIA AND PROCESS FOR PREPARING D-XYLONATE

(71) Applicant: Forschungszentrum Juelich GmbH, Juelich (DE)

(72) Inventors: Niklas Tenhaef, Aachen (DE); Stephan Noack, Wegberg (DE); Christian Bruesseler, Krefeld (DE); Jan Marienhagen, Aachen (DE)

(73) Assignee: FORSCHUNGSZENTRUM JUELICH GMBH, Jublich (DE)

( * ) Notice: Subject to any disclaimer, the term of this patent is extended or adjusted under 35 U.S.C. 154(b) by 303 days.

(21) Appl. No.: 17/258,832

(22) PCT Filed: Jun. 29, 2019

(86) PCT No.: PCT/DE2019/000173
§ 371 (c)(1),
(2) Date: Jan. 8, 2021

(87) PCT Pub. No.: WO2020/011294
PCT Pub. Date: Jan. 16, 2020

(65) Prior Publication Data
US 2021/0292716 A1    Sep. 23, 2021

(30) Foreign Application Priority Data
Jul. 11, 2018  (DE) .............. 10 2018 005 439.0

(51) Int. Cl.
*C12P 7/42*    (2006.01)
*C12N 1/20*   (2006.01)
*C12N 9/04*   (2006.01)

(52) U.S. Cl.
CPC ........... *C12N 9/0006* (2013.01); *C12N 1/205* (2021.05); *C12P 7/42* (2013.01); *C12Y 101/01175* (2013.01)

(58) Field of Classification Search
CPC .... C12N 1/205; C12P 7/42; C12Y 101/01175
See application file for complete search history.

(56) References Cited

U.S. PATENT DOCUMENTS

| | | | |
|---|---|---|---|
| 4,489,160 A | 12/1984 | Katsumata et al. | |
| 5,158,891 A | 10/1992 | Takeda et al. | |
| 7,332,310 B2 | 2/2008 | Nakagawa et al. | |
| 10,760,104 B2 | 9/2020 | Noack et al. | |
| 2006/0228712 A1* | 10/2006 | Nakagawa | C12P 13/08 435/6.15 |
| 2012/0005788 A1 | 1/2012 | Richard et al. | |
| 2016/0017376 A1* | 1/2016 | Myeong | C12N 9/0006 435/348 |

FOREIGN PATENT DOCUMENTS

| | | | |
|---|---|---|---|
| CN | 106967159 A | 7/2017 | |
| EP | 1108790 A2 * | 6/2001 | ............. C07K 14/34 |
| EP | 2107128 B1 * | 10/2012 | ............. C07K 14/34 |
| EP | 2902492 A1 | 8/2015 | |
| JP | 2002191370 A | 7/2002 | |
| JP | 2015/029471 A | 2/2015 | |
| WO | WO 9615246 A1 | 5/1996 | |
| WO | WO 2010106230 A1 | 9/2010 | |
| WO | WO 2017220059 A1 | 12/2017 | |

OTHER PUBLICATIONS

Klafft, Simon, et al. "Complex regulation of the phosphoenolpyruvate carboxykinase gene pck and characterization of its GntR-type regulator IolR as a repressor of myo-inositol utilization genes in *Corynebacterium glutamicum*." Journal of bacteriology 195.18 (2013): 4283-4296. (Year: 2013).*

Ikeda, Masato, et al. "Identification and application of a different glucose uptake system that functions as an alternative to the phosphotransferase system in *Corynebacterium glutamicum*." Applied microbiology and biotechnology 90 (2011): 1443-1451. (Year: 2011).*

Myeong HK, et al., "*Corynebacterium glutamicum* CgiolG inositol dehydrogenase, Seq ID:27", EBI accession No. GSP:BBE79706, May 22, 2014 (May 22, 2014), p. 1, GSP: BBE79706, Database accession No. BBE79706. Database Geneseq, Philadelphia, Pennsylvania, USA.

Ando S, et al., "*Corynbacterium glutamicum* ATCC 13032 nucleotide sequence, SEQ ID 184", EBI accession No. GSN: AXS65926, Jan. 7, 2010 (Jan. 7, 2010), p. 1, Database accession No. AXS65923, Database Geneseq, Philadelphia, Pennsylvania, USA.

Sung Sun Yim, et al., "Engineering of *Corynebacterium glutamicum* for Consolidated Conversion of Hemicellulosic Biomass into Xylonic Acid", BioTechnology Journal, Nov. 1, 2017(Nov. 1, 2017), pp. 1-9, vol. 12, No. 11, National Library of Medicine, USA.

Niklas Tenhaef, et al., "Production of d-xylonic acid using a non-recombinant *Corynebacterium glutamicum* strain", Bioresource Technology, Nov. 1, 2018 (Nov. 1, 2018), pp. 332-339, vol. 268, Elsevier, Amsterdam, Netherlands.

Egon Amann, et al., "Tightly regulated tac promoter vectors useful for the expression of unfused and fused proteins in *Escherichia coli*", Gene, Sep. 30, 1988, pp. 301-315, vol. 69, No. 2, Elsevier, Buffalo Grove, Illinois, USA.

Jessica Boyd, et al., "Analysis of the Diphtheria tox Promoter by Site-Directed Mutagenesis", Journal of Bacteriology, Dec. 1988, pp. 5949-5952, vol. 170, No. 12, American Society for Microbiology, USA.

(Continued)

*Primary Examiner* — Robert J Yamasaki
*Assistant Examiner* — Trevor Kane
(74) *Attorney, Agent, or Firm* — LEYDIG, VOIT & MAYER, LTD.

(57) ABSTRACT

A D-xylose dehydrogenase comprising an amino acid sequence that has at least 70% identity to the amino acid sequence according to SEQ ID NO. 2 or fragments thereof.

17 Claims, 30 Drawing Sheets
Specification includes a Sequence Listing.

(56) References Cited

OTHER PUBLICATIONS

Christian Brüsseler, et al., "The myo-inositol/proton symporter IoIT1 contributes to D-xylose uptake in *Corynebacterium glutamicum*", Bioresource Technology, Dec. 2018, vol. 249, Elsevier, Buffalo Grove, Illinois, USA.

J. Buchert, et al., "Production of xylonic acid by pseudomonas fragi", Biotechnology Letters, Aug. 1986, pp. 541-546, vol. 8, No. 8, Springer, Berlin, Germany.

Jae Woong Choi, et al., "Development of a high-copy-number plasmid via adaptive laboratory evolution of *Corynebacterium glutamicum*", Applied Microbiology and Biotechnology, Nov. 25, 2017, pp. 873-883, vol. 102, Springer, Berlin, Germany.

Bernhard J. Eikmanns, et al., "A family of *Corynebacterium glutamicum/ Escherichia coli* shuttle vectors for cloning, controlled gene expression, and promoter probing", Gene, Jun. 15, 1991, pp. 93-98, vol. 102, Elsevier, Buffalo Grove, Illinois, USA.

Daniel G Gibson, et al., "Enzymatic assembly of DANN molecules up to several hundred kilobases", Nature Methods, Apr. 12, 2009, pp. 343-345, vol. 6, No. 5, Springer Nature, Basingstoke, United Kingdom.

H. S. Isbell, et al., "The course of the oxidation of the aldose sugars by bromine water", Bureau of Standards Journal of Research, Jan. 11, 1932, pp. 327-338, vol. 8, Burea of Standards Journal Research, Washington, USA.

Peter Rudal Jensen, et al., "Artificial Promoters for Metabolic Optimization", Biotechnology and Bioengineering, Mar. 26, 2000, pp. 191-195, vol. 58, issue 2-3, Wiley Online Library, USA.

A. Jokic, et al., "Simultaneous electrolytic production of ylitol and xylonic acid from xylose", Journal of Applied Electrochemistry, Apr. 1991, pp. 321-326, vol. 21, Springer Nature Switzerland, Switzerland.

Oliver Kirchner, "Tools for genetic engineering in the amino acid-producing bacterium *Corynebacterium glutamicum*", Journal of Biotechnology, Mar. 11, 2003, pp. 287-299, vol. 104, Elsevier, Amsterdam, Netherlands.

Simon Klaffl, et al., "Complex Regulation of the Phosphoenolpyruvate Carboxykinase Gene pck and Characterization of Ist GntR-Type Regulator IolR as a Repressor of myo-Inositol Utilization Genes in *Corynebacterium glutamicum*", Journal of Bacteriology, Sep. 2013, pp. 4283-4296, vol. 195, No. 18, American Society for Microbiology, USA.

Rolf Knippers, et al., "Molekulare Genetik", Moleculare Genetics, Dec. 2018, pp. 1-29, vol. 11, Georg Thieme Verlag, Stuttgart, Germany.

Huaiwei Liu, et al., "High yield production of D-xylonic acid from D-xylose using engineered *Escherichia coli*", Bioresource Technology, Aug. 22, 2011, pp. 244-248, vol. 115, Elsevier, Amsterdam, Netherlands.

Elke Menkel, et al., "Influence of Increased Aspartate Availability on Lysine Formation by a Recombinant Strain of *Corynebacterium glutamicum* and Utilization of Fumarate", Applied and Environmental Microbiology, Mar. 1989, pp. 684-688, American Society for Microbiology, USA.

Axel Niebisch, et al., "Molecular analysis of the cytochrome $bc_1$-$aa_3$ branch of the *Corynebacterium glitamicum* respiratory chain containing an unusal diheme cytochrome $c_1$", Arch Microbiol, Mar. 10, 2001, pp. 282-294, vol. 175, Springer, Berlin, Germany.

Miroslav Patek, et al., "Promoters from *Corynebacterium glitamicum*: cloning, molecular analysis and search for a consensus motif", Microbiology, Dec. 1996, pp. 1297-1309, vol. 142, National Library of Medicine, USA.

F. Pezzotti, et al., "Enzymatic synthesis of aldonic acids", Carbohydrate Research, Jun. 27, 2006, pp. 2290-2292, vol. 341, Elsevier, Amsterdam, Netherlands.

Dieter J. Reinscheid, et al., "Stable Expression of hom-1-thrB in *Croynebacterium glutamicum* and Ist Effect on the Carbon Flux to Threonine and Related Amino Acids", Applied and Environmental Microbiology, Jan. 1994, pp. 126-132, vol. 60, No. 1, American Society for Mcrobiology, USA.

Andreas Schäfer, et al., "Increased Fertility of *Corynbacterium glutamicum* Recipients in Intergeneric Matings with *Escherichia coli* after Stress Exposure", Applied and Environmental Microbiology, Feb. 1994, pp. 756-759, vol. 60, No. 2, American Society for Microbiology, USA.

Theresa M. Serwold-Davis, et al., "Localization of an origin of replication in *Corynebacterium diphtheriae* broad host range plasmid pNG2 that also functions in *Escherichia coli*", FEMS Microbiology, Jan. 1990, pp. 119-124, vol. 66, Elsevier, Amsterdam, Netherlands.

Hans Sonnen, et al., "Characterization of pGA1, a new plasmid from *Corynebacterium glutamicum* LP-6", Gene, Aug. 22, 1991, pp. 69-74, Elsevier, Amsterdam, Netherlands.

Andreas Tauch, et al., "*Corynebacterium glutamicum* DANN is subjected to methylation-restriction in *Escherichia coli*", FEMS Micrbiology Letters, Sep. 7, 1994, pp. 343-348, Elsevier, Amsterdam, Netherlands.

Mervi H. Toivari, et al., "Microbial D-xylonate production", Appl Microbiol Biotechnol, Aug. 9, 2012, pp. 1-8, vol. 96, Springer, Berlin, Germany.

Pavla Vasicova, et al., "Analysis of the *Corynebacterium glutamicum* dapA Promoter", Journal of Bacteriology, Oct. 1999, pp. 6188-6191, vol. 181, No. 19, American Society for Microbiology, USA.

Martin I. Voskuil, et al., "The-16 region of Bacillus subtilis and other gram-positive bacterial promoters", Nucleic Acids Research, Jun. 5, 1998, pp. 3584-3590, vol. 26, No. 15, Oxford, United Kingdom.

Staff at Pacific Northwest National Library, "Top Value Added Chemicals From Biomass vol. I—Results of Screening for Potential Candidates From Sugars and Synthesis Gas", Energy Efficiency and Renewable Energy Report, Aug. 2004, pp. 1-76, U.S. Department of Energy, Washington D.C., USA.

Ernst-Ludwig Winnacker, "Gene und Klone: Eine Einführung in die Gentechnologie", Gene und Klone, Apr. 1985, p. 68, VCH Verlagsgesellschaft mbH, Weinheim, Germany.

Griess, Eike; "Stringenz"; *Spektrum.de—Lexikon der Biologie*; Dec. 1999; pp. 1-2; [Online] Retrieved from internet: https://www.spektrum.de/lexikon/biologie/stringenz/64302; Spektrum Akademischer Verlag; Heidelberg, Germany.

\* cited by examiner

```
XylB      1 mssalypslkgk----- -------rvvitgggsglgagltagfargga--------------
IolG      1 msksirvgvvgagamgadhidrinnrtsqahissiispdaaraaaaaedapgaqaftrle XylB     37 evifldiadedsraisael--------------agspi---------ppvykrcdlmnlea--ikav
IolG     61 dalaadavdsviiavpggfhepvlvpsleaqlpilcekpltpdsessirivelegkidkp XylB     79 faeiqdv---dvivnn-----agnddrhkladvtgaywderinvnirkmifctqavapgmk
IolG    121 hiqvgfmrrfdpeynnirkivesgeagellmlrglhrnpsvgesytqsallidsvvhefd XylB    132 k-----rgggavinfg---------siswhiqied---iviyetakaqleqmtrsisrelgpddir
IolG    181 vipwlagarvvsvevkypktsalahsglkspllvimelengvivdvemmvnlqfgyqvat XylB    181 vtcvvpgnvkktkr-------qskwytpegeaqivasqclkgrivpenvaalvifi-asudaalc
IolG    241 eavfekglarigmpegmqrv---rdgeflinehtdfttrfataydrqiqswvdavhegtlv XylB    237 tgheyw----------------idagwr----------
IolG    299 agpnswdgylvalaceagvksldggvipvdasprpdfya
```

FIG. 3

```
iolT1 WT    1 accttgattgatcatgtcgaggaaagccgtacggctttcctctggattg
PO6iolT1    1 ..................................................

iolT1 WT   51 ttctacgaatgcccacttcgcacccttggggttgctcgtggtgcattcac
PO6iolT1   51 ..................................................

iolT1 WT  101 ccctgaaccgcctagggtttgatgcaaaattcgttcgactttatggc
PO6iolT1  101 ..................................................

iolT1 WT  151 cagacctcacgctgtggtgaaaaattgatcagcaacaccaggtttca
PO6iolT1  151 ..................................................

iolT1 WT  201 cattcgcccaccagtcccaaaatgatgacgttccagagcgccgctgac
PO6iolT1  201 ..................................................

iolT1 WT  251 ggcaatttgtgcccactttgacacaagtggtcgatcacgtctcgagccg
PO6iolT1  251 ..................................................

iolT1 WT  301 cttaaacgggcgattatcgcccaccattccgatgtccgctcctcgcac
PO6iolT1  301 ..................................................

iolT1 WT  351 gcttttgtaatgacattaggatctttaagcagtgaatgaggtgacaatg
PO6iolT1  351 ..................................................

iolT1 WT  401 tcacctaacaaggtgtcaaacagccccaatcactaccccctccacccc
PO6iolT1  401 ..................................................

iolT1 WT  451 gcacccttatccagaaactcccatgctccaacattccagaggggcagt
PO6iolT1  451 ..................................................

iolT1 WT  501 ttctgacattaccacataactcctgcatcaaaccgcagctacagccac
PO6iolT1  501 ..................................................

iolT1 WT  551 accctgctgaaaatcccgaatggaaaaccataccaagcagacaccccc
PO6iolT1  551 ..................................................

iolT1 WT  601 accctaagtattaccaattactcaaaagtattcaaaaaagtttgttat
PO6iolT1  601 ..................................................
                                 -35              -10
iolT1 WT  651 gtacgattgacgggacatatcgtgtctgccacgattaaagacattggtga
PO6iolT1  651 ...............gg.................................
```

FIG. 3 (cont'd)

```
iolT1 WT    701  tgtgaatcactgcctactacatcgtgtttcgtgaccctgcacctccaagt
PO6iolT1    701  ..................................................
                                             iolT1
iolT1 WT    751  aagggcacgacaaacttaggagacaagatggctagtaccttcattcaggc
PO6iolT1    751  ..................................................

iolT1 WT    801  cgacagccctgaaaaaagtaagaagctgcccccactcacagaaggtccgt
PO6iolT1    801  ..................................................

iolT1 WT    851  atagaaagcggctattctacgttgcactagttgcgacgtttggtgggctg
PO6iolT1    851  ..................................................

iolT1 WT    901  ctcttcggatatgacaccggagtaatcaacggtgcactcaaccccaatgac
PO6iolT1    901  ..................................................

iolT1 WT    951  acgtgagctcggactaaccgagttcaccgagggtgttgtaacttcttccc
PO6iolT1    951  ..................................................

iolT1 WT   1001  tgctgtttggtgcagcagctggtgcgatgttttcggtcgcatttccgac
PO6iolT1   1001  ..................................................

iolT1 WT   1051  aactggggtcgccggaaaacaatcatctcacttgcagtagcttctttgt
PO6iolT1   1051  ..................................................

iolT1 WT   1101  cggcaccatgatctgcgtgtttgctccatcttttgcagtaatggttgtcg
PO6iolT1   1101  ..................................................

iolT1 WT   1151  gacgtgtgcttcttggactcgcagttggtggcgcttccactgttgtccct
PO6iolT1   1151  ..................................................

iolT1 WT   1201  gtctacctggctgaacttgctccttttgaaatccgtggctcactggctgg
PO6iolT1   1201  ..................................................

iolT1 WT   1251  ccgtaatgagttgatgattgttgttggtcagctcgcagcttttgtcatca
PO6iolT1   1251  ..................................................

iolT1 WT   1301  atgcgattattggaaatgttttttggacaccacgatggtgtgtggcgctac
PO6iolT1   1301  ..................................................

iolT1 WT   1351  atgctggcaattgccgcaatcccagcaattgccctcttctttggaatgct
PO6iolT1   1351  ..................................................

iolT1 WT   1401  ccgagttccagaatccccacgctggcttgttgagcgaggacgcattgatg
PO6iolT1   1401  ..................................................

iolT1 WT   1451  aggctcgcgcagttcttgaaaccattcgccctctagaacgtgcccatgca
PO6iolT1   1451  ..................................................
```

FIG. 3 (cont'd)

```
iolT1 WT   1501 gaagttgctgatgttgaacacctagcaagagaagagcacgccgtttccga
PO6iolT1   1501 ..................................................

iolT1 WT   1551 gaagtccatgggcttaagggaaattttgtccagcaagtggcttgtgcgca
PO6iolT1   1551 ..................................................

iolT1 WT   1601 tcctcctggtaggtatcggattgggtgtcgcacagcagctgacggcatc
PO6iolT1   1601 ..................................................

iolT1 WT   1651 aactccatcatgtactacggccaggttgttctcattgaggctggttttctc
PO6iolT1   1651 ..................................................

iolT1 WT   1701 cgagaatgcagctctgatcgccaacgtggcgccaggagtgatcgcagttg
PO6iolT1   1701 ..................................................

iolT1 WT   1751 tcggtgcattcatcgcactgtggatgatggatcgtatcaaccgccgtacc
PO6iolT1   1751 ..................................................

iolT1 WT   1801 accctcattaccggttattctctcaccaccattagccacgtattgatcgg
PO6iolT1   1801 ..................................................

iolT1 WT   1851 tatcgcatccgtagcattcccagtcggcgatcctcttcgcccctacgtta
PO6iolT1   1851 ..................................................

iolT1 WT   1901 tcttgactctggttgtggtcttcgtgggatccatgcagaccttcctcaac
PO6iolT1   1901 ..................................................

iolT1 WT   1951 gtagctacctgggttatgctctctgagctcttcccgctggcaatgcgcgg
PO6iolT1   1951 ..................................................

iolT1 WT   2001 tttcgcaatcggtatctcagtgttcttcctctggatcgcaaacgcgttcc
PO6iolT1   2001 ..................................................

iolT1 WT   2051 tcggattgttcttcccaaccatcatggaagcagtaggactaacggaacc
PO6iolT1   2051 ..................................................

iolT1 WT   2101 ttcttcatgttcgccggaatcggtgtggttgccttgatcttcatctacac
PO6iolT1   2101 ..................................................

iolT1 WT   2151 ccaggttcctgaaactcgtggacgtaccttggaggagattgatgaggatg
PO6iolT1   2151 ..................................................

iolT1 WT   2201 ttacttccaggtgtcattttcaacaaggacatccgaaaaggaaaggtgcac
PO6iolT1   2201 ..................................................

iolT1 WT   2251 taa
PO6iolT1   2251 ...
```

FIG. 5

```
IolC WT    1    gatgtctccttcgttgccacccaacaagctcatgtaaatgtgttaggacatttgaaca
PO13 iolC  1    ............................................................

IolC WT    61   atgtaactgagttgcgggtggtggtcttggtaaatccgtgttcatgcaggacttttgtgt
PO13 iolC  61   ............................................................

IolC WT    121  catccagggcttttattgatctgacattatcacttgcattagggaatgagtagcgaaact
PO13 iolC  121  ............................................................

IolC WT    181  tagtgaaagggcagagtttgcaggtcataacgtgcaacttgttaacccgcaccttcc
PO13 iolC  181  ............................................................
                                                                    -35
IolC WT    241  aaagcgaggggttttcgtcgacaagcaaaatctttgaatgaaaacggggcgttgcct
PO13 iolC  241  ............................................................

IolC WT    301  ggggttttgcgcgttttcgggaatcgttttagaaaatttcggaatgtattgcttgtc
PO13 iolC  301  ............................................................
                         -10                      TSS
IolC WT    361  aggacaatgtgttattgtcatgacatgcgatcgtgagggtcgccacattccatcaaaat
PO13 iolC  361  ........................gg.................................

IolC WT    421  gagtgaagggttgcatcgccacatgactaacttgacgagcactcacgaagtcctagctat
PO13 iolC  421  ............................................................

IolC WT    481  cggccgcttggcgtagatatttaccccacttcaaagtggagtaggactggcgatgttca
PO13 iolC  481  ............................................................

IolC WT    541  atctttcggcaagtacctcggcggaagcgcagcaaacgtttctgttgcagccgccgca
PO13 iolC  541  ............................................................

IolC WT    601  tggacacaattccgcactgctgtccgtgtgggaaatgatcctttcggcgagtacctgct
PO13 iolC  601  ............................................................

IolC WT    661  tgctgagctggagcgtttgggcgtggacaaccagtacgttgccaccgatcagactttta
PO13 iolC  661  ............................................................

IolC WT    721  gaccccagtgaccttctgtgaaatttccaccggatgatttccactgtactctaccg
PO13 iolC  721  ............................................................

IolC WT    781  cgaaccaaaggctccggatctcaatattgaatccgcagacgtcagcctggacgatgtgcg
PO13 iolC  781  ............................................................

IolC WT    841  cgaagccgatattttgtggttcacactcactggtttcagtgaagagccaagccgcggcac
PO13 iolC  841  ............................................................
```

FIG. 5 (cont'd)

```
IolC WT     901  acaccgcgagatcttgactactcgtgcgaaccgtcgccacaccatctttgatctggacta
PO13 iolC   901  ............................................................

IolC WT     961  ccgaccaatgttctgggaatccccagaagaggccaccaagcaggcggaatgggcgttgca
PO13 iolC   961  ............................................................

IolC WT    1021  gcattccacggtggcggttggcaacaaggaagaatgcgaaatcgcagtggcgagaccga
PO13 iolC  1021  ............................................................

IolC WT    1081  gccagagcgcgcgggccgagcactgttggaacgcggtgtggagttggccatcgtcaagca
PO13 iolC  1081  ............................................................

IolC WT    1141  gggacctaagggtgtcatggcgatgaccaaggacgaaaccgtagaagttcctccgttctt
PO13 iolC  1141  ............................................................

IolC WT    1201  cgtcgatgtcatcaacggtcttggtgccggcgatgcattcggcggcgcgctgtgccacgg
PO13 iolC  1201  ............................................................

IolC WT    1261  tctgctctctgaatggccgttggaaaaggttctccgttttgccaacaccgcgggtgcgct
PO13 iolC  1261  ............................................................

IolC WT    1321  tgtggcgtcccgtcttgaatgctccaccgcaatgcctactaccgatgaggtggaagcctc
PO13 iolC  1321  ............................................................

IolC WT    1381  cctcaaccagaaagtctga
PO13 iolC  1381  ...................
```

FIG. 7

```
iolC WT    1     gatgtctccttttcgttgccaccaacaagctcatgtaaatgtgttaggacatttgaaca
PO5-O9 iolC 1    ............................................................

iolC WT    61    atgtaactgagttgcgggtggtggtcttggtaaatccgtgttcatgcaggactttgtgt
PO5-O9 iolC 61   ............................................................

iolC WT    121   catccagggcttttattgatctgacattatccacttgcattagggaatgagtagcgaact
PO5-O9 iolC 121  .............................gg............................

iolC WT    181   tagtgaaaagggcagagtttgcaggtcataacgtgcaactttgttaacccgcaccttcc
PO5-O9 iolC 181  .............................gg............................
                                             -35
iolC WT    241   aaagcgaggggggtttttcgtcgacaagcaaatctttgaatgaaaccggggcgttgcct
PO5-O9 iolC 241  ............................................................

iolC WT    301   ggggttttgcgcgttttcgggaatcgtttagaaatttttcggaaatgtattgcttgtc
PO5-O9 iolC 301  ............................................................
                          -10                  TSS
iolC WT    361   aggacaatgtgttattgtcatgacatgcgatcgtgagggtcgccacattccatcaaaaat
PO5-O9 iolC 361  ............................................................

iolC WT    421   gagtgaagggttgcatcgccacatgactaacttgacgagcactcacgaagtcctagctat
PO5-O9 iolC 421  ............................................................

iolC WT    481   cggccgcttggtcgtagatatttaccoacttcaaagtggagtaggactggccgatgttca
PO5-O9 iolC 481  ............................................................

iolC WT    541   atctttcggcaagtacctcggcggaagcgcagcaaacgtttctgttgcagccgccgcca
PO5-O9 iolC 541  ............................................................

iolC WT    601   tggacaccattccgcactgctgtcccgtgtgggaaatgatcctttcggcgagtacctgct
PO5-O9 iolC 601  ............................................................

iolC WT    661   tgctgagctggagcgtttgggcgtggacaaccagtacgttgccaccgatcagactttaa
PO5-O9 iolC 661  ............................................................

iolC WT    721   gacccagtgaccttctgtgaaattttccacggatgatttcccactgtacttctaccg
PO5-O9 iolC 721  ............................................................

iolC WT    781   cgaaccaaaggctccggatctcaatattgaatccgcagacgtcagcctggacgatgtgcg
PO5-O9 iolC 781  ............................................................

iolC WT    841   cgaagccgatattttgtggttcacactcactggtttcagtgaagagccaagccgcggcac
PO5-O9 iolC 841  ............................................................

iolC WT    901   acaccgcgagatcttgactactcgtgcgaaccgtcgccacaccatctttgatctggacta
PO5-O9 iolC 901  ............................................................

iolC WT    961   ccgaccaatgttctgggaatcccagaagaggccaccaagcaggcggaatgggcgttgca
PO5-O9 iolC 961  ............................................................
```

FIG. 7 (cont'd)

```
iolC WT     1021   gcattccacggtggcggttggcaacaaggaagaatgcgaaatcgcagtgggcgagaccga
P05-09 iolC 1021   ............................................................

iolC WT     1081   gccagagcgcgcgggccgagcactgttggaacgcggtgtggagttggccatcgtcaagca
P05-09 iolC 1081   ............................................................

iolC WT     1141   gggacctaagggtgtcatggcgatgaccaaggacgaaaccgtagaagttcctccgttctt
P05-09 iolC 1141   ............................................................

iolC WT     1201   cgtcgatgtcatcaacggtcttggtgccggcgatgcattcggcggcgcgctgtgccacgg
P05-09 iolC 1201   ............................................................

iolC WT     1261   tctgctctctgaatggccgttggaaaaggttctccgttttgccaacaccgcgggtgcgct
P05-09 iolC 1261   ............................................................

iolC WT     1321   tgtggcgtccgtcttgaatgctccaccgcaatgcctactaccgatgaggtggaagcctc
P05-09 iolC 1321   ............................................................

iolC WT     1381   cctcaaccagaaagtctga
P05-09 iolC 1381   ...................
```

D-XYLOSE DEHYDROGENASE FROM CORYNEFORM BACTERIA AND PROCESS FOR PREPARING D-XYLONATE

CROSS REFERENCE TO PRIOR APPLICATIONS

This application is a U.S. National Phase application under 35 U.S.C. § 371 of International Application No. PCT/DE2019/000173, filed on Jun. 29, 2019, and claims benefit to German Patent Application No. 10 2018 005 439.0, filed on Jul. 11, 2018. The International Application was published in German on Jan. 16, 2020 as WO 2020/011294 A1 under PCT Article 21(2).

FIELD

The present invention relates to D-xylose dehydrogenase from coryneform bacteria, nucleic acid sequences encoding same, corresponding living organisms, preferably coryneform bacteria, which contain a D-xylose dehydrogenase with enhanced D-xylose dehydrogenase expression and/or activity, and corresponding uses. The present invention also relates to a process for preparing D-xylonate with D-xylose dehydrogenase from coryneform bacteria.

BACKGROUND

D-xylonic acid ($C_5H_{10}O_6$) is an organic acid which can serve as a precursor for polyamides, polyesters, and 1,2,4-butanetriol (Toivari et al. 2012; https://doi.org/10.1007/s00253-012-4288-5) and thus has a broad application potential in the pharmaceutical industry, the food industry, and in the chemical industry.

D-xylonate, the salt of D-xylonic acid, ranks among the top 30 potentially high-grade platform chemicals based on renewable second-generation raw materials (Werpy et al. 2004; http://www.dtic.mil/dtic/tr/fulltext/u2/a436528.pdf). D-xylonate has the potential to replace D-gluconate ($C_6H_{11}O_7$), which has a global market of 100 kt/year.

D-xylonate is naturally formed in some bacteria via a two-step reaction. In the first reaction, D-xylose is oxidized to D-xylonolactone, wherein specific dehydrogenases are catalytically active depending on the organism. The D-xylonolactone can subsequently be converted to D-xylonate either by specific lactonases or spontaneously (without an enzyme catalyst). For example, high product titers of D-xylonate are reported for the *Gluconobacter oxydans* and *Pseudomonas fragi* species (Toivari et al., 2012; https://doi.org/10.1007/s00253-012-4288-5; Buchert et al. 1988, http://doi.org/10.1007/BF01028079).

In addition, alternative D-xylonate production strains (e.g., yeast of the species *Saccharomyces cerevisiae*, bacteria of the species *Escherichia coli* and fungi of the species *Aspergillus niger*) were produced by heterologous expression of D-xylose dehydrogenases, e.g., from *Caulobacter crescentus* (Toivari et al., 2012 https://doi.org/10.1007/s00253-012-4288-5; Liu et al. 2012; https://doi.Org/10.1016/j.biortech.2011.08.065; US patent 2012/0005788 A1).

In addition to microbial production, D-xylonate can be prepared electrochemically (Jokic et al. 1991; https://doi.org/10.1007/BF01020216), enzymatically (Pezzotti & Therisod 2006; https://doi.org/10.1016/j.carres.2006.05.023), or by chemical oxidation (Isbell & Hudson 1932; Isbell H S, Hudson C S (1932) The course of the oxidation of the aldose sugars by bromine water. Bur Standards J Res 8:327-338; https://archive.org/details/courseofoxidatio83327isbe).

It is known that D-xylonate can be prepared by fermenting strains of coryneform bacteria, in particular *Corynebacterium glutamicum* (Yim et al. 2017; https://doi.org/10.1002/biot.201700040, Choi et al. 2018; https://doi.org/10.1007/s00253-017-8653-2). The oxidation of D-xylose to D-xylonate is mediated here by heterologous expression of the xylose dehydrogenase of *Caulobacter crescentus*. However, the expression of heterologous systems is disadvantageous and undesirable with a view to application in the pharmaceutical or food industry. This is because all hitherto known production strains with a D-xylonate synthesis capacity, such as *Gluconobacter oxydans*, require complex media for their growth, as a result of which the cultivation becomes markedly more complex, more expensive, and thus more uneconomical.

In investigations to optimize the substrate during the microbial production of amino acids (e.g., L-lysine and L-glutamate) and other precursors of industrial biotechnology with coryneform bacteria, the ability to take up naturally non-metabolized substrates, such as D-xylose, was investigated. The myo-inositol/proton symporter (IolT1) could be shown to contribute to the uptake of D-xylose in *Corynebacterium glutamicum* (Brusseler et al., 2018; https://doi.org/10.1016/j.biortech.2017.10.098). However, the D-xylose of coryneform bacteria is not naturally metabolized and thus accumulates in the medium.

WO 2017/220059 A1 discloses that the inactivation or deletion of the iolR gene encoding the regulator protein IolR on a defined medium with D-glucose and D-xylose as carbon and energy sources brings about the formation of D-xylonate.

Klaffl et al. describe gene cg0196 encoding the regulator IolR in the context of the production of the amino acid L-lysine (2013; https://doi.org/10.1128/JB.00265-13). The deletion of iolR leads to the expression of the myo-inositol gene cluster as well as a further estimated 22 genes with previously unknown or unambiguously annotated function (Klaffl et al., 2013). Negative physiological effects resulting from the deregulation of these approx. 22 genes cannot be ruled out. Thus, a bacterial strain on its own with such an iolR deletion does not represent a viable platform for an industrially interesting production strain, which should be genetically unambiguously defined.

SUMMARY

In an embodiment, the present invention provides a D-xylose dehydrogenase comprising an amino acid sequence that has at least 70% identity to the amino acid sequence according to SEQ ID NO. 2 or fragments thereof. Nucleic acid sequences encoding the same, microbial cells containing such nucleic acid sequences, and processes for preparing D-xylonate are also provided.

BRIEF DESCRIPTION OF THE DRAWINGS

Figure 1A:
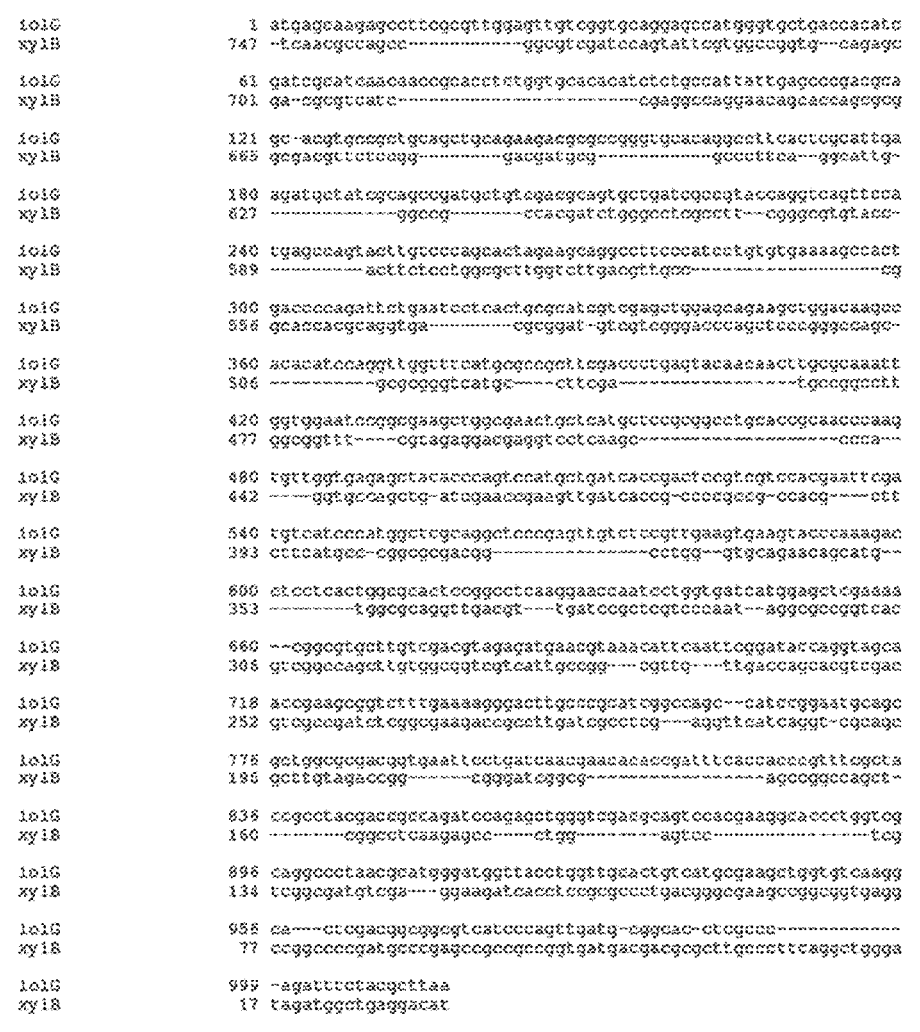

FIG. 1 shows a homology comparison of the amino acid sequences (FIG. 1b) and nucleic acid sequences (FIG. 1a) encoding one of the inventive D-xylose dehydrogenases (IolG) from *Corynebacterium glutamicum* and the D-xylose dehydrogenase (XylB) *Caulobacter crescentus*.

FIG. 3 shows the position of the nucleotide substitutions according to the invention in the regulatory binding site of the myo-inositol transporter gene iolT1 as compared to the wild type. A nucleotide was respectively exchanged relative to the start codon of IolT1 at positions −112 (C→G) and −113 (A→G). This corresponds to positions 665 and 666 in the total sequence of the iolT1 gene according to certain embodiments of the invention of FIG. 3, in which nucleotides AC were substituted for GG. This substitution is between the −35 and −10 box of the iolT1 gene.

FIG. 5 shows the position of the nucleotide substitutions according to certain embodiments of the invention in the regulatory binding site of the iolC gene as compared to the wild type. This regulatory region (upstream of iolC) represents the operatively linked regulatory region of the nucleic acid sequence according to certain embodiments of the invention encoding the D-xylose dehydrogenase according to certain embodiments of the invention since the iolG gene is organized in a cluster, the so-called iolC cluster of myo-insitol catabolism. A nucleotide was respectively exchanged relative to the start codon of IolC at positions −59 (C→G) and −60 (A→G). This corresponds to positions 383 and 384 in the total sequence of the iolC gene of FIG. 5 according to certain embodiments of the invention, in which nucleotides AC were substituted for GG. This substitution is between the −10 box and the transcription start site (TSS) of the iolC gene.

FIG. 7 shows the position of the nucleotide substitutions according to certain embodiments of the invention in the regulatory binding site of the iolC gene compared to the wild type. This regulatory region (upstream of iolC) represents the operatively linked regulatory region of the nucleic acid sequence according to certain embodiments of the invention encoding the D-xylose dehydrogenase according to certain embodiments of the invention since the iolG gene is organized in a cluster, the so-called iolC cluster of myo-insitol catabolism. A nucleotide was respectively exchanged relative to the start codon of IolC at positions −240 (A→G), −239 (C→G), −174 (A→G), and −173 (C→G). This corresponds to positions 143, 144, 211, and 212 in the total sequence of the iolC gene according to certain embodiments of the invention of FIG. 7, in which the nucleotides AC were respectively substituted for GG. This substitution is located 5' upstream of the −10 box and the transcription start site (TSS) of the iolC gene.

DETAILED DESCRIPTION

Figure 2:
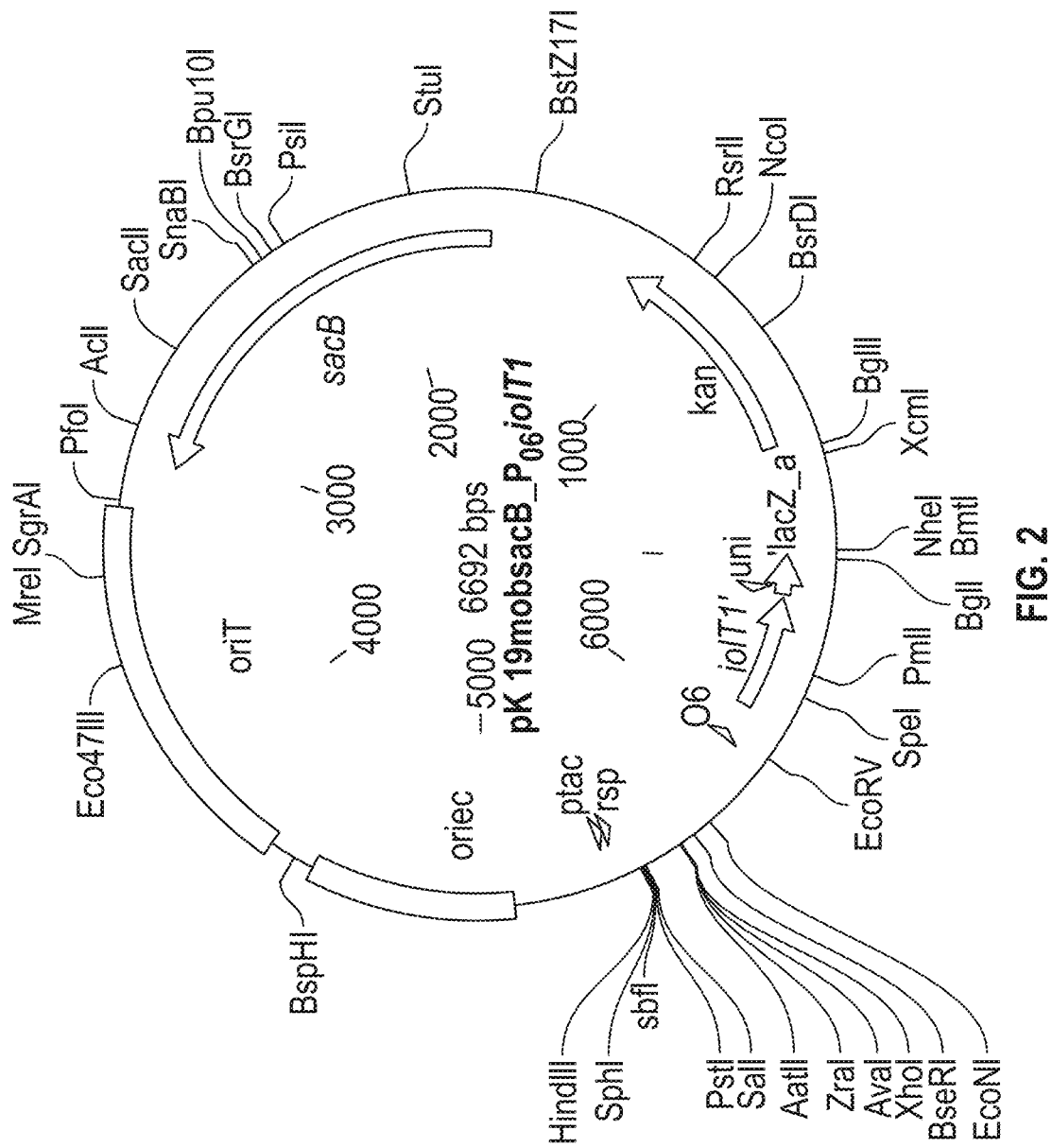
FIG. 2 shows the plasmid pk19mobsacB $P_{O5}$iolT/with which nucleotide substitutions according to the invention were generated in the operatively linked regulatory binding region of the myo-inositol transporter gene iolT1 in the chromosome of *Corynebacterium glutamicum*.
Figure 4:
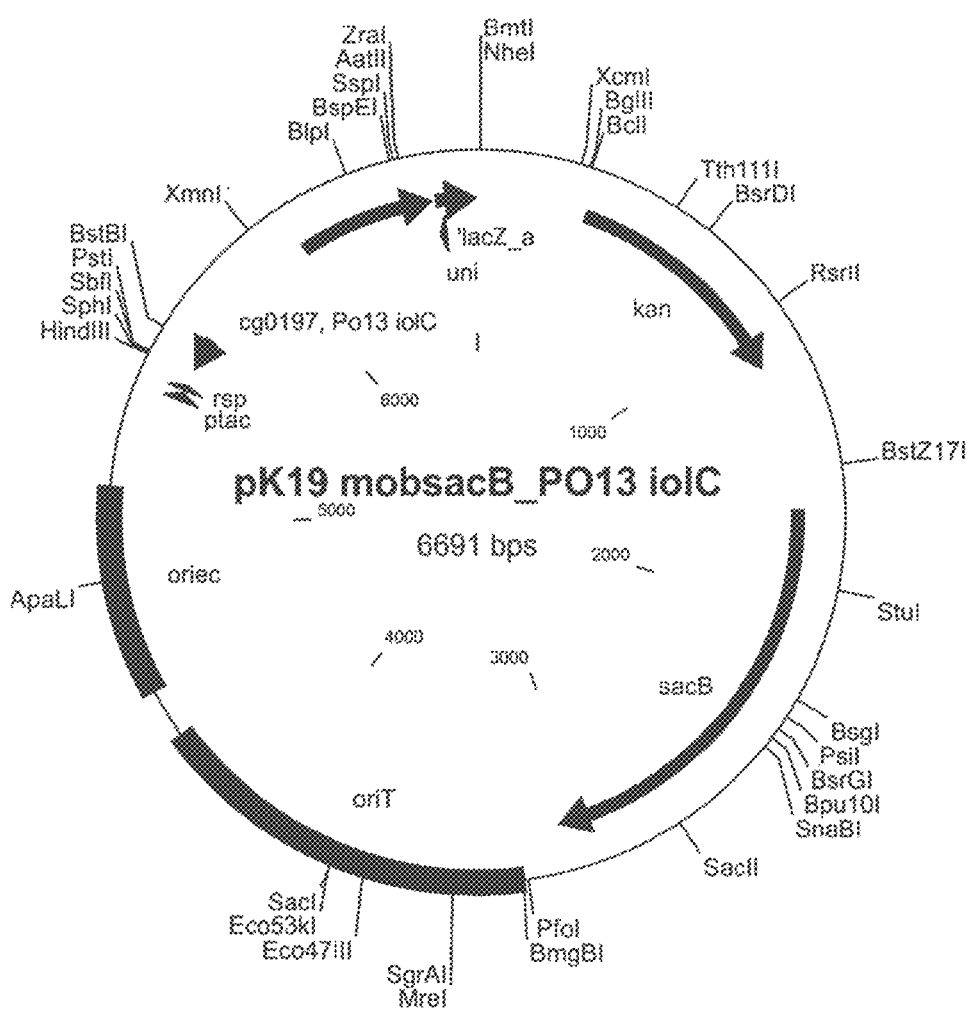
FIG. 4 shows the plasmid pk19mobsacB $P_{O13}$iolC with which nucleotide substitutions according to certain embodiments of the invention were generated in the operatively linked regulatory binding region of the carbohydrate kinase gene iolC (of the iolC cluster containing iolG) in the chromosome of *Corynebacterium glutamicum*.
Figure 6:
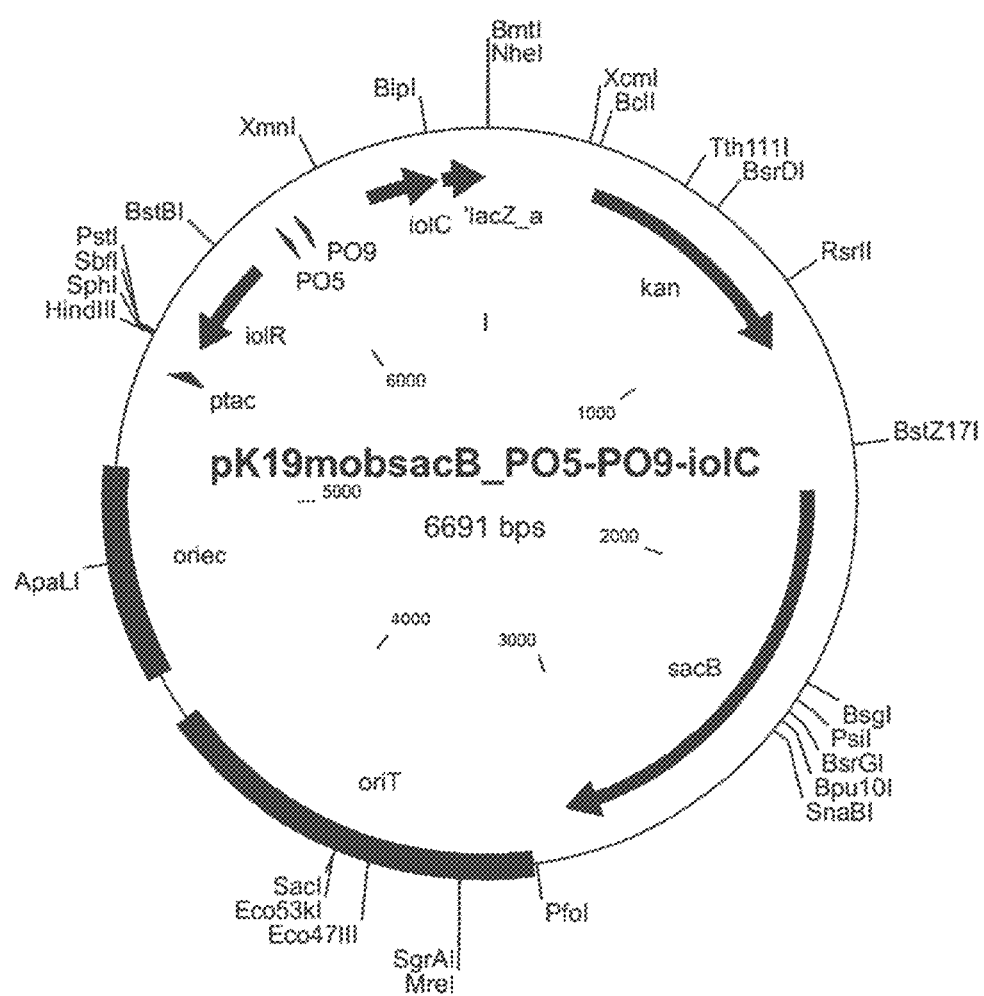
FIG. 6 shows the plasmid pk19mobsacB $P_{O5-O9}$iolC with which nucleotide substitutions according to certain embodiments of the invention were generated in the operatively linked regulatory binding region of the carbohydrate kinase gene iolC (of the iolC cluster containing iolG) in the chromosome of *Corynebacterium glutamicum*.
Figure 8:
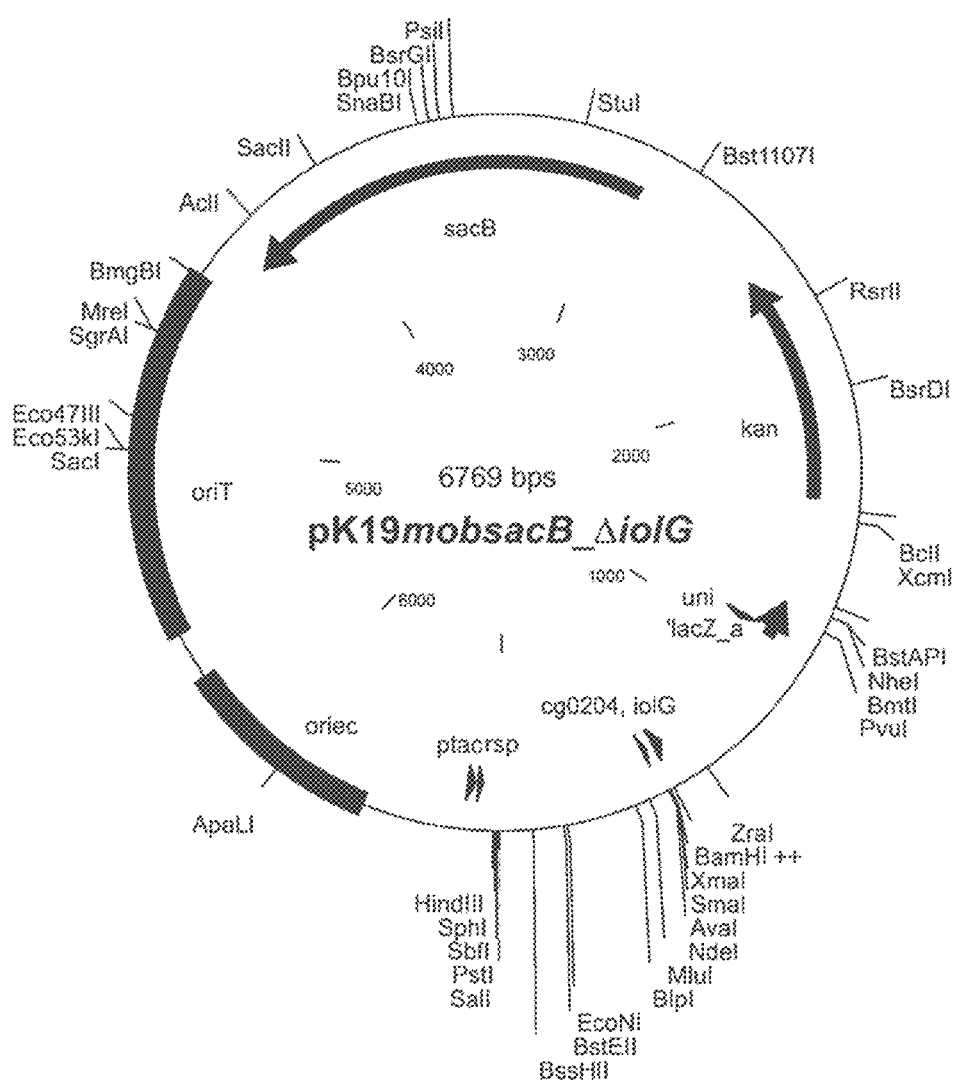
FIG. 8 shows plasmid pk19mobsacB_Δ iolG with which the nucleic acid sequence iolG encoding the D-xylose dehydrogenase according to certain embodiments of the invention was deleted in the chromosome of *Corynebacterium glutamicum*.
Figure 9:
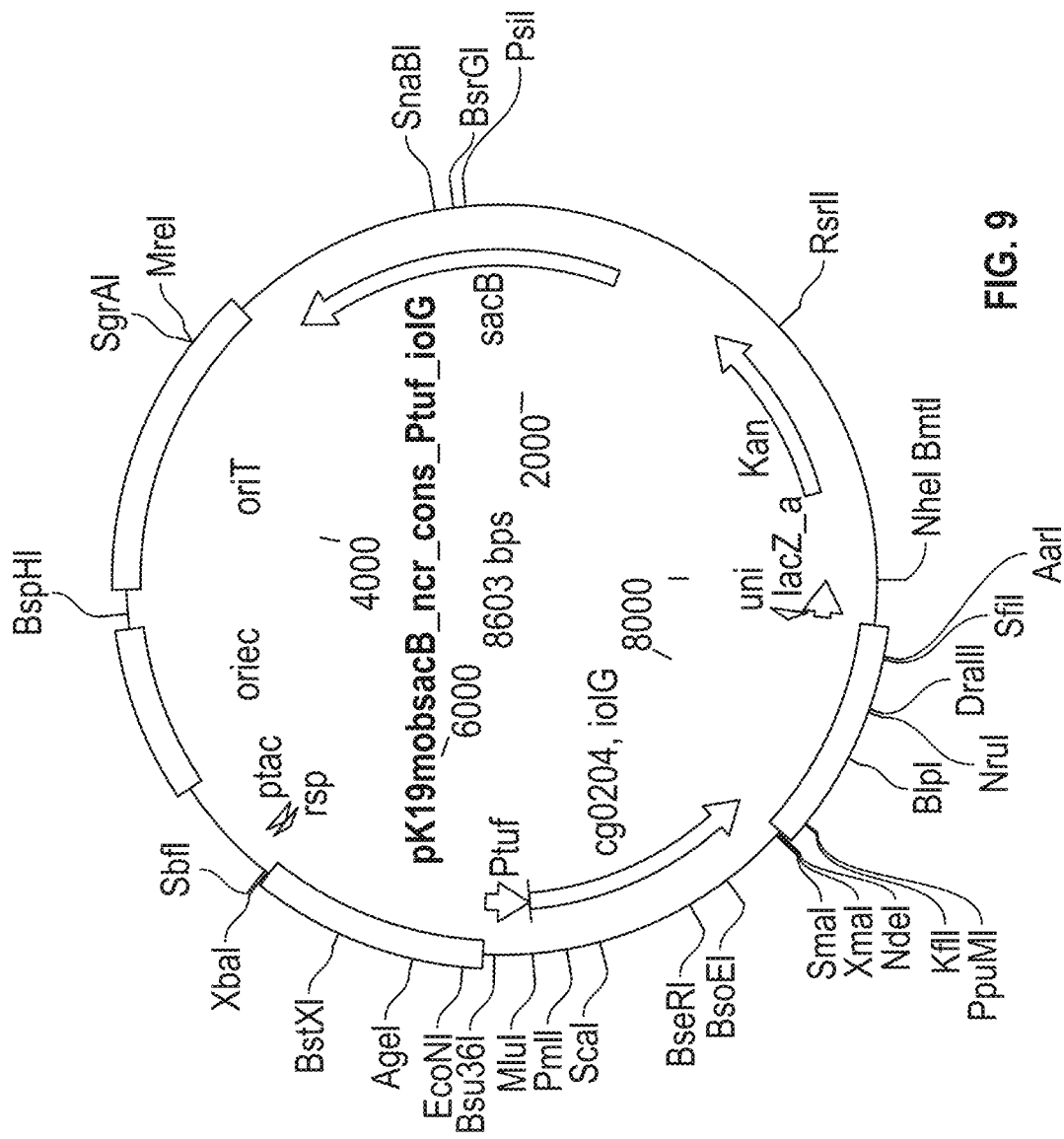
FIG. 9 shows the plasmid pk19mobsacB ncr cons Ptuf iolG with which the nucleic acid sequence iolG encoding the D-xylose dehydrogenase according to certain embodiments of the invention was integrated into the chromosome of *Corynebacterium glutamicum* under the control of the constitutive Tuf promoter in the intergenic region between cg1121 and cg1122.
Figure 10:
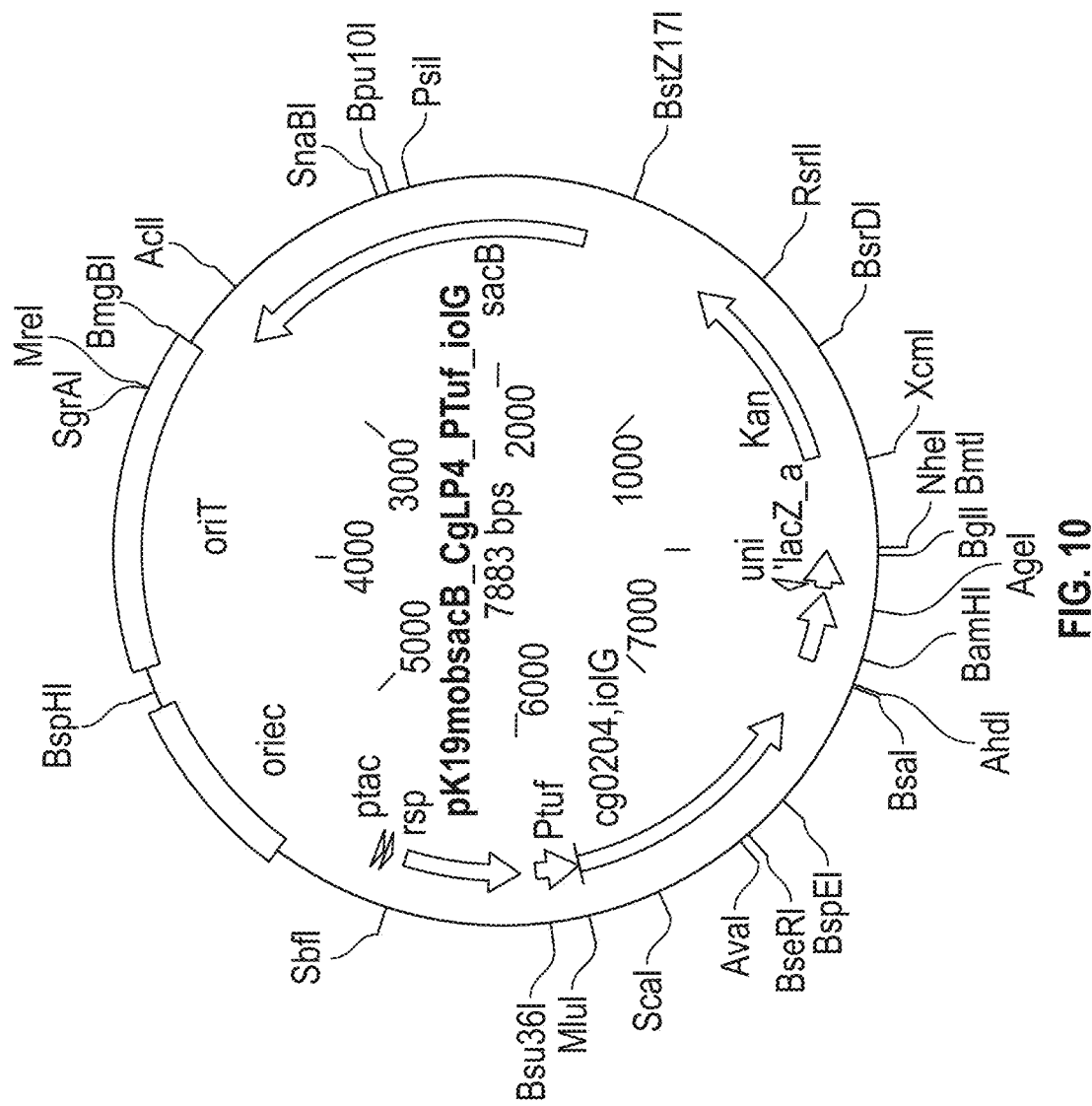
FIG. 10 shows the plasmid pk19mobsacB CgLP4 $P_{Tuf}$iolG with which the nucleic acid sequence iolG encoding the D-xylose dehydrogenase according to certain embodiments of the invention was integrated into the chromosome of *Corynebacterium glutamicum* under the control of the constitutive Tuf promoter in the intergenic region between cg0901 and cg0902.
Figure 11:
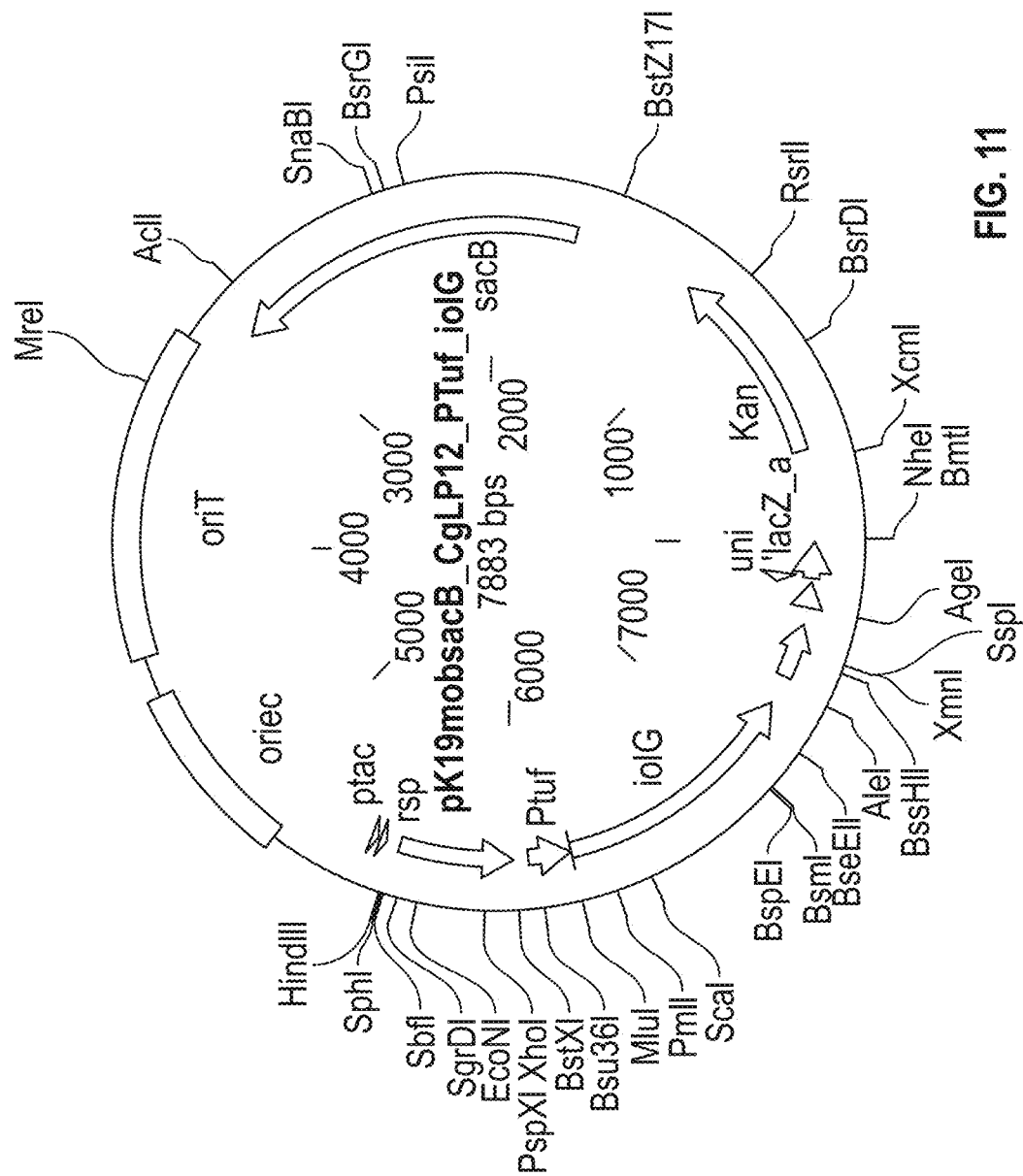
FIG. 11 shows the plasmid pk19mobsacB CgLP12 $P_{Tuf}$ iolG with which the nucleic acid sequence iolG encoding the D-xylose dehydrogenase according to certain embodiments of the invention was integrated into the chromosome of *Corynebacterium glutamicum* under the control of the constitutive Tuf promoter in the intergenic region between cg3227 and cg3228.
Figure 12:
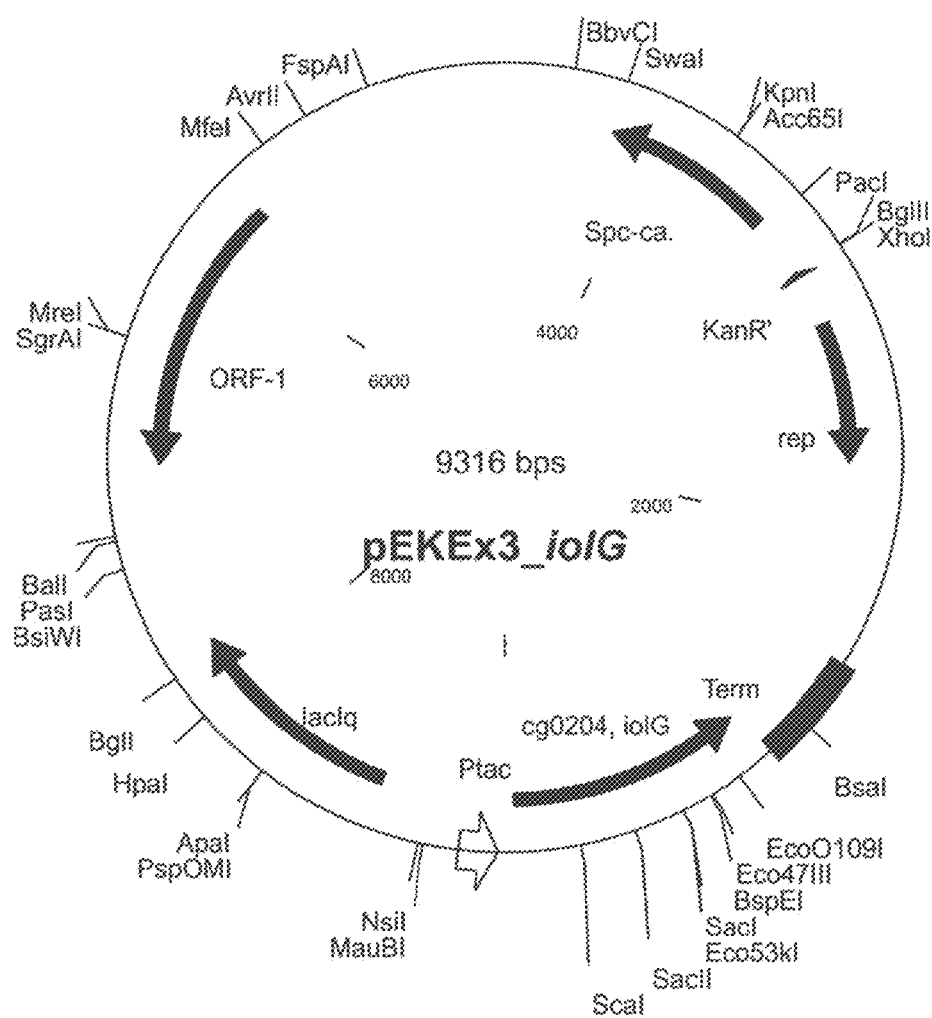
FIG. 12 shows plasmid pEKEx3 iolG with the nucleic acid sequence iolG encoding the D-xylose dehydrogenase according to certain embodiments of the invention was enhancedly expressed in *Corynebacterium glutamicum*.
Figure 13:
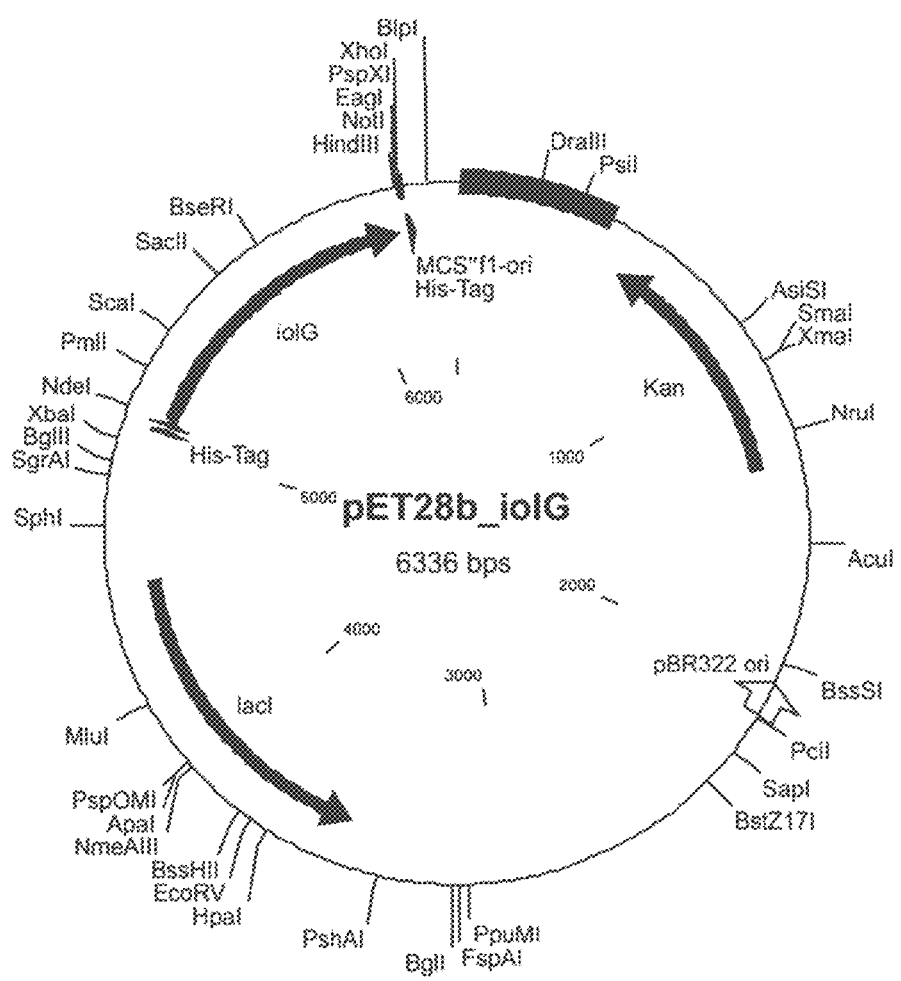
FIG. 13 shows plasmid pET28b iolG with which the nucleic acid sequence iolG encoding the D-xylose dehydrogenase according to certain embodiments of the invention was enhancedly expressed in *Escherichia coli* BL21.

Embodiments of the invention are independent of or avoid a heterologous gene expression for the microbial preparation of D-xylonate in coryneform bacteria. Furthermore, embodiments avoid such interference in the metabolism of coryneform bacteria which may have widely undefined physiological effects, as is the case, for example, when one or more centrally acting regulators (such as the regulator protein IolR), which exert influence on a multiplicity of genes or proteins in a cell, are turned off. Thus, embodiments of the present invention provide a homologous system and one or more homologous structural elements that enable the microbial preparation of D-xylonate with coryneform bacteria while overcoming known disadvantages. Embodiments of the present invention to provide a process for the microbial preparation of D-xylonate in coryneform bacteria, in which the known disadvantages are overcome.

There first follows a brief description of the present invention, without the subject matter of the invention being limited thereby.

An embodiment of the present invention relates to the provision of a protein having the activity of a D-xylose dehydrogenase from coryneform bacteria.

Another embodiment of the present invention furthermore relates to the use of said D-xylose dehydrogenase for the preparation of D-xylonate. In an embodiment of the present invention, the D-xylonate is prepared in a homologous system, preferably in coryneform bacteria.

Another embodiment of the present invention relates to a coryneform bacterial cell for preparing D-xylonate, characterized in that it has an enhanced expression and/or increased activity of a homologous D-xylose dehydrogenase.

A coryneform bacterial cell selected from the group comprising *Corynebacterium* and *Brevibacterium* is preferred.

Another embodiment of the present invention relates to a nucleic acid sequence which encodes a D-xylonate dehydrogenase according to certain embodiments of the invention from a coryneform bacterial cell.

Another embodiment of the present invention relates to a coryneform bacterial cell in which an increased expression of the encoding nucleic acid sequence according to certain embodiments of the invention is present. Another embodiment of the present invention also includes a coryneform bacterial cell having the aforementioned properties which is not recombinantly modified and thus represents a non-genetically modified system (non-GMO) for the preparation of D-xylonate.

Another embodiment are corynform bacterial cells which are a homologous system for D-xylonate preparation and in which an IolR-mediated deregulation of the D-xylose dehydrogenase is present without modifying the expression and/or activity of the regulator protein IoLR itself. Another embodiment of the present invention thus relates to a coryneform bacterial cell which is characterized in that the functionality of one or more operatively linked IolR binding sites in the regulatory, non-coding region of the nucleic acid sequence encoding the D-xylose dehydrogenase is reduced or turned off, or one or more IolR binding sites are partially or completely deleted.

One embodiment relates to a process for the microbial preparation of D-xylonate, preferably with coryneform bacteria, comprising the steps of:
a) providing a solution containing water and a C5 carbon source,
b) microbial reaction of the C5 carbon source in a solution according to step a) to form D-xylonate in the presence of a coryneform bacterial cell according to certain embodiments of the invention in which the expression of a nucleic acid sequence encoding a homologous D-xylose dehydrogenase is enhanced and/or in which the activity of a homologous D-xylose dehydrogenase is increased, and wherein
c) isolating and/or conditioning D-xylonate from the solution optionally takes place.

Another embodiment of the present invention is a process in which the microbial reaction to form D-xylonate takes place in a solution containing water and a C5 carbon source selected from the group comprising:
a) oligosaccharides or polysaccharides containing D-xylose units,
b) D-xylose, preferably at a concentration of at least 10 $gL^{-1}$,
c) lignocellulose-, cellulose-, or hemicellulose-containing biomass, the hydrolyzate thereof or extract obtained therefrom containing D-xylose units, and
d) a combination of a) to c).

In a preferred variant of the process according to certain embodiments of the invention, bagasse, preferably cane sugar bagasse, its hydrolyzate, or extract obtained therefrom containing D-xylose units is used as the C5 carbon source.

The invention also relates to the use of a D-xylose dehydrogenase according to certain embodiments of the invention from coryneform bacteria, a nucleic acid sequence according to certain embodiments of the invention encoding such a D-xylose dehydrogenase, and coryneform bacterial cells according to certain embodiments of the invention for preparing D-xylonate, preferably with coryneform bacterial cells. In addition to the preparation of D-xylonate in a homologous system (corynform bacteria), the invention also includes the preparation of D-xylonate by means of the D-xylose dehydrogenase according to certain embodiments of the invention in a heterologous system.

The invention also relates to the use of D-xylonate, prepared with a D-xylose dehydrogenase according to certain embodiments of the invention, a coryneform bacterial cell according to certain embodiments of the invention or according to a process according to certain embodiments of the invention or a composition according to certain embodiments of the invention, for preparing pharmaceuticals, foodstuffs, feeds, solvents, colorants, and/or components of the building material industry, preferably cement or concrete.

In the following, embodiments of the invention are explained in more detail using examples and figures, without the subject matter of the invention being limited thereby.

Some definitions that are important to the understanding of the present invention precede the description of the exemplary embodiments.

Another embodiment of the present invention is the provision of a D-xylose dehydrogenase isolated from coryneform bacteria and a nucleic acid sequence encoding such a protein from coryneform bacteria.

Another embodiment of the present invention relates to a D-xylose dehydrogenase in which the amino acid sequence has at least 70% identity to the amino acid sequence according to SEQ ID NO. 2 or fragments thereof.

Also included as embodiments of the invention are proteins encoding an amino acid sequence with at least 75 or 80%, preferably at least 81, 82, 83, 84, 85, or 86% identity, particularly preferably at least 87, 88, 89, 90% identity, very particularly preferably at least 91, 92, 93, 94, 95% identity, or most preferably 96, 97, 98, 99, or 100% identity to the amino acid sequence according to SEQ ID NO. 2 or fragments thereof. In addition, the present invention relates to a D-xylose dehydrogenase containing an amino acid sequence according to SEQ ID NO. 2 or fragments thereof.

Another embodiment of the invention is a D-xylose dehydrogenase encoded by a nucleic acid sequence containing at least 70% identity to the nucleic acid sequence according to SEQ ID NO. 1 or fragments or alleles thereof. Also included in the invention are nucleic acid sequences which have at least 75% or 80%, preferably at least 81, 82, 83, 84, 85, or 86% identity, particularly preferably 87, 88, 89, 90% identity, very particularly preferably at least 91, 92, 93, 94, 95% identity, or most preferably 96, 97, 98, 99, or 100% identity to the nucleic acid sequence SEQ ID NO. 1 or fragments or alleles thereof. In addition, an embodiment of the present invention relates to a D-xylose dehydrogenase encoded by a nucleic acid sequence according to SEQ ID NO. 1 or fragments or alleles thereof.

In a further variant of the present invention, the protein according to certain embodiments of the invention or the nucleic acid sequence according to certain embodiments of the invention is isolated from coryneform bacteria selected from the group comprising *Corynebacterium* and *Brevibacterium*, in particular *Corynebacterium glutamicum, Corynebacterium acetoglutamicum, Corynebacterium thermoaminogenes, Brevibacterium flavum, Brevibacterium lactofermentum*, or *Brevibacterium divaricatum*.

In a preferred variant of the present invention, the protein according to certain embodiments of the invention or the nucleic acid sequence according to certain embodiments of the invention is isolated from coryneform bacteria selected from the group comprising *Corynebacterium glutamicum* ATCC13032, *Corynebacterium acetoglutamicum* ATCC15806, *Corynebacterium acetoacidophilum* ATCC13870, *Corynebacterium thermoaminogenes* FERM BP-1539, *Brevibacterium flavum* ATCC14067, *Brevibacterium lactofermentum* ATCC13869, *Brevibacterium divaricatum* ATCC14020.

According to certain embodiments of the invention, a protein is provided from coryneform bacteria, with which protein the preparation of D-xylonate from D-xylose in coryneform bacteria, that is to say in a homologous system, is made possible for the first time. In contrast to the described annotation as inositol-2-dehydrogenase (IolG EC 1.1.1.18, encoded by iolg; Klaffl et al, 2013; https://doi.org/10.1128/JB.00265-13), remarkably, the D-xylose dehydrogenase according to certain embodiments of the invention does not have any inositol-2-dehydrogenase activity. Unexpectedly, the D-xylose dehydrogenase according to certain embodiments of the invention, with which the preparation of D-xylonate from D-xylose in corynform bacteria is made possible according to certain embodiments of the invention, additionally has no significant homology to other known D-xylose dehydrogenases, such as xylB from *Caulobacter crescentus*. A protein having the structure and the specific function of the D-xylose dehydrogenase according to certain embodiments of the invention from coryneform bacteria has not hitherto been known. Contrary to the general technical knowledge of structural and functional properties of iolG/IolG, it is thanks to the present invention that a concrete homologous target sequence (homologous "target") from coryneform bacteria for the production of D-xylonate from D-xylose in coryneform bacteria (thus in a homologous system) is identified and provided. Thus, by isolating and providing a nucleic acid sequence according to certain embodiments of the invention, encoding a D-xylose dehydrogenase according to certain embodiments of the invention, one or more novel structural elements and variations thereof are made available, with the aid of which D-xylonate can be prepared from D-xylose, preferably in coryneform bacteria as a homologous system. According to certain embodiments of the invention, the D-xylonate production takes place in vitro, preferably enzymatically with an isolated D-xylose dehydrogenase according to certain embodiments of the invention, or in the living organism, preferably microbially in bacteria, yeasts, or fungi. The D-xylonate is particularly preferably prepared in coryneform bacteria or organisms of the genus *Saccharomyces* or *Aspergillus*. In one variant, the present invention for the first time provides a homologous system for preparing D-xylonate with coryneform bacteria.

Thus, by isolating and providing a nucleic acid sequence according to certain embodiments of the invention, encoding a D-xylose dehydrogenase according to certain embodiments of the invention, one or more novel structural elements are made available, with the aid of which D-xylonate can be prepared from D-xylose. According to certain embodiments of the invention, D-xylonate is prepared in vitro, preferably enzymatically with an isolated D-xylose dehydrogenase according to certain embodiments of the invention, or in the living organism, preferably microbially in bacteria, yeasts, or fungi. D-xylonate is particularly preferably prepared in coryneform bacteria or organisms of the genus *Saccharomyces* or *Aspergillus*. Embodiments of the present invention furthermore clearly show that by means of minimal and extremely definite nucleotide substitutions in the 5' upstream regulatory regions of the encoding gene sequences for Iolt 1 and IolG, a clearly increased D-xylonate preparation can be achieved: And this without having to introduce genes or structures of heterologous organisms into the coryneform bacterial strain, which would be undesirable, and also without the need for drastic deletions to be made on centrally acting regulators (IolR), which can trigger widely undefined physiological effects in an organism. The few targeted nucleotide substitutions according to certain embodiments of the invention are present in this case to an extent that they are absolutely also found in nature, which distinguishes the coryneform bacterial strain according to certain embodiments of the invention as non-GMO. Thus, in one variant, the present invention provides for the first time a homologous system for the preparation of D-xylonate with coryneform bacteria.

"Homologous" within the meaning of the invention means that the D-xylonate dehydrogenase according to certain embodiments of the invention and the nucleic acid sequence encoding it are derived relationally from a common parent strain of coryneform bacterial cells. According to the invention, "homologous" is used synonymously with the term "non-heterologous."

Remarkably, the D-xylose dehydrogenase according to certain embodiments of the invention or the nucleic acid sequence according to certain embodiments of the invention encoding it has only about 15% identity to the best described D-xylose dehydrogenase (XylB encoded by the gene xylB) from *Caulobacter cresentus* (FIG. 1).

An embodiment of the invention is a nucleic acid sequence isolated from coryneform bacteria encoding a D-xylose dehydrogenase. A variant of the present invention relates to a nucleic acid sequence isolated from coryneform bacteria encoding a D-xylose dehydrogenase for preparing D-xylonate, wherein the preparation according to certain embodiments of the invention takes place both in vitro and in living organisms.

Further variants according to certain embodiments of the invention relate to an in-vitro preparation of D-xylonate, and here preferably to an enzymatic preparation with the aid of the D-xylose dehydrogenase according to certain embodiments of the invention in isolated form. Another embodiment of the invention is a preparation of D-xylonate in living organisms, particularly preferably a microbial preparation (e.g., culturing) of D-xylonate in host cells selected from the group comprising coryneform bacteria, yeasts, and fungi. Particularly preferred according to certain embodiments of the invention is a microbial preparation (e.g., culturing) of D-xylonate in host cells of the genus selected from the group comprising *Corynebacterium, Brevibacterium, Saccharomyces*, and *Aspergillus*. Very particularly preferred according to certain embodiments of the invention is a microbial preparation (e.g., culturing) of D-xylonate in *Corynebacterium*. The invention also includes D-xylose preparation with *Saccharomyces cerevisiae, Aspergillus niger*, or *Corynebacterium glutamicum*.

Certain embodiments of the invention relate to nucleic acid sequences selected from the group comprising a) a nucleic acid sequence containing at least 70% identity to the nucleic acid sequence according to SEQ ID NO. 1 or fragments or alleles thereof, or b) a nucleic acid sequence which, under stringent conditions, hybridizes with a complementary sequence of a nucleic acid sequence according to SEQ ID NO. 1 and/or fragments and/or alleles thereof, or c) a nucleic acid sequence according to SEQ ID NO. 1 or fragments or alleles thereof, or d) a nucleic acid sequence encoding a D-xylose dehydrogenase corresponding to each of the nucleic acids according to a)-c) but which differs from these nucleic acid sequences according to a)-c) by the degeneracy of the genetic code or functionally neutral mutations. Certain embodiments of the present invention relate to nucleic acid sequences according to the invention for the preparation of D-xylonate. D-xylonate is preferably prepared according to certain embodiments of the invention in living microorganisms, particularly preferably in coryneform bacteria.

Certain embodiments of the present invention also relate to a nucleic acid sequence which is characterized in that the functionality of one or more operatively linked IolR binding sites in the regulatory, non-coding region of the nucleic acid sequence according to the invention encoding the D-xylose dehydrogenase is reduced or turned off, or one or more operatively linked IolR binding sites are partially or completely deleted.

Within the meaning of the present invention, a "reduced or turned-off functionality" does not refer to the functionality of the D-xylose dehydrogenase according to certain embodiments of the invention and the nucleic acid sequence according to certain embodiments of the invention encoding it but specifically to the modified functionality of the IolR binding sites to which the centrally acting regulator protein IolR normally binds, thereby repressing the expression of the encoding nucleic acid sequence. Within the meaning of the present invention, "reduced" or "turned off" means that the expression of the encoding nucleic acid sequence is worse or no longer under the expression control of the regulator IolR compared to the situation in a wild-type host cell. In the context of the present invention, "reduced" or "turned off" is intended to be synonymous with "deregulated" or "derepressed."

The term "nucleic acid sequence" within the meaning of the present invention means any homologous molecular unit which transports genetic information. Accordingly, this relates to a homologous gene, preferably a naturally occurring and/or non-recombinant homologous gene, and to a homologous transgene or codon-optimized homologous genes. The term "nucleic acid sequence" according to the invention refers to a nucleic acid sequence or fragments or alleles thereof that code or express a specific protein. Preferably, the term "nucleic acid sequence" refers to a nucleic acid sequence containing regulatory sequences that precede (upstream, 5' non-coding sequence) and follow (downstream, 3' non-coding sequence) the encoding sequence. The term "naturally occurring" gene refers to a gene found in nature, e.g., from a wild-type strain of a coryneform bacterial cell, with its own regulatory sequences.

Within the meaning of the present invention, the term "operatively linked region" relates to an association of nucleic acid sequences on a single nucleic acid fragment so that the function of the one nucleic acid sequence is influenced by the function of the other nucleic acid sequence. In the context of a promoter or binding site for a regulator protein, the term "operatively linked" within the meaning of the invention means that the encoding sequence is under the control of the regulatory region (especially of the promoter or of the regulator binding site) which regulates the expression of the encoding sequence.

More than 22 different genes are thought to be regulated by the regulator protein IolR. For example, iolR itself (negative autoregulation), iolT1, iolC (and the other genes organized with iolC in a cluster or operon) are known to be regulated by IolR. The nucleic acid sequence according to certain embodiments of the invention encoding a D-xylose dehydrogenase according to certain embodiments of the invention (and annotated in its function as inositol-2-dehydrogenase encoded by iolG) is organized in coryneform bacteria in the myo-inositol catabolism gene cluster (Klaffl et al, 2013; https://doi.org/10.1128/JB.00265-13). Since the first gene in this gene cluster is the iolC gene, it is hereinafter referred to as an iolC cluster. The regulatory region operatively linked to the iolC cluster thus also regulates the expression of the iolG gene and thus the nucleic acid sequence according to certain embodiments of the invention encoding the D-xylose dehydrogenase according to certain embodiments of the invention.

The term "modification" within the meaning of the present invention also means, for example, "genetic modification," which means, according to the invention, that although a genetic engineering process is used, no insertions of nucleic acid molecules are produced. Within the meaning of the invention, "modifications" means substitutions and/or deletions, preferably substitutions. Within the meaning of the present invention, "modification" or "genetic modification" is preferably generated in a regulatory, non-coding region of the nucleic acids according to the invention. All conceivable positions in a regulatory region of encoding genes or gene clusters, the modifications of which have a measurable effect on the functionality of the iolR binding sites and IolR binding, in the sense of "reduced" or "turned off," are intended and included within the meaning of the invention.

A variant of the present invention according to certain embodiments of the invention relates to a nucleic acid sequence having one or more nucleotide substitutions or nucleotide deletions in the operatively linked IolR binding sites of the iolC gene cluster. Preferred variants within the meaning of the invention are those selected from the group of nucleic acid sequences according to SEQ ID NO. 7 and SEQ ID NO. 8.

By means of the isolation and provision according to certain embodiments of the invention of a D-xylose dehydrogenase and a nucleic acid sequence according to certain embodiments of the invention encoding a D-xylose dehydrogenase from coryneform bacterial cells, homologous, genetically defined, non-recombinant (non-GMO) coryneform bacterial cells, which are suitable for the microbial, preferably fermentative production of D-xylonate, can be prepared for the first time.

Within the meaning of the present invention, the term "non-recombinant" is understood to mean that the genetic material of the coryneform bacterial cells according to the invention is only modified in such a way that it could occur naturally, e.g., by natural recombination or natural mutation. The coryneform bacterial cells according to certain embodiments of the invention are thus distinguished as non-genetically modified organisms (non-GMO).

This also opens up the possibility of further optimizing industrially interesting production strains of coryneform bacteria without having to introduce recombinant or heterologous gene material into the cell. Certain embodiments of the present invention thus provide a system by means of which the microbial production of D-xylonate can be carried out in a considerably simpler, more stable, cheaper, and more economical manner. This is because all hitherto known production strains with a D-xylonate synthesis capacity, such as *Gluconobacter oxydans*, require complex media for their growth, as a result of which the cultivation becomes markedly more complex, more expensive, and thus more uneconomical. All of the D-xylonate producers previously described are moreover "non-natural" genetically modified organisms (GMO), inter alia various yeast, fungi, and bacteria. This gives rise to a disadvantage for use in certain industrial sectors (e.g., food and pharmaceutical industries) as a result of complicated approval processes.

The coryneform bacterial cell according to certain embodiments of the invention offers a multiplicity of advantages, a selection of which is described below. Coryneform bacteria, preferably the genus *Corynebacterium*, are a "generally recognized as safe" (GRAS) organism, which can be used in all industrial sectors. Coryneform bacteria achieve high growth rates and biomass yields on defined media (Grünberger et al., 2012) and there is extensive experience in the industrial use of coryneform bacteria (Becker et al., 2012).

A variant of the present invention also includes the use of the previously described nucleic acid sequences according to certain embodiments of the invention for the preparation of living organisms, preferably microorganisms, particularly preferably bacteria, yeasts, or fungi, very particularly preferably the genus of coryneform bacteria, such as *Corynebacterium* or *Brevibacterium, Saccharomyces* or *Aspergillus*, in particular *Corynebacterium glutamicum, Saccharomyces cerevisiae*, or *Aspergillus niger*, for the preparation of D-xylonate.

The invention includes nucleic acid sequences selected from the group comprising SEQ ID NO. 7, SEQ ID NO. 8, SEQ ID NO. 9, SEQ ID NO. 10, SEQ ID NO. 63, or SEQ ID NO. 64 or fragments or alleles thereof for preparing coryneform bacterial cells or other suitable organisms according to certain embodiments of the invention for the preparation of D-xylonate. The variants according to SEQ ID NO. 7 and SEQ ID NO. 63 of the nucleic acid sequences according to certain embodiments of the invention contain nucleotide exchanges, i.e., substitutions, in the operatively linked promoter region of the iolC gene cluster containing the nucleotide sequence (iolG) encoding the D-xylose dehydrogenase according to certain embodiments of the invention. The variants according to SEQ ID NO. 8 or SEQ ID NO. 64 of the nucleic acid sequences according to certain embodiments of the invention contain nucleotide deletions in the operatively linked promoter region of the iolC gene cluster containing the nucleotide sequence (iolG) encoding the D-xylose dehydrogenase according to certain embodiments of the invention. A further variant of the present invention relates to the use of a nucleic acid sequence according to SEQ ID NO. 7 or 8 for the preparation of coryneform bacteria. The invention also includes the use of the nucleic acid sequences selected from the group comprising SEQ ID NO. 63 and SEQ ID NO. 64 for the preparation of coryneform bacteria.

Certain embodiments of the present invention are also nucleic acid sequences containing nucleotide substitutions or deletions in the operatively linked promoter region of the iolT1 gene of the myo-inositol/proton symporter. Preferred variants include nucleic acid sequences according to SEQ ID NO. 9 or SEQ ID NO. 10. A preferred variant of the present invention relates to the use of a nucleic acid sequence according to SEQ ID NO. 9 or SEQ ID NO. 10 in which the operatively linked IolR binding sites are deleted for the preparation of coryneform bacteria.

Particular preference is given to a coryneform bacterial cell in which there are one or more modifications, selected from the group containing one or more substitutions or one or more deletions in the chromosome.

Certain embodiments of the present invention are a coryneform bacterial cell for preparing D-xylonate, characterized in that it exhibits enhanced expression and/or increased activity of a homologous D-xylose dehydrogenase according to the invention.

Within the meaning of the present invention, "enhanced" is understood to mean "increased," "improved," "modified," or "deregulated," and is used synonymously. "Enhanced" within the meaning of the present invention means, for example, the enhanced gene expression of a gene compared to the expression of the respective parent gene in the unmodified, naturally unenhanced state. Within the meaning of the invention, the same is meant with respect to the increased enzyme activity. For example, the wild type of a coryneform bacterial cell represents a genetically unmodified parent gene or enzyme. Coryneform wild-type cells of the genus *Corynebacterium* or *Brevibacterium* are preferred; particular preference is given to coryneform bacterial cells of the wild type *Corynebacterium glutamicum*; very particular preference is given to coryneform bacterial cells of the wild type *Corynebacterium glutamicum* ATCC 13032.

A variant of the present invention includes a coryneform bacterial cell, characterized in that it has an enhanced expression of a nucleic acid sequence according to one of the variants described above. A further variant of a coryneform bacterial cell according to certain embodiments of the invention is characterized in that the enhanced expression of the D-xylose dehydrogenase is based on modifications selected from the group comprising a) modifying the regulation or signal structures for gene expression, b) modifying the transcription activity of the encoding nucleic acid sequence, or c) increasing the gene copy number of the encoding nucleic acid sequence. The invention thereby includes modification of the signal structures of the gene expression, such as by modifying the repressor genes, activator genes, operators, promoters; attenuators, ribosome binding sites, start codon, terminators. Also included are the introduction of a stronger promoter, such as the tac promoter or an IPTG-inducible promoter. The introduction of a stronger promoter, such as the tac promoter (Amann et al (Gene 1988 69:301-15), or promoters from the group of promoters described in Patek et al (Microbiology 1996 142:1297), is preferred but not limiting for the present invention. Further examples can be found in WO 96/15246 or in Boyd and Murphy (Journal of Bacteriology 170: 5949 (1988)), in Voskuil and Chambliss (Nucleic Acids Research 26: 3548 (1998), Jensen and Hammer (Biotechnology and Bioengineering 58: 191 (1998)), in Patek et al. (Microbiology 142: 1297 (1996)), in Knippers ("Molekulare Genetik [Molecular Genetics]," 6th edition, Georg Thieme Verlag, Stuttgart, Germany, 1995) or also in Winnacker ("Gene and Clone," VCH Verlagsgesellschaft, Weinheim, Germany, 1990). In further variants of the invention, an increased gene copy number of the encoding nucleic acid sequence according to certain embodiments of the invention can be chromosomally encoded or vector-based, preferably plasmid-encoded. The present invention relates to a coryneform bacterial cell in which the increase in the copy number is chromosomally encoded or extra-chromosomally encoded, preferably vector-encoded or plasmid-encoded. Suitable plasmids according to certain embodiments of the invention are those replicated in coryneform bacteria. Numerous known plasmid vectors, such as pZ1 (Menkel et al., Applied and environmental Microbiology (1989) 64: 549-554), pEKEx1 (Eikmanns et al., Gene 102:93-98 (1991)) or pHS2-1 (Sonnen et al., Gene 107:69-74 (1991)), are based on the cryptic plasmids pHM1519, pBL1, or pGA1. Other plasmid vectors, such as those based on pCG4 (U.S. Pat. No. 4,489,160), or pNG2 (Serwold-Davis et al., FEMS Microbiology Letters 66, 119-124 (1990)), or pAG1 (U.S. Pat. No. 5,158,891), can be used in the same manner (O. Kirchner 2003, J. Biotechnol. 104: 287-99). Regulatable expression vectors may also be used, such as pEKEx2 (B. Eikmanns, 1991 Gene 102:93-8; 0. Kirchner 2003, J. Biotechnol. 104:287-99). The gene can also be expressed by integration into the chromosome as a single copy (P. Vasicova 1999, J. Bacteriol. 181:6188-91) or multiple copy (D. Reinscheid 1994 Appl. Environ Microbiol 60:126-132). Transformation of the desired strain with the vector to increase the copy number is accomplished by conjugation or electroporation of the desired strain of *C. glutamicum*, for example. The process of conjugation is described, for example, in Schafer et al. (Applied and environmental Microbiology (1994) 60:756-759). Processes for transformation are described, for example, in Tauch et al. (FEMS Microbiological Letters (1994) 123:343-347).

A further variant of the present invention relates to a coryneform bacterial cell, characterized in that the increased activity of the D-xylose dehydrogenase activity is based on modifications selected from the group comprising a) an increase in the expression of the encoding nucleic acid sequence, b) an expression of a nucleic acid sequence of fragments thereof encoding a D-xylose dehydrogenase with increased catalytic activity and/or substrate specificity, c) an increase in the stability of the mRNA derived from the encoding nucleic acid sequence, or d) a modification in the catalytic activity and/or substrate specificity of a homologous D-xylose dehydrogenase for the conversion of D-xylose or a combination of a)-d). The increase in mRNA stability can be achieved, for example, by mutation of the terminal positions which control the termination of transcription. Measures which lead to a modification of the catalytic properties of enzyme proteins, in particular to a modified substrate specificity, are known from the prior art. In addition to preferred partial or complete deletions of regulatory structures according to certain embodiments of the invention, the invention also includes modifications, such as transitions, transversions, or insertions, as well as directed evolution processes. Instructions for generating such modifications can be found in known textbooks (R. Knippers "Molekulare Genetik [Molecular Genetics]," 8th edition, 2001, Georg Thieme Verlag, Stuttgart, Germany).

A preferred variant of the present invention comprises a coryneform bacterial cell in which the functionality of one or more operatively linked IolR binding sites in the regulatory, non-coding region of the nucleic acid sequence encoding the D-xylose dehydrogenase is reduced or turned off, or one or more IolR binding sites are partially or completely deleted.

The present invention also relates to a coryneform bacterial cell which has a nucleic acid sequence with one or more nucleotide substitutions or nucleotide deletions in the operatively linked IolR binding sites of the iolC gene cluster (containing the nucleic acid sequence iolG encoding the D-xylose dehydrogenase according to certain embodiments of the invention). Preferred variants according to certain embodiments of the invention comprise sequences selected from the group of SEQ ID NO. 7 and SEQ ID NO. 8. Further variants according to certain embodiments of the invention comprise sequences selected from the group comprising SEQ ID NO. 63 and SEQ ID NO. 64.

The present invention furthermore relates to a coryneform bacterial cell having a nucleic acid sequence with one or more nucleotide substitutions or nucleotide deletions in the operatively linked IolR binding sites of the iolT1 gene. Variants according to certain embodiments of the invention comprise sequences selected from the group of nucleic acid sequences SEQ ID NO. 9 and SEQ ID NO. 10.

An advantage of the modification according to certain embodiments of the invention of the IolR binding sites in the regulatory region, which is associated with the nucleic acid sequence according to certain embodiments of the invention encoding the D-xylose dehydrogenase according to certain embodiments of the invention, is that the corresponding coryneform bacteria according to certain embodiments of the invention are not modified recombinantly. It is particularly advantageous that the IolR regulator protein itself or the correspondingly encoding iolR gene is not modified. This has the enormous advantage that negative physiological effects are excluded as a consequence of an inactivation of iolR/IolR. As non-GMO, the bacterial cells according to certain embodiments of the invention thus represent a very attractive platform for the large-scale or industrial production of D-xylonate in a homologous system.

Certain embodiments of the present invention thus also relate to a coryneform bacterial cell which is not recombinantly modified. Thus, the invention also includes a coryneform bacterial cell which is not genetically modified (non-GMO).

Certain embodiments of the present invention also relate to a coryneform bacterial cell in which the increased copy number of a nucleic acid sequence encoding D-xylose dehydrogenase according to the invention is chromosomally encoded.

Certain embodiments of the present invention also relate to a coryneform bacterial cell in which the increased copy number of a nucleic acid sequence encoding D-xylose dehydrogenase according to the invention is vector-encoded, preferably plasmid-encoded.

Preferred variants of the present invention include coryneform bacteria in which the iolG gene is chromosomally encoded at an increased copy number and the corresponding IolR binding sites are deleted. In a further preferred variant, the coryneform bacterial cell according to certain embodiments of the invention additionally comprises an iolT1 gene modified by deletions, which because of this is expressed IolR-independently. These non-recombinant, i.e., homologous, and also precisely defined, coryneform bacterial cells are advantageously suitable for the large-scale microbial production of D-xylonate in solutions with D-xylose-containing carbon and energy sources.

According to certain embodiments of the invention, in addition to increasing the xylose dehydrogenase activity, it may be advantageous for the production of D-xylonate to modify the expression or activity of one or more other genes or proteins which are likewise regulated by the regulator protein IolR.

Normally, genetically unmodified coryneform bacteria cannot metabolize D-xylose as the only source of carbon and energy. It is known that the so-called isomerase and Weimberg metabolic pathway must be implemented heterologously for the oxidative metabolization of D-xylose in coryneform bacteria. Through the heterologous expression of corresponding genes from organisms such as xylB from *Caulobacter crescentus*, a coryneform bacterium can also convert D-xylose enzymatically. However, a heterologous expression is primarily undesirable according to certain embodiments of the invention due to the associated negative properties for industrial D-xylonate production. It is furthermore known that a myo-inositol/proton symporter (IolT1), the genes of which are controlled by the IolR regulator protein, contributes to the uptake of D-xylose in the cell of coryneform bacteria. Thus, by modifications, such as deletions or nucleotide substitutions, in the regulatory region of the iolT1 gene, by means of which the binding of the iolR regulator gene is prevented, a bacterial strain independent of the regulation of the iolR regulator can thus be generated. In a further variant of a coryneform bacterial cell according to certain embodiments of the invention, a deregulated iolT1 gene is present in which an inventive enhanced expression and/or increased activity of the D-xylose dehydrogenase according to certain embodiments of the invention is also present. The iolT2 gene is also relevant for D-xylose catabolism. The invention includes a coryneform bacterial cell containing an enhanced expression of iolT2 gene and/or an increased activity of the myo-inositol/proton symporter IolT2.

Another embodiment of the present invention is a coryneform bacterial cell a) wherein the activity of a D-xylose dehydrogenase according to certain embodiments of the invention is increased, b) wherein a nucleic acid sequence according to certain embodiments of the invention encoding a D-xylose dehydrogenase according to certain embodiments of the invention is enhancedly expressed, c) wherein a nucleic acid sequence encoding a myo-inositol/proton symporter (IolT1) according to SEQ ID NO. 3 or fragments or alleles thereof is enhancedly expressed, d) wherein a myo-inositol/proton symporter IolT1 with an amino acid sequence according to SEQ ID NO. 4 or fragments thereof has increased activity, e) having a nucleic acid sequence encoding a myo-inositol/proton symporter (IolT1) having one or more nucleotide substitutions or nucleotide deletions in the operatively linked IolR binding sites of the iolT1 gene selected from the group of nucleic acid sequences SEQ ID NO. 9 and SEQ ID NO. 10 or fragments thereof, f) wherein a nucleic acid sequence encoding a myo-inositol/proton symporter (IolT2) according to SEQ ID NO. 5 or fragments or alleles thereof is enhancedly expressed, g) wherein a myo-inositol/proton symporter IolT2 with an amino acid sequence according to SEQ ID NO. 6 or fragments thereof is increased in its activity, h) wherein both nucleic acid sequences encoding myo-inositol/proton symporters IolT1/2/according to c) and f) are enhancedly expressed, i) wherein both myo-inositol/proton symporters IolT1/2 according to d) and g) have increased activity, j) having a nucleic acid sequence, wherein the functionality of one or more operatively linked IolR binding sites in the regulatory, non-coding region of the iolC gene cluster (containing iolG encoding a D-xylose dehydrogenase according to certain embodiments of the invention) is reduced or turned off, or one or more IolR binding sites are partially or completely deleted, k) having a nucleic acid sequence, which has one or more nucleotide substitutions or nucleotide deletions in the operatively linked IolR binding sites of the iolC gene cluster, preferably selected from the group consisting of nucleic acid sequences according to SEQ ID NO. 7, SEQ ID NO. 8, SEQ ID NO. 63, and SEQ ID NO. 64 or fragments or alleles thereof, or l) a combination of a)-k).

In a preferred variant of a coryneform bacterial cell according to certain embodiments of the invention, said cell comprises defined modifications of its genome, namely those of a deregulated iolT1 gene and of a deregulated iolG gene. Furthermore preferred are modifications to the regulatory regions of the iolT1 gene or/and iolG gene (or of the iolC gene cluster containing the iolG gene). In particular, preference is given here to substitutions or deletions of the binding sites of the IolR regulator protein. Deletions are furthermore preferred. The bacterial cells according to certain embodiments of the invention are not genetically modified and have no recombinant DNA, which makes them particularly advantageous for use in the large-scale production of D-xylonate, such as in the pharmaceutical or food industry.

In a variant of the present invention, a nucleic acid sequence encoding a myo-inositol regulator IolR or fragments or alleles thereof may also be completely or partially deleted or the expression of an iolR gene may be reduced or be absent or a myo-inositol regulator IolR may be reduced in its activity or completely turned off.

Preferred variants of a coryneform bacterial cell are selected from the group comprising *Corynebacterium, Brevibacterium*, in particular *Corynebacterium glutamicum, Corynebacterium acetoglutamicum, Corynebacterium thermoaminogenes, Brevibacterium flavum, Brevibacterium lactofermentum,* or *Brevibacterium divaricatum*. Particularly preferred variants of a coryneform bacterial cell are selected from the group consisting of *Corynebacterium glutamicum* ATCC13032, *Corynebacterium acetoglutamicum* ATCC15806, *Corynebacterium acetoacidophilum* ATCC13870, *Corynebacterium thermoaminogenes* FERM BP-1539, *Brevibacterium flavum* ATCC14067, *Brevibacterium lactofermentum* ATCC 13869, or *Brevibacterium divaricatum* ATCC 14020. *Corynebacterium glutamicum* is particularly preferred but not limiting.

A D-xylose dehydrogenase according to certain embodiments of the invention, a nucleic acid sequence according to certain embodiments of the invention encoding it, and a use according to certain embodiments of the invention are also suitable for the preparation of D-xylonate in the broadest sense, in which, for example, a homologous expression system is not absolutely necessary. Thus, the invention also includes heterologous systems or host cells or organisms having the D-xylose dehydrogenase according to certain embodiments of the invention and/or the nucleic acid sequence according to certain embodiments of the invention encoding it and/or in which a use according to certain embodiments of the invention of the aforementioned elements (such as (regulatory) sequences, genes, proteins) or a process for the preparation of D-xylonate takes place. Thus, the invention includes both a coryneform bacterial cell and also a heterologous host system in which the expression of the iolR gene is reduced or is absent, or the iolR gene is partially or completely deleted, or the IolR regulator protein is reduced in its activity or is completely turned off.

Further variants according to certain embodiments of the invention relate to an in-vitro preparation of D-xylonate, preferably an enzymatic preparation with the aid of a purified D-xylose dehydrogenase according to certain embodiments of the invention. Preferred according to certain embodiments of the invention is a microbial preparation (e.g., culture) of D-xylonate in host cells selected from the group comprising coryneform bacteria, yeasts, and fungi. Particularly preferred according to certain embodiments of the invention is a microbial preparation of D-xylonate in host cells of the genus selected from the group comprising *Corynebacterium, Brevibacterium, Saccharomyces,* and *Aspergillus*. Very particularly preferred according to certain embodiments of the invention is a microbial preparation (e.g., culture) of D-xylonate in *Corynebacterium*. The invention also includes D-xylose preparation with *Saccharomyces cerevisiae, Aspergillus niger,* or *Corynebacterium glutamicum*.

Another embodiment of the invention relate to a use of the D-xylose dehydrogenase according to certain embodiments of the invention or the nucleic acid sequence according to certain embodiments of the invention encoding it for use in heterologous systems or in-vitro systems for biotechnological preparation of D-xylonate from D-xylose.

Another embodiment of the present invention is a process for preparing D-xylonate, comprising the following steps:
  e) providing a solution containing water and a C5 carbon source,
  f) microbial reaction of the C5 carbon source in a solution according to step a) to form D-xylonate in the presence of a coryneform bacterial cell according to certain embodiments of the invention in which the expression of a nucleic acid sequence encoding a homologous D-xylose dehydrogenase is enhanced and/or in which the activity of a homologous D-xylose dehydrogenase is increased, and
  g) optionally isolating and/or conditioning D-xylonate from the solution.

According to the invention, "solution" is equivalent in meaning to "medium," "culture medium," "culture broth," or "culture solution." Within the meaning of the present invention, "microbial" is equivalent in meaning to "biotechnological" or "fermentative." According to the invention, "reaction" is equivalent in meaning to "metabolization" or "cultivation." According to the invention, "conditioning" is equivalent in meaning to "separation," "concentration," or "purification."

A coryneform bacterial cell according to certain embodiments of the invention is used in variants of the process according to certain embodiments of the invention. The invention comprises a process in which the D-xylose dehydrogenase in step b) has an amino acid sequence of at least 70% identity to the amino acid sequence according to SEQ ID NO. 2 or fragments thereof or is encoded by a nucleic acid sequence which has at least 70% identity to the nucleic acid sequence according to SEQ ID NO. 1 or fragments or alleles thereof. A further variant of the present invention includes a process using a coryneform bacterial cell according to certain embodiments of the invention a) wherein the activity of a D-xylose dehydrogenase according to certain embodiments of the invention is increased, b) wherein a nucleic acid sequence according to certain embodiments of the invention encoding a D-xylose dehydrogenase according to certain embodiments of the invention is enhancedly expressed, c) wherein a nucleic acid sequence encoding a myo-inositol/proton symporter (IolT1) according to SEQ ID NO. 3 or fragments or alleles thereof is enhancedly expressed, d) wherein a myo-inositol/proton symporter IolT 1 with an amino acid sequence according to SEQ ID NO. 4 or fragments thereof is increased in its activity, e) having a nucleic acid sequence encoding a myo-inositol/proton symporter (IolT1) having one or more nucleotide substitutions or nucleotide deletions in the operatively linked IolR binding sites of the iolT1 gene selected from the group of nucleic acid sequences SEQ ID NO. 9 and SEQ ID NO. 10 or fragments or alleles thereof, f) wherein a nucleic acid sequence encoding a myo-inositol/proton symporter (IolT2) according to SEQ ID NO. 5 or fragments or alleles thereof is enhancedly expressed, g) wherein a myo-inositol/proton symporter IolT2 with an amino acid sequence according to SEQ ID NO. 6 or fragments thereof is increased in its activity, h) wherein both nucleic acid sequences encoding myo-inositol proton symporters IolT1/2/according to c) and f) are enhancedly expressed, i) wherein both myo-inositol/proton symporters IolT1/2 according to d) and g) are increased in their activity, j) having a nucleic acid sequence, wherein the functionality of one or more operatively linked IolR binding sites in the regulatory, non-coding region of the iolC gene cluster (containing iolG encoding a D-xylose dehydrogenase according to certain embodiments of the invention) is reduced or turned off, or one or more IolR binding sites are partially or completely deleted, k) having a nucleic acid sequence, which has one or more nucleotide substitutions or nucleotide deletions in the operatively linked IolR binding sites of the iolC gene cluster, preferably selected from the group consisting of nucleic acid sequences according to SEQ ID NO. 7, SEQ ID NO. 8, SEQ ID NO. 63. and SEQ ID NO. 64 or fragments or alleles thereof, or l) a combination of a)-k).

In a variant of the process according to certain embodiments of the invention, a coryneform bacterial cell can also be used, which has a nucleic acid sequence encoding a myo-inositol regulator IolR or fragments thereof, which are completely or partially deleted or in which the expression of an iolR gene is reduced or absent, or a myo-inositol regulator IolR which is reduced in activity or completely turned off.

Another embodiment of the present invention is a process in which the microbial reaction to form D-xylonate takes place in a solution containing water and a C5 carbon source selected from the group comprising:
  h) oligosaccharides or polysaccharides containing D-xylose units,
  i) D-xylose, preferably at a concentration of at least 10 gL$^{-1}$,
  j) biomass containing lignocellulose, cellulose, or hemicellulose, the hydrolyzate thereof or extract obtained therefrom containing D-xylose units, and
  k) a combination of a) to c).

In a preferred variant of the process according to certain embodiments of the invention, bagasse, preferably cane sugar bagasse, its hydrolyzate or extract obtained therefrom containing D-xylose is used as the C5 carbon source. One variant of the process according to certain embodiments of the invention includes a process in which the culture solution contains D-glucose, preferably at least 8 to 10 gL$^{-1}$, as carbon and energy sources at the beginning of the cultivation, alongside D-xylose.

The culture medium to be used should adequately satisfy the requirements of the respective microorganisms. Descriptions of culture media of various microorganisms are contained in the handbook "Manual of Methods for General Bacteriology" of the American Society for Bacteriology (Washington D.C., USA, 1981). Besides D-xylose as starting substrate for D-xylonate formation, sugar and carbohydrates, such as glucose, sucrose, lactose, fructose, maltose, molasses, starch and cellulose, oils and fats, such as soya oil, sunflower oil, peanut oil, and coconut oil, fatty acids, such as palmitic acid, stearic acid, and linoleic acid, alcohols, such as glycerol and ethanol, and organic acids, such as acetic acid, can be used as carbon source. These substances can be used individually or as a mixture. The nitrogen source used may be organic, nitrogen-containing compounds, such as peptones, yeast extract, meat extract, malt extract, maize steeping liquor, soybean meal, and urea or inorganic compounds, such as ammonium sulfate, ammonium chloride, ammonium phosphate, ammonium carbonate, and ammonium nitrate. The nitrogen sources can be used individually or as a mixture. Potassium dihydrogen phosphate or dipotassium hydrogen phosphate or the corresponding sodium-containing salts can be used as phosphorus source. The culture medium should furthermore contain salts of metals, such as magnesium sulfate or iron sulfate, which are necessary for growth. Ultimately, it is possible to use essential growth substances, such as amino acids and vitamins, in addition to the aforementioned substances. The starting materials mentioned can be added to the culture in the form of a one-off batch or fed in appropriately during cultivation. For the pH control of the culture, basic compounds, such as sodium hydroxide, potassium hydroxide, ammonia, or acidic compounds, such as hydrochloric acid, phosphoric acid, or sulfuric acid, are used in an appropriate manner. Antifoam agents, such as fatty acid polyglycol esters, can be used to control foam development. Suitable selective substances, such as antibiotics, can be added to the medium in order to maintain the stability of plasmids. In order to maintain aerobic conditions, oxygen or oxygen-containing gas mixtures, such as air, are introduced into the culture. The temperature of the culture is normally from 20% to 45%, and preferably from 25% to 40%. The culture is continued until a maximum of D-xylonate has formed. This target is normally achieved within 10 hours to 160 hours.

Another embodiment of the present invention relates to a process in which cultivation takes place discontinuously or continuously, preferably in batch, fed batch, repeated fed batch mode or as a one-pot hydrolysis fermentation process.

A preferred variant of a process according to certain embodiments of the invention takes place in fed batch mode. Particularly preferred is the "feeding in" of D-xylose.

Another embodiment of the invention includes a process in which the cultivation of a coryneform bacterial cell according to certain embodiments of the invention takes place in a solution which additionally contains D-glucose, preferably in concentrations of at least 8 to 10 gL$^{-1}$. The invention also relates to a process in which the cultivation of a coryneform bacterial cell according to certain embodiments of the invention takes place in a solution which additionally contains components selected from the group: a) nitrogen, preferably ammonium chloride, b) phosphate, preferably potassium phosphate, c) biotin, and d) a combination of a)-c). This process is particularly preferred in the cultivation of a coryneform bacterial cell according to certain embodiments of the invention with bagasse, preferably cane sugar bagasse, its hydrolyzate or extract containing D-xylose obtained therefrom, as C5 carbon source. The use of biotin is not absolutely necessary for cultivation on bagasse, preferably hydrolyzed bagasse.

In a preferred variant of the process according to certain embodiments of the invention, a coryneform bacterial cell is used which is not modified recombinantly. Thus, the invention also includes a process in which a coryneform bacterial cell which is not genetically modified (non-GMO) is used.

Another embodiment of the present invention relates to the use of a D-xylose dehydrogenase according to certain embodiments of the invention or a nucleic acid sequence according to certain embodiments of the invention or a coryneform bacterial cell according to certain embodiments of the invention for preparing D-xylonate. In one variant of the present invention, D-xylonate is prepared in vitro with purified enzyme.

Another embodiment of the invention relates to the use of a D-xylose dehydrogenase according to certain embodiments of the invention or a nucleic acid sequence according to certain embodiments of the invention for preparing a host system selected from the group comprising coryneform bacteria, preferably *Corynebacterium* or *Brevibacterium*, yeasts, preferably *Saccharomyces*, and fungi, preferably *Aspergillus*. The invention also includes a nucleotide sequence selected from the group SEQ ID NO. 9 or SEQ ID NO. 10, preferably in combination with a nucleic acid sequence according to certain embodiments of the invention, for preparing coryneform bacterial cells for the preparation of D-xylonate. A preferred variant of the present invention is used for the microbial preparation of D-xylonate *Corynebacterium glutamicum*.

Another embodiment of the present invention furthermore relates to a composition containing D-xylonate prepared with a purified enzyme, an enzyme encoded by a nucleic acid sequence, a coryneform bacterial cell, or a process according to the described variants of the present invention. The composition according to certain embodiments of the invention may comprise further substances which are advantageous in the preparation of the desired products. A selection is known to the person skilled in the art from the prior art.

Another embodiment of the present invention is the use of D-xylonate prepared with a purified enzyme, an enzyme encoded by a nucleic acid sequence, a coryneform bacterial cell or according to a process according to the described variants of the present invention, and the use of an aforementioned composition for preparing pharmaceuticals, food, feeds, solvents, colorants, and/or components of the building material industry, preferably cement or concrete. D-xylonate here has the potential to specifically improve the properties of cement or concrete. According to certain embodiments of the invention, it is used as a water reducer, dispersant, or retarder for prolonging the setting time of cement or concrete or other building materials.

Tables and Figures

Table 1 shows an overview of bacterial strains and plasmids of certain embodiments of the present invention. The various strains *C. glutamicum* ATCC13032 iolG$^1$, *C. glutamicum* ATCC13032 iolG$^2$, and *C. glutamicum* ATCC13032 iolG$^3$ represent three integration strains of *C. glutamicum* ATCC13032 with a different number of iolG copies. The strain *C. glutamicum* ATCC13032 iolG¹ has an integration of the homologous iolG gene in the chromosome, this being in the intergenic region between C. cg1121 and cg1122. iolG² is based on iolG¹ and additionally contains a second integration of the homologous iolG gene in the intergenic region between cg0901 and cg0902. iolG³ is based on iolG² and additionally contains a third integration of the homologous iolG gene in the intergenic region between cg3327 and cg3328.

Table 2 shows an overview of the SEQ ID NOs of certain embodiments of the present invention.

according to certain embodiments of the inventionaccording to certain embodiments of the inventionaccording to certain embodiments of the inventionaccording to certain embodiments of the inventionaccording to certain embodiments of the inventionaccording to certain embodiments of the inventionaccording to certain embodiments of the inventionaccording to certain embodiments of the inventionaccording to certain embodiments of the inventionaccording to certain embodiments of the inventionaccording to certain embodiments of the inventionaccording to certain embodiments of the inventionaccording to certain embodiments of the inventionaccording to certain embodiments of the inventionaccording to certain embodiments of the inventionaccording to certain embodiments of the inventionaccording to certain embodiments of the inventionaccording to certain embodiments of the invention The present invention is explained in more detail by the following examples, which, however, are not limiting:

Modification of the regulatory binding site in the promoter region of the myo-inositol transporter IolT1 by nucleotide substitutions in *C. glutamicum*

*C. glutamicum* ATCC13032 PosiolT1 were constructed according to Niebisch and Bott (2001) (https://doi.org/10.1007/s002030100262) with the vector pK19mobsacB via double homologous recombination (Schafer et al., 1994) (https://doi.org/10.1016/0378-1119(94)90324-7). To this end, in a first step, two PCR products were generated which contained the 5' region upstream of the iolT1 gene (primer: PromiolT1_fw_fw/PromiolT1fw_rev) with the two nucleotides to be exchanged or the 3' region of the gene (primer: Piolt1_rev_fw/Piolt1_rev_rev). 500 base pairs of the flanking regions were amplified in each case for the subsequent homologous recombination. In the second step, the DNA fragments were fused together with the pk19mobsacB vector already cut via restriction endonucleases xBaI and EcoRI by means of Gibson assembly (Gibson et al., 2009) (https://doi.org/10.1038/NMETH.1318). This resulting plasmid pK19mobsacB_P06iolT1 was transformed into *E. coli* DH5a by means of heat shock. Due to the kanamycin resistance gene present on the plasmid, only the clones that had taken up the plasmid could grow. Said clones were checked by means of colony PCR and subsequent gel electrophoresis for the presence of the cloned insert, and its DNA sequence was determined. After isolation of the plasmid, a 150 μL aliquot of electrocompetent *C. glutamicum* cells was thawed on ice, mixed with 1-4.5 μg of plasmid and transferred to a 0.2 cm electroporation cuvette pre-cooled on ice. The mixture was overlaid with 800 μL, 4° C. cold, 10% glycerol (v/v) and electroporated in the electroporator (2500 V, 25 μF, 200 Ω, 2 mm). After electroporation, the mixture was transferred to 4 mL of BHIS medium preheated to 46° C. and was incubated for 6 min at 46° C. The cells were then incubated at 170 rpm for two hours at 30° C. and the suspension was plated onto BHIS-Kan15 agar. The function of the sacB gene was then tested by transferring the clones to BHI-Kan25 agar and to BHI-Kan25 agar with 10% sucrose. In order to be selected for successful excision in a second recombination event, cells cultured on BHI-Kan25 were cultured for approx. 5 h in 5 mL BHI medium, and 100 μl of the culture and a 1:10 dilution were plated onto BHI agar with 10% sucrose. Clones were transferred to BHI-Kan25 agar and BHI agar with 10% sucrose. A colony PCR of the sucrose-resistant and kanamycin-sensitive clones (primer: checkPromiolT1fw/checkPromiolT1 rev) with subsequent DNA sequencing was performed in order to confirm successful nucleotide substitutions.

```
Primers:
PromiolT1_fw_fw:
TGCATGCCTGCAGGTCGACTGAAAAATTGATCAGCAAACACC

PromiolT1fw_rev:
GGCAGACACGATATCCCCCGTCAATCGTACATAGGGAA

Piolt1_rev_fw:
CGGGGGATATCGTGTCTGCCACGATTAAAG piolt1_rev_rev:
TTGTAAAACGACGGCCAGTGGAGTCCAAGAAGCACACG checkPromiolT1fw:
TACGAATGCCCACTTCGCACCCTT checkPromiolT1rev:
CAACTCATTACGGCCAGCCAGTGAGC
```

Modification of the Regulatory Binding Site in the Promoter Region of the Carbohydrate Kinase IolC by Nucleotide Substitutions in *C. glutamicum*

*C. glutamicum* ATCC13032 P$_{O6}$iolT1P$_{O13}$iolC were constructed according to Niebisch and Bott (2001) (https://doi.org/10.1007/s002030100262) with the vector pK19mobsacB via double homologous recombination (Schafer et al., 1994) (https://doi.org/10.1016/0378-1119(94)90324-7). To this end, in a first step, two PCR products were generated which contained the 5' region upstream of the iolC gene (primer: PO13 iolC fw/PO13 iolC rev) with the two nucleotides to be exchanged or the 3' region of the gene (primer: PO13 iolC rev_fw/PO13 iolC rev_rev). 500 base pairs of the flanking regions were amplified in each case for the subsequent homologous recombination. In the second step, the DNA fragments were fused together with the pk19mobsacB vector already cut via restriction endonucleases xBaI and EcoRI by means of Gibson assembly (Gibson et al., 2009) (https://doi.org/10.1038/NMETH.1318). The resulting plasmid pK19mobsacB_PO13iolC was transformed into *E. coli* DH5a by means of heat shock. As a result of the kanamycin resistance gene present on the plasmid, only the clones that had taken up the plasmid could grow. Said clones were checked by means of colony PCR and subsequent gel electrophoresis for the presence of the cloned insert, and its DNA sequence was determined. After isolation of the plasmid, a 150 μL aliquot of electrocompetent *C. glutamicum* ATCC13032 PosiolT1 cells was thawed on ice, mixed with 1-4.5 μg of plasmid, and transferred to a 0.2 cm electroporation cuvette pre-cooled on ice. The mixture was overlaid with 800 μL, 4° C. cold, 10% glycerol (v/v) and electroporated in the electroporator (2500 V, 25 μF, 200 Ω, 2 mm). After electroporation, the mixture was transferred to 4 mL of BHIS medium preheated to 46° C. and was incubated for 6 min at 46° C. The cells were then incubated at 170 rpm for two hours at 30° C. and the suspension was plated onto BHIS-Kan15 agar. The function of the sacB gene was then tested by transferring the clones to BHI-Kan25 agar and to BHI-Kan25 agar with 10% sucrose. In order to be selected for successful excision in a second recombination event, cells cultured on BHI-Kan25 were cultured for approx. 5 h in 5 mL BHI medium, and 100 µl of the culture and a 1:10 dilution were plated onto BHI agar with 10% sucrose. Clones were transferred to BHI-Kan25 agar and BHI agar with 10% sucrose. A colony PCR of the sucrose-resistant and kanamycin-sensitive clones (primer: Check Prom iolC fw/Check Prom iolC_rev) with subsequent DNA sequencing was performed in order to confirm successful nucleotide substitutions.

```
Primers:
PO13 iolC fw:
TGCATGCCTGCAGGTCGACTGGATGCCGTCTTCGAGGC

PO13 iolC rev:
GACCCTCACGATCGCATCCCATGACAATAACAC

PO13 iolC rev_fw:
GGGATGCGATCGTGAGGGTCGCCACATTC

PO13 iolC rev_rev:
TTGTAAAACGACGGCCAGTGCTTGGCTCTTCACTGAAACCAG

Check Prom iolC fw:
TCTCGTTTTCTAGGCGTGCTCCGGG

Check Prom iolC rev:
CGACGGTTCGCACGAGTAGTCA
```

Modification of the Regulatory Binding Site in the Promoter Region of the Carbohydrate Kinase IolC by Nucleotide Substitutions in *C. glutamicum*

*C. glutamicum* ATCC13032 $P_{O6}$iolT1$P_{O5-O9}$iolC were constructed according to Niebisch and Bott (2001) (DOI 10.1007/s002030100262) with the vector pK19mobsacB via double homologous recombination (Schafer et al., 1994) (https://doi.org/10.1016/0378-1119(94)90324-7). To this end, in a first step, two PCR products were generated which contained the 5' region upstream of the encoding region of the iolC gene (primer: PO5-PO9 iolC_fw_fw/PO5 PO9iolC-fw_rev) with the four nucleotides to be exchanged or the 3' end of iolC (primer: PO5-PO9iolC_rev_fw/PO5 PO9iolC_rev_rev). 500 base pairs of the flanking regions were amplified in each case for the subsequent homologous recombination. In the second step, the DNA fragments were fused together with the pk19mobsacB vector already cut via restriction endonucleases xBal and EcoRI by means of Gibson assembly (Gibson et al., 2009) (DOI: 10.1038/NMETH.1318). The resulting plasmid was transformed into *E. coli* DH5 by means of heat shock. As a result of the kanamycin resistance gene present on the plasmid, only the clones that had taken up the plasmid could grow. These were checked by means of colony PCR and subsequent gel electrophoresis for the presence of the moned insert, and its DNA sequence determined. After isolation of the plasmid, a 150 µL aliquot of electrocompetent *C. glutamicum* ATCC13032 $P_{O6}$iolT/cells was thawed on ice, mixed with 1-4.5 µg of plasmid, and transferred to a 0.2 cm electroporation cuvette pre-cooled on ice. The mixture was overlaid with 800 µL, 4° C. cold, 10% glycerol (v/v) and electroporated in the electroporator (2500 V, 25 µF, 200 Ω, 2 mm). After electroporation, the mixture was transferred to 4 mL of BHIS medium preheated to 46° C. and was incubated for 6 min at 46° C. The cells were then incubated at 170 rpm for two hours at 30° C. and the suspension was plated onto BHIS-Kan15 agar. The function of the sacB gene was then tested by transferring the clones to BHI-Kan25 agar and to BHI-Kan25 agar with 10% sucrose. In order to be selected for successful excision in a second recombination event, cells cultured on BHI-Kan25 were cultured for approx. 5 h in 5 mL BHI medium, and 100 µl of the culture and a 1:10 dilution were plated onto BHI agar with 10% sucrose. Clones were transferred to BHI-Kan25 agar and BHI agar with 10% sucrose. A colony PCR of the sucrose-resistant and kanamycin-sensitive clones (primer: PO5-PO9iolC_check_fw/PO5_PO9iolC_check_rev) with subsequent DNA sequencing was performed in order to confirm successful nucleotide substitutions.

```
Primers:
PO5-PO9 iolC_fw_fw:
TGCATGCCTGCAGGTCGACTGGTTGGCGTTTTTGAGGTC

PO5-PO9 iolC_fw_rev:
TAAGTTTCGCTACTCATTCCCTAATGCAAGTGATAATCC
CAGATCAATAAA

PO5-PO9iolC_rev_fw:
GGAATGAGTAGCGAAACTTAGTGAAAAGGGCAGAGTTTG
CAGGTCATAGGGTGCAA

PO5-PO9iolC_rev_rev:
TTGTAAAACGACGGCCAGTGTCCAGCTCAGCAAGCAGG

PO5-PO9iolC_check_fw:
GAGTTTTTCTGCGATGGCGGAACTT

PO5-PO9iolC_check_rev:
GGGGTCTTAAAAGTCTGATCGGTGG
```

Modification of the Regulatory Binding Site in the Promoter Region of the Myo-Inositol Transporter IolT1 by Nucleotide Deletions in *C. glutamicum*

*C. glutamicum* ATCC13032 ΔP$_{O6}$iolT/were constructed according to Niebisch and Bott (2001) (https://doi.org/10.1007/s002030100262) with the vector pK19mobsacB via double homologous recombination (Schafer et al., 1994) (https://doi.org/10.1016/0378-1119(94)90324-7). To this end, in a first step, two PCR products were generated which contained the 5' region upstream of the iolT1 gene (primer: DPO6iolT1_Fw_fw/DPO6iolT1_Fw_rev) with the two deleted nucleotides or the 3' region of the gene (primer: DPO6iolT1_rev_fw/DPO6iolT1_rev_rev). 500 base pairs of the flanking regions were amplified in each case for the subsequent homologous recombination. In the second step, the DNA fragments were fused together with the pk19mobsacB vector already cut via restriction endonucleases xBal and EcoRI by means of Gibson assembly (Gibson et al., 2009) (https://doi.org/10.1038/NMETH.1318). The resulting plasmid pK19mobsacB_Δ PosiolT1 was transformed into *E. coli* DH5a by means of heat shock. As a result of the kanamycin resistance gene present on the plasmid, only the clones that had taken up the plasmid could grow. Said clones were checked by means of colony PCR and subsequent gel electrophoresis for the presence of the cloned insert, and its DNA sequence was determined. After isolation of the plasmid, a 150 µL aliquot of electrocompetent *C. glutamicum* cells was thawed on ice, mixed with 1-4.5 µg of plasmid, and transferred to a 0.2 cm electroporation cuvette pre-cooled on ice. The mixture was overlaid with 800 µL, 4° C. cold, 10% glycerol (v/v) and electroporated in the electroporator (2500 V, 25 µF, 200 Ω, 2 mm). After electroporation, the mixture was transferred to 4 mL of BHIS medium preheated to 46° C. and was incubated for 6 min at 46° C. The cells were then incubated at 170 rpm for two hours at 30° C. and the suspension was plated onto BHIS-Kan15 agar. The function of the sacB gene was then tested by transferring the clones to BHI-Kan25 agar and to BHI-Kan25 agar with 10% sucrose. In order to be selected for successful excision in a second recombination event, cells cultured on BHI-Kan25 were cultured for approx. 5 h in 5 mL BHI medium, and 100 µl of the culture and a 1:10 dilution were plated onto BHI agar with 10% sucrose. Clones were transferred to BHI-Kan25 agar and BHI agar with 10% sucrose. A colony PCR of the sucrose-resistant and kanamycin-sensitive clones (primer: checkPromiolT1fw/checkPromiolT1rev) with subsequent DNA sequencing was performed in order to confirm successful deletion.

```
Primers:
DPO6iolT1_Fw_fw:
TGCATGCCTGCAGGTCGACTAATTGATCAGCAAACACC

DPO6iolT1_Fw_rev:
ATCGTGGCAGACACGATATCCCGTCAATC

DPO6iolT1_rev_fw:
GATATCGTGTCTGCCACGATTAAAGACATTG

DPO6iolT1_rev_rev:
TTGTAAAACGACGGCCAGTGACTGCGAGTCCAAGAAGC checkPromiolT1fw:
TACGAATGCCCACTTCGCACCCTT checkPromiolT1rev:
CAACTCATTACGGCCAGCCAGTGAGC
```

Modification of the Regulatory Binding Site in the Promoter Region of the Carbohydrate Kinase IolC by Nucleotide Deletions in *C. glutamicum*

*C. glutamicum* ATCC13032 $P_{O6}$iolT1 $\Delta P_{O13}$iolC were constructed according to Niebisch and Bott (2001) (https://doi.org/10.1007/s002030100262) with the vector pK19mobsacB via double homologous recombination (Schafer et al., 1994) (https://doi.org/10.1016/0378-1119 (94190324-7). To this end, in a first step, two PCR products were generated which contained the 5' region upstream of the iolC gene (primer: DPO13iolC_fw_fw/ DPO13iolC_fw_rev) with the two deleted nucleotides or the 3' region of the gene (primer: DPO13iolC_rev_fw/ DPO13iolC_rev_rev). 500 base pairs of the flanking regions were amplified in each case for the subsequent homologous recombination. In the second step, the DNA fragments were fused together with the pk19 mobsacB vector already cut via restriction endonucleases xBaI and EcoRI by means of Gibson assembly (Gibson et al., 2009) (https://doi.org/10.1038/NMETH.1318). The resulting plasmid pK19mobsacB_Δ $P_{O13}$iolC was transformed into *E. coli* DH5a by means of heat shock. As a result of the kanamycin resistance gene present on the plasmid, only the clones that had taken up the plasmid could grow. Said clones were checked by means of colony PCR and subsequent gel electrophoresis for the presence of the cloned insert, and its DNA sequence was determined. After isolation of the plasmid, a 150 µL aliquot of electrocompetent *C. glutamicum* ATCC13032 $P_{O6}$iolT1 cells was thawed on ice, mixed with 1-4.5 µg of plasmid, and transferred to a 0.2 cm electroporation cuvette pre-cooled on ice. The mixture was overlaid with 800 µL, 4° C. cold, 10% glycerol (v/v) and electroporated in the electroporator (2500 V, 25 µF, 200 Ω, 2 mm). After electroporation, the mixture was transferred to 4 mL of BHIS medium preheated to 46° C. and was incubated for 6 min at 46° C. The cells were then incubated at 170 rpm for two hours at 30° C. and the suspension was plated onto BHIS-Kan15 agar. The function of the sacB gene was then tested by transferring the clones to BHI-Kan25 agar and to BHI-Kan25 agar with 10% sucrose. In order to be selected for successful excision in a second recombination event, cells cultured on BHI-Kan25 were cultured for approx. 5 h in 5 mL BHI medium, and 100 µl of the culture and a 1:10 dilution were plated onto BHI agar with 10% sucrose. Clones were transferred to BHI-Kan25 agar and BHI agar with 10% sucrose. A colony PCR of the sucrose-resistant and kanamycin-sensitive clones (primer: Check Prom iolC fw/Check Prom iolC rev) with subsequent DNA sequencing was performed in order to confirm successful deletion.

```
Primers:
DPO13iolC_fw_fw:
TGCATGCCTGCAGGTCGACTCCGTCTTCGAGGCGTTGG

DPO13iolC_fw_rev:
GTGGCGACCCTCACGATCGCATCCCATG

DPO13iolC_rev_fw:
GCGATCGTGAGGGTCGCCACATTCCATC

DPO13iolC_rev_rev:
TTGTAAAACGACGGCCAGTGCGCGGCTTGGCTCTTCAC

Check Prom iolC fw:
TCTCGTTTTCTAGGCGTGCTCCGGG

Check prom iolC_rev:
CGACGGTTCGCACGAGTAGTCA
```

Modification of the Regulatory Binding Site in the Promoter Region of the Carbohydrate Kinase IolC by Nucleotide Deletions in *C. glutamicum*

*C. glutamicum* ATCC13032 PosiolT1 $\Delta P_{O5\text{-}O9}$iolC were constructed according to Niebisch and Bott (2001) (https://doi.org/10.1007/s002030100262) with the vector pK19mobsacB via double homologous recombination (Schafer et al., 1994) (https://doi.org/10.1016/0378-1119 (94)90324-7). To this end, in a first step, two PCR products were generated which contained the 5' region upstream of the iolC gene (primer: ΔPO5-PO9iolC_fw_fw/ΔPO5-PO9iolC_fw_rev) with the two deleted nucleotides or the 3' region of the gene (primer: APO5 PO9iolC_rev_fw/APO5 PO9iolC_rev_rev). 500 base pairs of the flanking regions were amplified in each case for the subsequent homologous recombination. In the second step, the DNA fragments were fused together with the pk19mobsacB vector already cut via restriction endonucleases xBaI and EcoRI by means of Gibson assembly (Gibson et al., 2009) (https://doi.org/10.1038/NMETH.1318). The resulting plasmid pK19mobsacB_Δ $P_{O5\text{-}O9}$iolC was transformed into *E. coli* DH5a by means of heat shock. As a result of the kanamycin resistance gene present on the plasmid, only the clones that had taken up the plasmid could grow. Said clones were checked by means of colony PCR and subsequent gel electrophoresis for the presence of the cloned insert, and its DNA sequence was determined. After isolation of the plasmid, a 150 µL aliquot of electrocompetent *C. glutamicum* ATCC13032 PosiolT1 cells was thawed on ice, mixed with 1-4.5 µg of plasmid, and transferred to a 0.2 cm electroporation cuvette pre-cooled on ice. The mixture was overlaid with 800 µL, 4° C. cold, 10% glycerol (v/v) and electroporated in the electroporator (2500 V, 25 µF, 200 Ω, 2 mm). After electroporation, the mixture was transferred to 4 mL of BHIS medium preheated to 46° C. and was incubated for 6 min at 46° C. The cells were then incubated at 170 rpm for two hours at 30° C. and the suspension plated onto BHIS-Kan15 agar. The function of the sacB gene was then tested by transferring the clones to BHI-Kan25 agar and to BHI-Kan25 agar with 10% sucrose. In order to be selected for successful excision in a second recombination event, cells cultured on BHI-Kan25 were cultured for approx. 5 h in 5 mL BHI medium, and 100 µl of the culture and a 1:10 dilution were plated onto BHI agar with 10% sucrose. Clones were transferred to BHI-Kan25 agar and BHI agar with 10% sucrose. A colony PCR of the sucrose-resistant and kanamycin-sensitive clones (primer: Check ΔPO5-PO9iolC_fw/Check ΔPO5-PO9iolC_rev) with subsequent DNA sequencing was performed in order to confirm successful deletion.

```
ΔPO5-PO9iolC_fw_fw:
TGCATGCCTGCAGGTCGACTGGTTGGCGTTTTTGAGGTC

ΔPO5-PO9iolC_fw_rev:
TAAGTTTCGCTACTCATTCCCTAATGCAAGTGATAATCAGAT-
CAATAAAAGCCCTGGAT ΔPO5-PO9iolC_rev_fw:
GGAATGAGTAGCGAAACTTAGTGAAAAGGGCAGAGTTT-
GCAGGTCATAGTGCAACTTTGTTAACCC ΔPO5-PO9iolC_rev_rev:
TTGTAAAACGACGGCCAGTGTCCAGCTCAGCAAGCAGG Check APO5-PO9iolC_fw:
GAGTTTTTCTGCGATGGCGGAACTT Check APO5-PO9iolC rev:
GGGGTCTTAAAAGTCTGATCGGTGG
```

Deletion of D-Xylose Dehydrogenase IolG in *C. glutamicum*

*C. glutamicum* ATCC13032 ΔiolG were constructed according to Niebisch and Bott (2001) (https://doi.org/10.1007/s002030100262) with the vector pK19mobsacB via double homologous recombination (Schafer et al., 1994) (https://doi.org/10.1016/0378-1119(94)90324-7). To this end, in a first step, two PCR products were generated containing the 5' region of the iolG gene (primer: iolG front fw/iolG front rev) with the first three codons or the 3' region (primer: iolG back fw/iolG back rev) with the last six codons of the iolG gene. 500 base pairs of the flanking regions were amplified in each case for the subsequent homologous recombination. In the second step, the DNA fragments were fused together with the pk19mobsacB vector already cut via restriction endonucleases xBal and EcoRI by means of Gibson assembly (Gibson et al., 2009) (https://doi.org/10.1038/NMETH.1318). The resulting plasmid pK19mobsacB_ΔiolG was transformed into *E. coli* DH5a by means of heat shock. As a result of the kanamycin resistance gene present on the plasmid, only the clones that had taken up the plasmid could grow. Said clones checked by means of colony PCR and subsequent gel electrophoresis for the presence of the cloned insert, and its DNA sequence was determined. After isolation of the plasmid, a 150 µL aliquot of electrocompetent *C. glutamicum* cells was thawed on ice, mixed with 1-4.5 µg of plasmid, and transferred to a 0.2 cm electroporation cuvette pre-cooled on ice. The mixture was overlaid with 800 µL, 4° C. cold, 10% glycerol (v/v) and electroporated in the electroporator (2500 V, 25 µF, 200 Ω, 2 mm). After electroporation, the mixture was transferred to 4 mL of BHIS medium preheated to 46° C. and was incubated for 6 min at 46° C. The cells were then incubated at 170 rpm for two hours at 30° C. and the suspension plated onto BHIS-Kan15 agar. The function of the sacB gene was then tested by transferring the clones to BHI-Kan25 agar and to BHI-Kan25 agar with 10% sucrose. In order to be selected for successful excision in a second recombination event, cells cultured on BHI-Kan25 were cultured for approx. 5 h in 5 mL BHI medium, and 100 µl of the culture and a 1:10 dilution were plated onto BHI agar with 10% sucrose. Clones were transferred to BHI-Kan25 agar and BHI agar with 10% sucrose. A colony PCR of the sucrose-resistant and kanamycin-sensitive clones (primer: check iolG fw/check iolG rev) with subsequent gel electrophoresis was performed in order to confirm successful deletion.

```
Primers:
iolG front fw:
TGCATGCCTGCAGGTCGACTGAAGAGTTCGGCATGAAGC iolG front rev:
TACTCCCGGGCATATGGCGAAGGCTCTTGCTCAT iolG back fw:
GAGCCTTCGCCATATGCCCGGGAGTACTGGATCCGTTGATGCGGCAC-
CTCGC iolG back rev:
TTGTAAAACGACGGCCAGTGATGACTCGCCATGCTTCAATACC check iolG fw:
CGACGTTGCTGGTCTTGCTTCCAAG check iolG rev:
GGTTAGTGATGTAGCGCAGGCCGTG
```

Chromosomal Integration of D-Xylose Dehydrogenase IolG in *C. glutamicum*

The various *C. glutamicum* integration mutants *C. glutamicum* ATCC13032 iolG$^1$, *C. glutamicum* ATCC13032 iolG$^2$, *C. glutamicum* ATCC13032 iolG$^3$ were constructed according to Niebisch and Bott (2001) (https://doi.org/10.1007/s002030100262) with vectors in each case based on pK19mobsacB via double homologous recombination (Schafer et al., 1994) (https://doi.org/10.1016/0378-1119 (94)90324-7). To this end, in a first step, PCR products containing the flanking regions of the various integration loci, the constitutional promoter Tuf, and the gene iolG were generated (primer: NCS_PTuf_fw/NCS_PTuf_rev/NCS_P-tuf_iolG_fw/NCS_Ptuf_iolG_rev/CgLP4_fw_fw/ CgLP4_fw_rev/CgLP4_PTuf_fw/CgLP4_PTuf_rev/ CgLP4_iolG_fw/CgLP4_iolG_rev/CgLP4_rev_fw/ CgLP4_rev_rev/CgLP12_fw_fw/CgLP12_fw_rev/ CgLP12_PTuf_fw/CgLP12_PTuf_rev/CgLP12_iolG_fw/ CgLP12_iolG_rev/CgLP12_rev_fw/CgLP12_rev_rev). In the second step, the DNA fragments were fused together with the pk19mobsacB vectors already cut via restriction endonucleases xBal and EcoRI by means of Gibson assembly in each case (Gibson et al., 2009) (https://doi.org/10.1038/NMETH.1318). The resulting plasmids pk19mobsacB ncr cons P$_{Tuf}$iolG, pk19mobsacB CgLP4 P$_{Tuf}$iolG, and pk19mobsacB CgLP12 P$_{Tuf}$iolG were transformed into *E. coli* DH5a by means of heat shock. As a result of the kanamycin resistance gene present on the deconstructed plasmids, only the clones that had taken up the plasmid could grow. Said clones were checked by means of colony PCR and subsequent gel electrophoresis for the presence of the cloned insert, and its DNA sequence was determined. After isolation of the plasmid, a 150 µL aliquot of electrocompetent *C. glutamicum* cells was thawed on ice, mixed with 1-4.5 µg of the plasmid to be transformed in each case, and transferred to a 0.2 cm electroporation cuvette pre-cooled on ice. The mixture was overlaid with 800 µL, 4° C. cold, 10% glycerol (v/v) and electroporated in the electroporator (2500 V, 25 μF, 200 Ω, 2 mm). After electroporation, the mixture was transferred to 4 mL of BHIS medium preheated to 46° C. and was incubated for 6 min at 46° C. The cells were then incubated at 170 rpm for two hours at 30° C. and the suspension plated onto BHIS-Kan15 agar. In each case, the function of the sacB gene was tested by transferring the clones to BHI-Kan25 agar and to BHI-Kan25 agar with 10% sucrose. In order to be selected for successful excision in a second recombination event, cells cultured on BHI-Kan25 were cultured for approx. 5 h in 5 mL BHI medium, and 100 μl of the culture and a 1:10 dilution were plated onto BHI agar with 10% sucrose. Clones were transferred to BHI-Kan25 agar and BHI agar with 10% sucrose. A colony PCR of the sucrose-resistant and kanamycin-sensitive clones (primer: NCS check fw/NCS check rev/CgLP4_Check_fw/CgLP4_Check_rev/CgLP12_Check_fw/CgLP12_Check_rev) with subsequent DNA sequencing was performed in order to confirm the successful integration in each case.

```
Primers:
NCS_PTuf_fw:
TTTAAATTGTGTCCATGAGGCACAGGGTAGCTGGTAGTTTG

NCS_PTuf_rev:
TCTTGCTCATACGCGTTCCTCCTGGACTTC

NCS_Ptuf_iolG_fw:
AGGAACGCGTATGAGCAAGAGCCTTCGC

NCS_Ptuf_iolG_rev:
CGAAGCATATGCCCGGGAGTTTAAGCGTAGAAATCTGGGC

NCS check fw:
CGGAATGATCTTGACCCTTGTTGGTG

NCS check rev:
ATCAAGCAGATCTCTGAGCTGCTGGC

CgLP4_fw_fw:
TGCATGCCTGCAGGTCGACTCTTCTGGGTCGGCGATAC

CgLP4_fw_rev:
CTACCCTGTGCATCAAAAAATCCGCCGTTC

CgLP4_PTuf_fw:
TTTTTTGATGCACAGGGTAGCTGGTAGTTTG

CgLP4_PTuf_rev:
TCTTGCTCATACGCGTTCCTCCTGGACTTC

CgLP4_iolG_fw:
AGGAACGCGTATGAGCAAGAGCCTTCGC

CgLP4_iolG_rev:
CTCACTTAGTTTAAGCGTAGAAATCTGGGC

CgLP4_rev_fw:
CTACGCTTAAACTAAGTGAGTTTGGATG

CgLP4_rev_rev:
TTGTAAAACGACGGCCAGTGTAGTACGCGGATAAATGATC

CgLP4_Check_fw:
TGCAGGTCACTGTGGAAAATCG

CgLP4_Check_rev:
AATCAGCATCACCCATCCCTTCAC

CgLP12_fw_fw:
TGCATGCCTGCAGGTCGACTCGTTGAAGACTCCGTCAAAC

CgLP12_fw_rev:
CTACCCTGTGATATGCCGATTGCAAGAAAC

CgLP12_PTuf_fw:
ATCGGCATATCACAGGGTAGCTGGTAGTTTG

CgLP12_PTuf_rev:
TCTTGCTCATACGCGTTCCTCCTGGACTTC

CgLP12_iolG_fw:
AGGAACGCGTATGAGCAAGAGCCTTCGC

CgLP12_iolG_rev:
ATTTTTTGACTGATTAAGCGTAGAAATCTGGGC

CgLP12_rev_fw:
CTACGCTTAATCAGTCAAAAAATGTTGAAATCAG

CgLP12_rev_rev:
TTGTAAAACGACGGCCAGTGTTGGCGCTTCTTTGAAGAG

CgLP12_Check_Fw:
CTCAAGGTCATCCGTGAAATGTGGC

CgLP12_Check_Rev:
TTGGCTTTCCATGCTTTGAGGACT
```

Plasmid-Based Expression of D-Xylose Dehydrogenase IolG in *C. glutamicum*

In the first step to isolate genomic DNA, *C. glutamicum* cells were disrupted by suspension in 50 μL of 2% DMSO and subsequent incubation for 5 minutes at 95° C. Cell debris was centrifuged for 1 min at 11,000 rpm and 3 μL of supernatant was used as a template for the amplification of iolG (primer: p3_iolG_fw/p3_iolG_rev). This amplificate was fused together with the pEKEx3 vector already cut via restriction endonucleases pstI and EcoRI in the Gibson assembly (Gibson et al., 2009) (https://doi.org/10.1038/NMETH.1318). The resulting plasmid pEKEx3 iolG was transformed into *E. coli* DH5a by means of heat shock. As a result of the spectinomycin resistance gene mediated by the plasmid, only the clones that had taken up the plasmid could grow. Said clones checked by means of colony PCR and subsequent gel electrophoresis for the presence of the cloned insert, and its DNA sequence was determined. After isolation of the plasmid, a 150 μL aliquot of electrocompetent *C. glutamicum* cells was thawed on ice, mixed with 1-4.5 μg of plasmid, and transferred to a 0.2 cm electroporation cuvette pre-cooled on ice. The mixture was overlaid with 800 μL, 4° C. cold, 10% glycerol (v/v) and electroporated in the electroporator (2500 V, 25 μF, 200 Ω, 2 mm). After electroporation, the mixture was transferred to 4 mL of BHIS medium preheated to 46° C. and was incubated for 6 min at 46° C. The cells were then incubated at 170 rpm for two hours at 30° C. The suspension was plated onto BHI-Spc100 agar.

```
Primers:
p3_iolG_fw:
GCCAAGCTTGCATGCCTGCAGCTAGTATAAGGAGATATAGATAT-
GAGCAAGAGCCTTCGC p3_iolG_rev:
CTGTAAAACGACGGCCAGTGTTAAGCGTAGAAATCTGGGC
```

Medium and Cultivation Conditions

Complex brain heart infusion medium (BD DIFCO™ BRAIN HEART INFUSION AGAR (BHI), a general purpose medium that can be used for aerobic bacteriology, DIFCO™ Laboratories, Detroit, USA) and defined CGXII medium was used to culture *C. glutamicum* strains. The CGXII medium contained the following composition per liter of deionized water: 1 g $K_2HPO_4$, 1 g $KH_2PO_4$, 5 g urea, 13.25 mg $CaCl_2 \cdot 2\ H_2O$, 0.25 g $MgSO_4\ 7H_2O$, 10 mg $FeSO_4$ $7H_2O$, 10 mg $MnSO_4 \cdot H_2O$, 0.02 mg $NiCl_2\ 6H_2O$, 0.313 mg $CuSO_4 \cdot 5\ H_2O$, 1 mg $ZnSO_4\ 7H_2O$, 0.2 mg biotin, 3,4-dihydroxybenzoate, 0.02% (v $v^{-1}$) antifoam AF204. Spectinomycin and isopropyl β-D-thiogalactosides (IPTG) were added to final concentrations of 100 μg $mL^{-1}$ or 1 mmol $L^{-1}$ for the cultivation of strains with the expression vector pEKEx3. All chemicals were purchased from SIGMA ALDRICH™ (Steinheim, Germany). First, precultures were inoculated onto BHI medium in test tubes from single colonies and incubated for 8 h at 30° C. on a rotary shaker at 170 rpm. From this culture, a second preculture was then inoculated in 500 mL shake flasks with 50 mL of defined CGXII medium and 10 $gL^{-1}$ D-glucose and 30 $gL^{-1}$ D-xylose as the carbon and energy source and incubated for 15 h at 30° C. on a rotary shaker at 130 rpm. The main culture was then inoculated onto a $OD_{600}$ of 1 in 50 mL of defined CGXII medium with 10 $gL^{-1}$ D-glucose and 30 $gL^{-1}$ D-xylose as the carbon and energy source and incubated for 56 h at 30° C. on a rotary shaker at 130 rpm. Samples were taken from the main culture to measure the concentrations of biomass, D-xylose, and D-xylonate.

Preparation of Bagasse Hydrolysate

Defined CGXII medium and pretreated bagasse hydrolyzate were used to produce D-xylonate by means of batch and fed batch processes. The pretreatment of ground bagasse (0.25-1 cm) was carried out by incubation in 0.1 mol $L^{-1}$ $H_2SO_4$ at 121° C. The subsequent hydrolysis was carried out in a parallel bioreactor system (EPPENDORF™/DASGIP™, Julich, Germany) with a working volume of 600 mL and a solution consisting of 180 g of pretreated bagasse, 50 mM $C_2H3NaO_2$ and 10.4 mL of CELLIC® CTeC2 enzyme mix, an enzyme blend composed of cellulases, β-glucosidase, and a hemicellulase (NOVOZYMES™, Bagsvserd, Denmark). The pH was adjusted to pH 5 by means of KOH and the hydrolysis was carried out at 50° C. for 72 h at constant stirrer speed (400 rpm). 8 g $NH_4Cl$ and 2 g $K_2HPO_4$ were then dissolved in 200 mL deionized water and added to the hydrolyzate. The medium was then adjusted for culturing purposes to pH 7 by 5 M $NH_4OH$. Some media components (D-glucose, D-xylose, PCA, trace elements, AF204) were added sterilely after autoclaving. In the case of the fed batch process, a solution of 100 g of $L^{-1}$ D-glucose in deionized water was used.

During cultivation, the pH was regulated bilaterally to pH 7 by feeding in 5 M $H_3PO_4$ and 5 M $NH_4OH$, respectively. The temperature and aeration rate were fixed at 30° C. and 0.5 vvm, respectively. Aerobic process conditions (>30% dissolved oxygen concentration) were assured by controlling the stirrer speed (400-1,200 rpm). Measurements were made online for pH (405 DPAS SC K80/225, a pressurized gel-filled pH electrode, METTLER TOLEDO™) DO (VISIFERM™ DO 225, a sensor for the measurement of dissolved oxygen, HAMILTON). and exhaust gas composition (DASGIP® GA4, an exhaust analsyer, EPPENDORF™ AG). A preculture growing exponentially on CGXII medium (20 $gL^{-1}$ D-glucose) was inoculated onto a final OD of 2. Samples were taken from the main culture to measure the concentrations of biomass, D-xylose, and D-xylonate.

Towards the end of the fermentation, D-xylonate can be isolated from the cultivation solution according to known protocols and/or prepared, i.e., separated, purified, and/or concentrated. For product purification, an existing protocol (Liu et al., Bioresource Technology, 2012, 115: 244-248) was used as follows: 1. Cell separation by means of centrifugation (4500 rpm for 10 min at 4° C.); 2. Decolorization of the resulting supernatant in activated carbon (AC); 3. Filtration of AC-treated supernatant (0.22 μm) and concentration by means of rotary evaporator (100 mbar, 60° C. water bath); 4. Filtration of the concentrate (0.22 μm) and precipitation of D-xylonate by addition of EtOH (3:1, v/v); vacuum drying of the product for at least 12 h at −10° C.

The biomass was determined gravimetrically by transferring 2 mL of culture supernatant to a weighed test tube, centrifuging at 13,000 rpm for 10 min and resuspending in 0.9% (w $v^{-1}$) NaCl. After a further centrifugation step, the supernatant was removed by means of decanting. The cell pellet was dried at 80° C. for 24 h, followed by gravimetric cell dry weight determination. For substrate and product quantification, the supernatants were filtered by means of a cellulose acetate syringe filter (0.2 μm, DIA-NIELSEN, Duren, Germany). D-glucose and D-xylonate were separated by an isocratic exchange process in HPLC (AGILENT 1100 INFINITY, a high performance liquid chromatography instrument, AGILENT TECHNOLOGIES™, Santa Clara, CA). The process uses an organic resin HPLC column 300×8 mm (DIA-NIELSEN, Duren, Germany) as a stationary phase, 0.1 M $H_2SO_4$ with a flow rate of 0.6 mL $min^{-1}$ in the form of a mobile phase, a column temperature of 80° C., and an injection volume of 10 μL. D glucose was detected by means of refractive index detector at 35° C. D-xylonate was detected by means of UV light absorption at 215 nm with a diode array detector. Corresponding concentration values were determined by means of external standards and weighted linear regression. An enzymatic assay (Xylose Assay Kit, MEGAZYME™, Wickow, Ireland) was used for the quantification of D-xylose. All pipetting steps were performed using an automated liquid handling system (FREEDOM EVO™ 200, TECAN™ Group Ltd., Männedorf, Switzerland). The increase in NADH was measured at 340 nm by plate reader (INFINITE™ M200, TECAN™ Group Ltd., Männedorf, Switzerland).

Isolation of the D-Xylose Dehydrogenase IolG According to an Embodiment of the Invention Plasmid pET-28b-iolG was transformed into *Escherichia coli* BL21 for heterologous gene expression of iolG and then cultured in 2×50 mL of TerrificBroth (TB) medium with 50 mg/L kanamycin for 16 hours at 30° C. and 250 rpm. 10 mL each of these cultures was used to inoculate four bioreactor cultures with 20 g/L glycerol as initial carbon source and 50 mg/L kanamycin to maintain selection pressure. The bioreactor cultures were heated to 30° C. and the pH was titrated to pH 7 with ammonia water. Approximately 5 h after cultivation start, gene expression was induced by the addition of 250 μM isopropyl-β-D-thiogalactopyranoside (IPTG), and again after approx. 32 h. After complete metabolization of the initial glycerol amount, a concentrated substrate solution with 700 g/L glycerol and 20 g/L $MgSO_4*7H_2O$ was metered in automatically at a rate of 20 mL/h, based on a 2-point controller (on: DO>30%, off: DO<10%). After approx. 10 hours of feed phase, the cultures were harvested and the cells were separated from the culture medium by centrifugation (8000 rpm) for 20 minutes. The cell mass was stored at −20° C.

Approx. 60 g cell mass was resuspended in 150 mL equilibration buffer (50 mMTris-HCl, 2 mM $MgSO_4$, 300 mM NaCl, pH 7.0) on ice for 30 min. The cell suspension was solubilized in a rotary cooling cell using an ultrasound probe (ultrasound processor UP 200S Dr. Hielscher S14D sonotrode, cycle 0.5 amplitude 70) for 30 min. After centrifugation (23000 rpm, 4° C., 35 min), the solubilized supernatant was given up via an Ni-NTA column (column volume 70 mL, flow 6 mL/min) (washing buffer: 50 mMTris pH 7.5, 300 mM NaCl, 2 mM $MgSO_4$ 25 mM imidazole;

elution buffer: 50 MMTris pH 8.0, 300 mM NaCl, 2 mM MgSO$_4$, 250 mM imidazole). The eluate was collected in fractions of 60 ml in total and desalinated through a SEPHADEX™ G25, a gel filtration resin for desalting and buffer exchange, column, (column volume 960 mL, flow 10 mL/min, desalination buffer: 10 mMTris pH 7.6, 2 mM MgSO$_4$), of which a total of 150 mL were collected as protein-containing fractions and lyophilized. The resulting lyophilizate had a protein content of 60% according to Bradford protein determination.

Determination of D-Xylose Dehydrogenase Activity

The enzyme tests for the activity determination of IolG lyophilizate were carried out in a total volume of 200 µL. The enzymatic reactions were carried out by rapid addition of 180 µL of reaction mix (250 mM Tris-HCl, 22 mM NAD$^+$, 5 mM MgCl$^2$, and 125 µL/mL IolG lyophilizate solution at 2.5 mg/L, pH7.5, >30 min preheated to 30° C.) to 20 µL of presented substrate solution (0-250 mM [0-25 mM final per reaction volume] of D-xylose or myo-inositol). Extinction growth was measured at 340 nm in the microtiter plate reader (preheated for >30 min to 30° C.) for approx. 20 min. After a brief transient response of all measurement signals, the initial reaction rates were determined by means of linear regression over a period of 2 min. The resulting increases in the unit [absorption units per minute] were determined in the NADH formation rate in the unit [mM NADH per minute] by calibration of the absorption signal via standard solutions with known NADH concentration instead of substrate solutions, using Gaussian error propagation taking into account the calibration parameter covariance matrix. The enzyme shows no activity with respect to the myo-inositol substrate.

In order to determine the maximum enzyme activity (Vmax) and the specific substrate affinity (Km) with respect to D-xylose, the experimental data were fitted to Michaelis Menten kinetics by means of non-linear regression. The enzyme kinetic parameters from the experiments were determined to be Vmax=18.8±3.3 U/L and Km=28.0±7.1.

D-Xylonate Formation in the Homologous Host System of Coryneform Bacteria by Enhanced Expression of the D-Xylose Dehydrogenase According to Certain Embodiments of the Invention Experiments on growth, D-xylose uptake, and D-xylonate formation of different variants of coryneform bacterial strains compared to wild type were carried out in shake flasks in defined CGXII medium with 10 gL$^{-1}$ D-glucose and 30 gL$^{-1}$ D-xylose. The following examples clearly show that the D-xylose dehydrogenase activity according to certain embodiments of the invention is responsible for D-xylonate formation in coryneform bacteria FIGS. 14 and 15.

Figure 14:
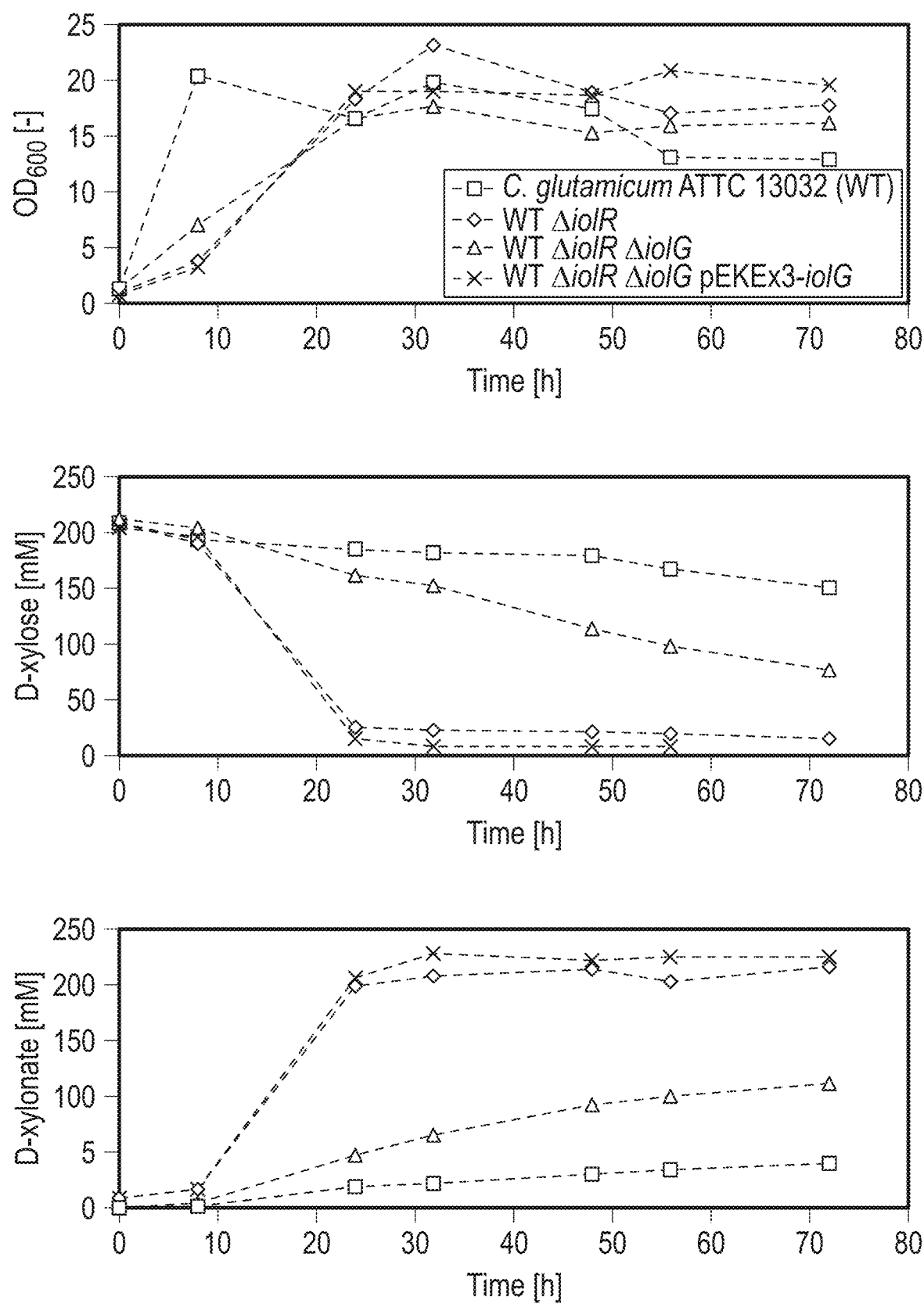
FIGS. 14 and 15 show growth, D-xylose uptake and accumulation, and the D-xylonate formation of different variants of coryneform bacterial strains.

As shown in FIG. 14, all strains show comparable growth on D-glucose as a carbon and energy source. The wild-type strain *C. glutamicum* ATCC13032 has a very low uptake of D-xylose and conversion to D-xylonate. The maximum D-xylonate titer after 72 h is 40.0 mM here. The strain *C. glutamicum* WT ΔiolR with deletion of the gene for the regulator IolR shows a markedly increased D-xylose uptake and D-xylonate production due to the deregulated expression of the D-xylose transporter IolT1 and the D-xylose dehydrogenase IolG. The maximum D-xylonate titer after 72 h is 214.7 mM here. The strain *C. glutamicum* WT ΔiolR ΔiolG, with additional deletion of the gene for the D-xylose dehydrogenase IolG according to certain embodiments of the invention, shows a greatly reduced D-xylose uptake and D-xylonate formation due to the lack of expression of the D-xylose dehydrogenase IolG. The maximum D-xylonate titer after 72 h is 111.9 mM here. The strain *C. glutamicum* WT ΔiolR ΔiolGpEKEx3-iolG, with additional plasmid-based expression of the gene for the D-xylose dehydrogenase IolG according to certain embodiments of the invention, shows the highest D-xylonate production due to the high homologous expression of the D-xylose dehydrogenase IolG, which overcompensates the non-expression (ΔiolG). The maximum D-xylonate titer after 72 h is 223.6 mM here.

Figure 15:
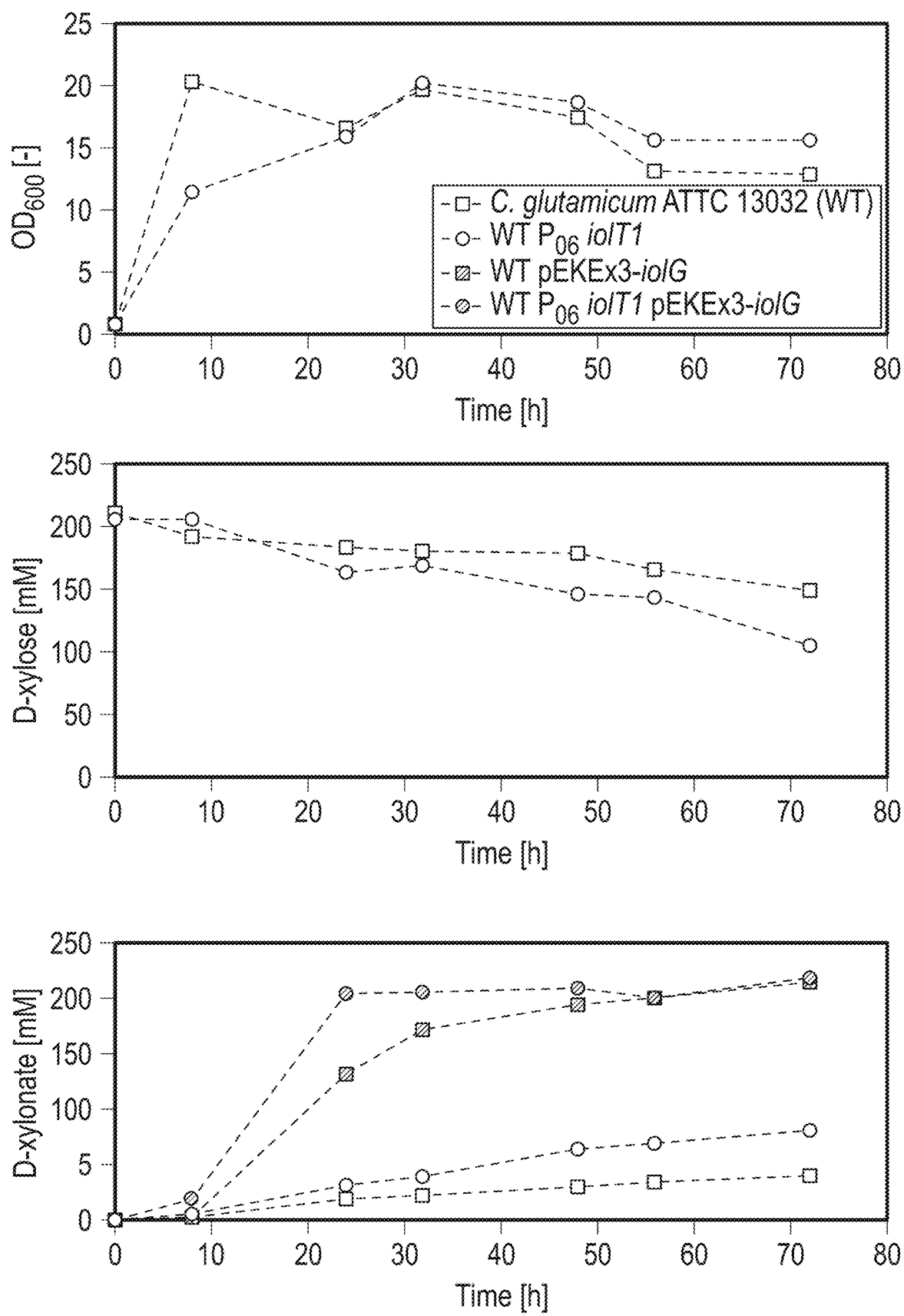

FIG. 15 shows the D-xylonate formation of further variants of coryneform bacterial strains according to certain embodiments of the invention, in which the functionality of operatively linked regulatory regions of the nucleic acid sequence encoding the D-xylose dehydrogenase according to certain embodiments of the invention is changed. The experiments were carried out in shake flasks in defined CGXII medium with 10 gL$^{-1}$ D-glucose and 30 gL$^{-1}$ D-xylose.

The wild-type strain *C. glutamicum* ATC13032 has a very low uptake of D-xylose and conversion to D-xylonate. The maximum D-xylonate titer after 72 h is 40.0 mM here. The strain *C. glutamicum* WT PosiolT1 with modified promoter sequence in the gene region of the D-xylose transporter IolT1 shows slightly increased D-xylose uptake and D-xylonate production due to the deregulated expression of the D-xylose transporter IolT1. The maximum D-xylonate titer after 72 h is 80.0 mM here.

The strain *C. glutamicum* WTpEKEx3-iolG with plasmid-based expression of the gene for D-xylose dehydrogenase shows significantly increased D-xylonate production due to the homologous expression of D-xylose dehydrogenase IolG. The maximum D-xylonate titer after 72 h is 213.9 mM here. The strain *C. glutamicum* WT PosiolT1pEKEc3-iolG, with additional modified promoter sequence in the gene region of the D-xylose transporter iolT1, shows the highest D-xylonate production due to the simultaneous homologous expression of the D-xylose dehydrogenase IolG and the deregulated expression of the D-xylose transporter iolT1. The maximum D-xylonate titer after 72 h is 217.4 mM here.

Figure 16:
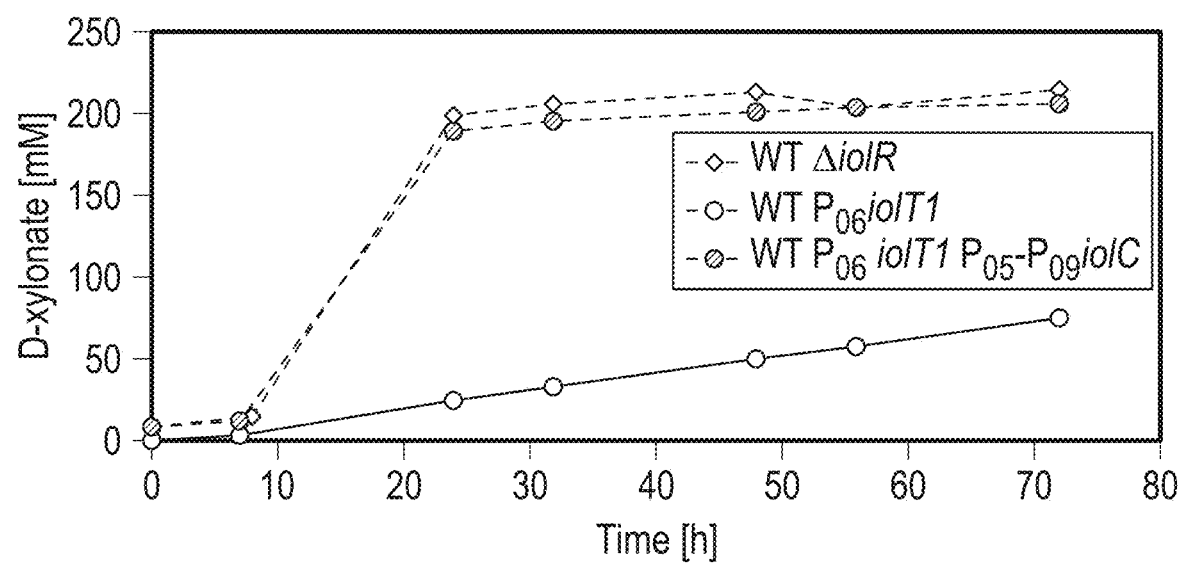
FIG. 16 shows the D-xylonate formation of different variants of coryneform bacterial strains.
Figure 17:
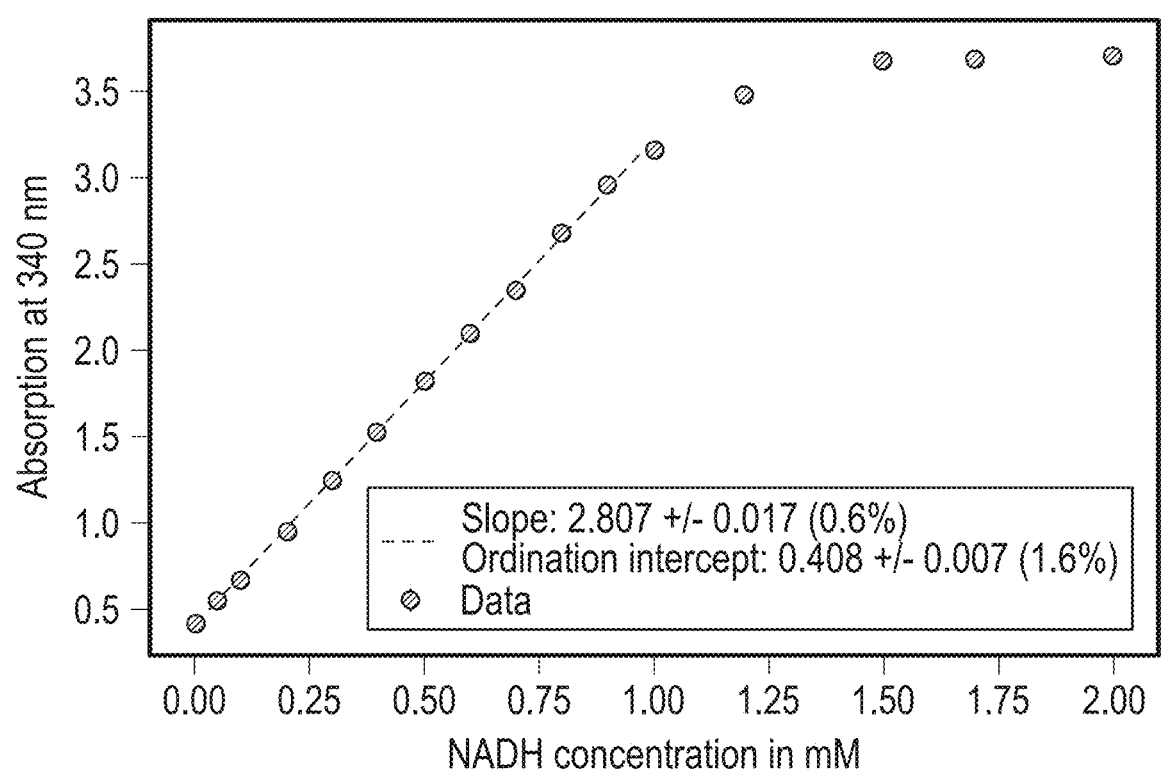
FIG. 17 shows the calibration of the absorption signal at 340 nm in the kinetic assay with respect to NADH concentration in mM (blue dots). The valid calibration was set to the range 0 to 1 mM NADH and the corresponding regression line (dashed red line) with associated parameters, their values and errors were plotted.
Figure 18:
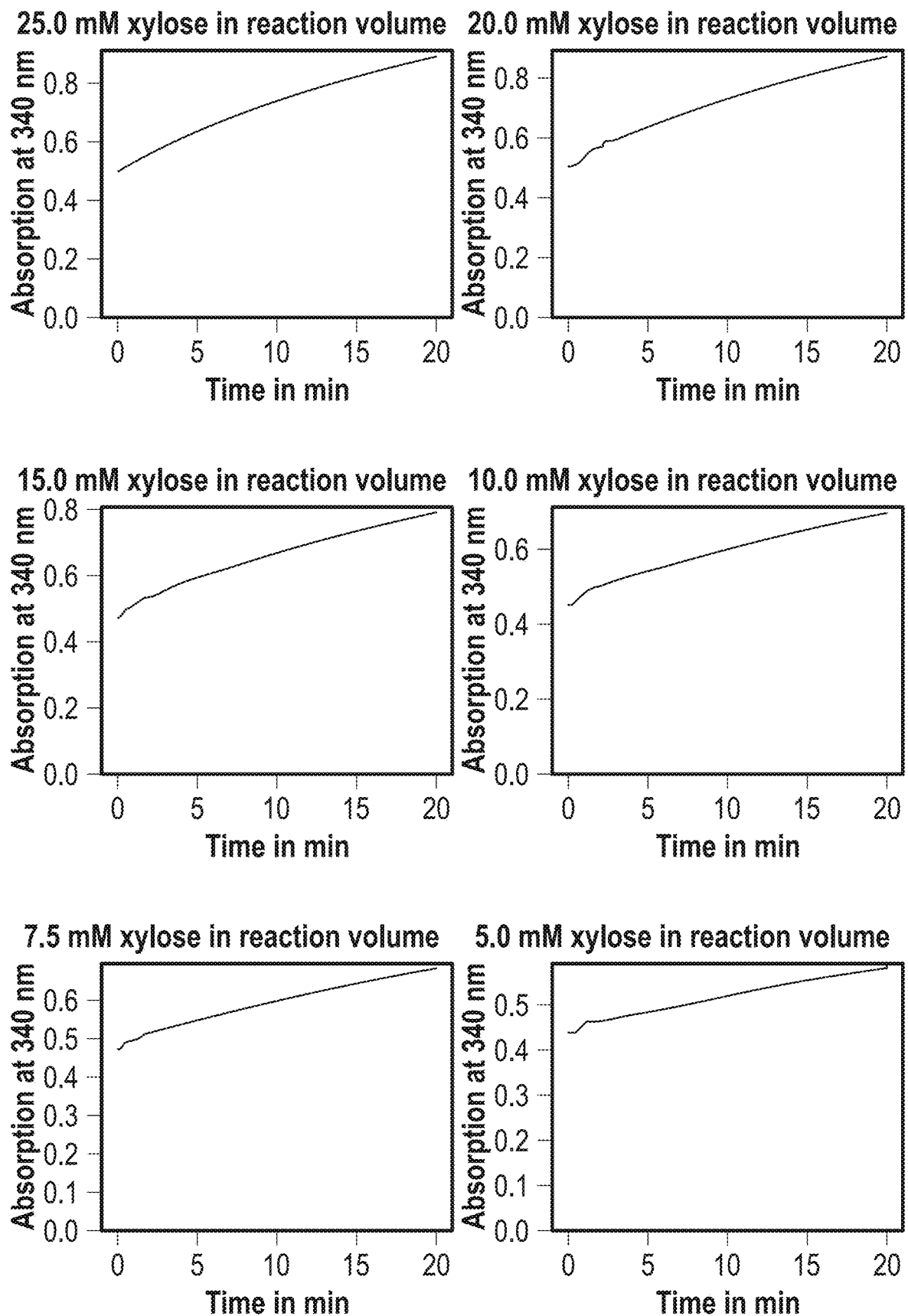
FIG. 18 shows conversion curves for the D-xylose dehydrogenase IolG according to certain embodiments of the invention with D-xylose as substrate, for various concentrations of D-xylose used (25 mM top left to 1 mM bottom right). The absorption measurements recorded are shown for a period of 20 minutes.
Figure 18:
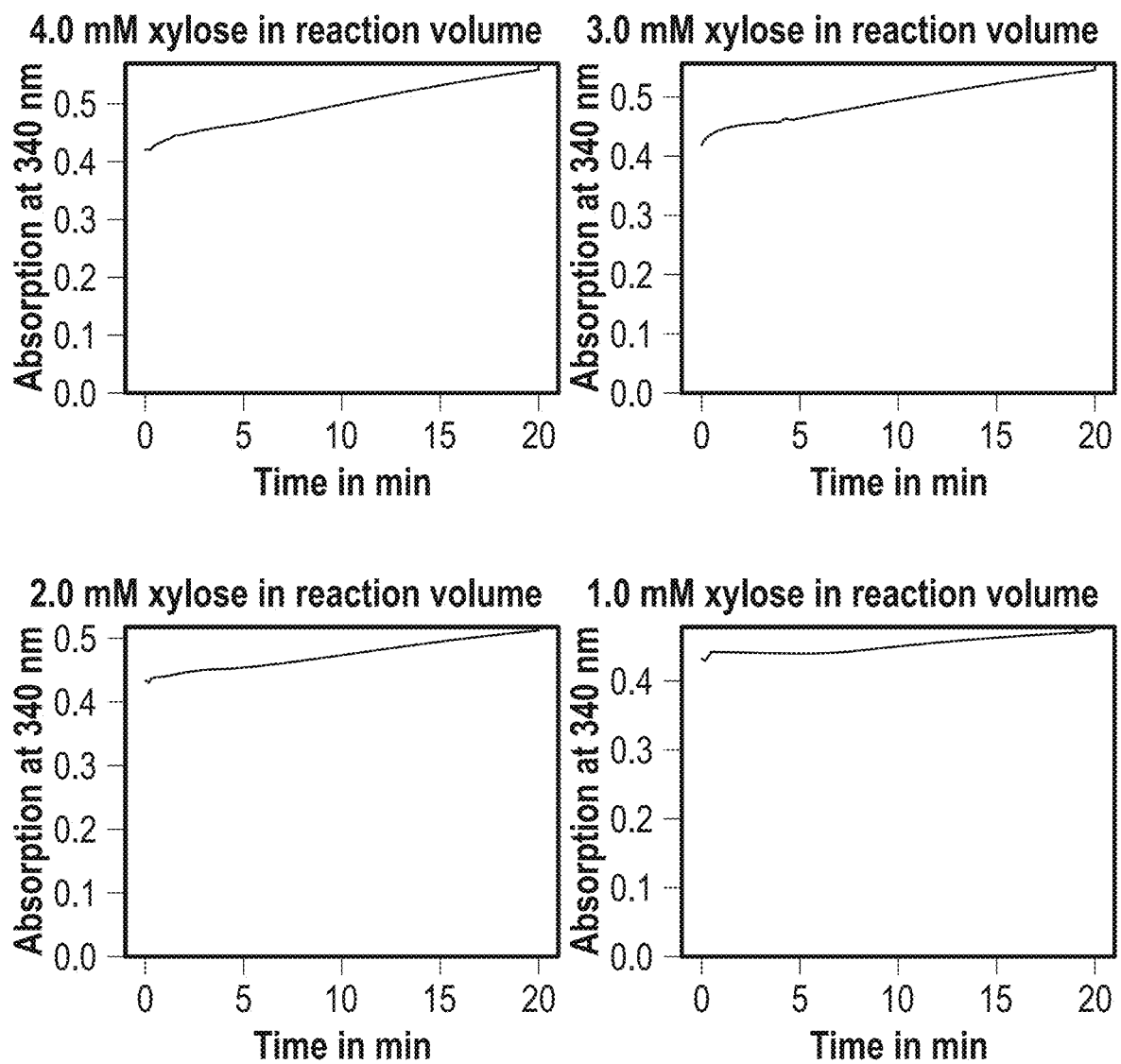
Figure 19:
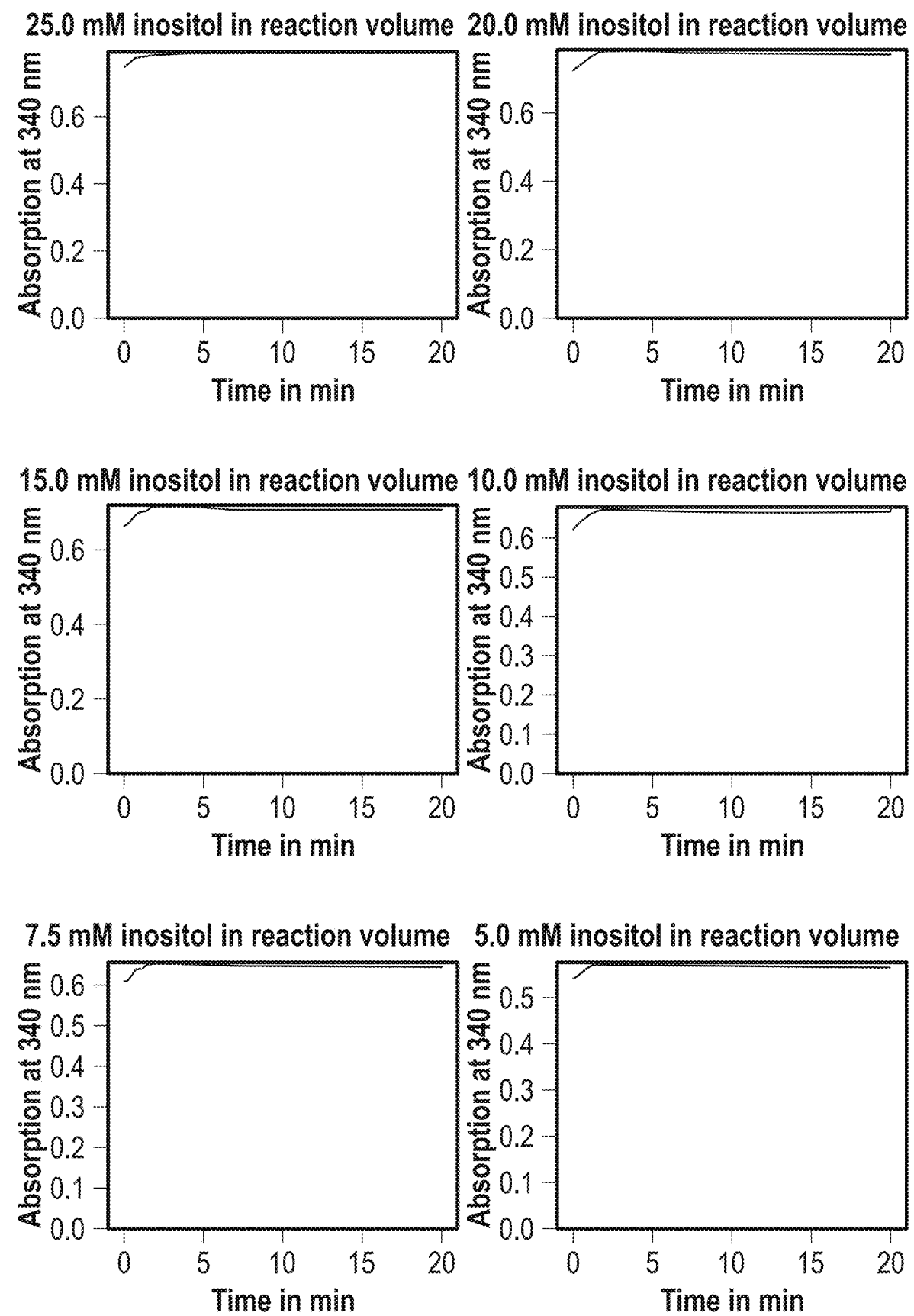
FIG. 19 shows conversion curves for IolG with myo-inositol as substrate, shown analogously to FIG. 18.
Figure 19:
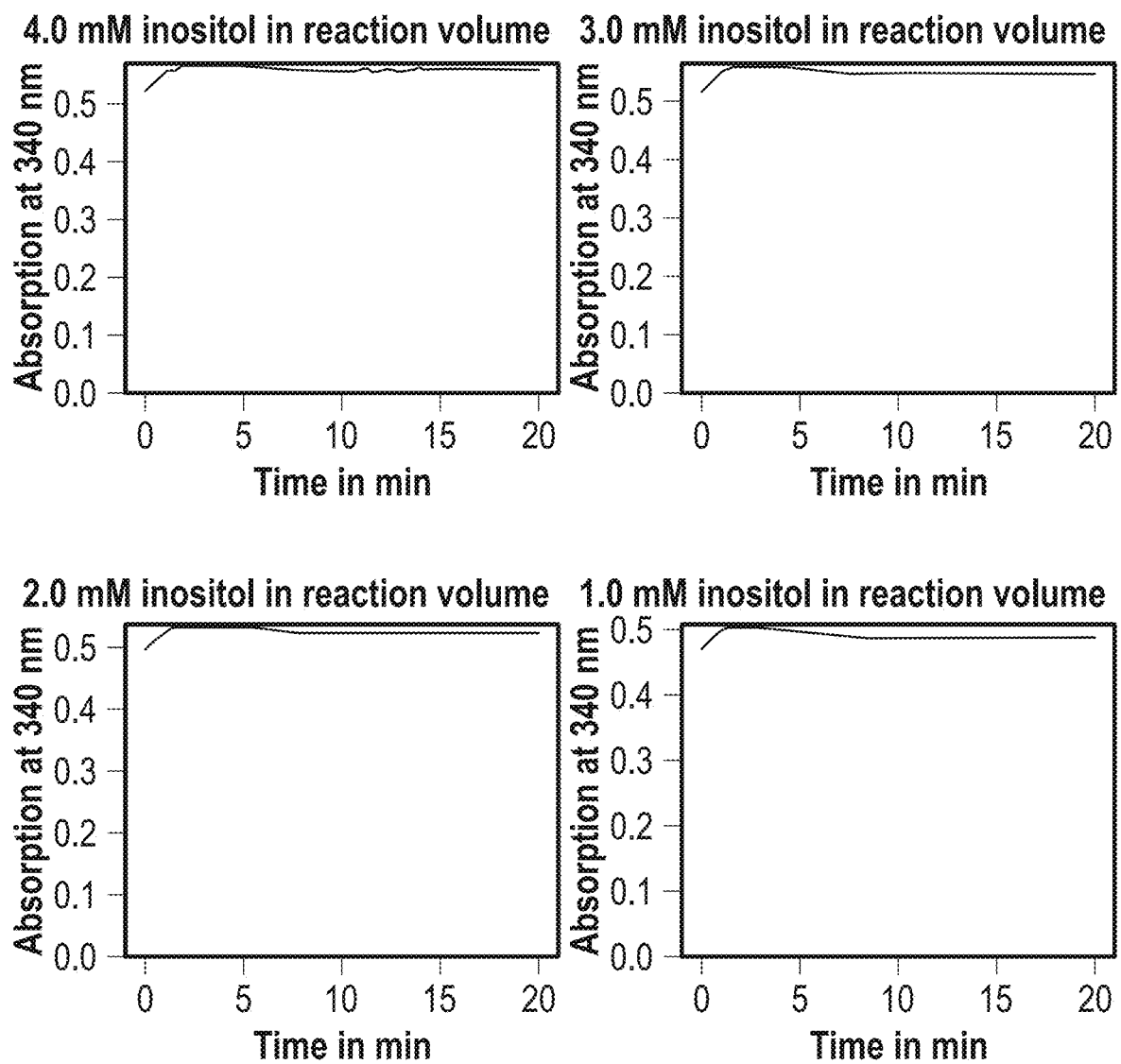
Figure 20:
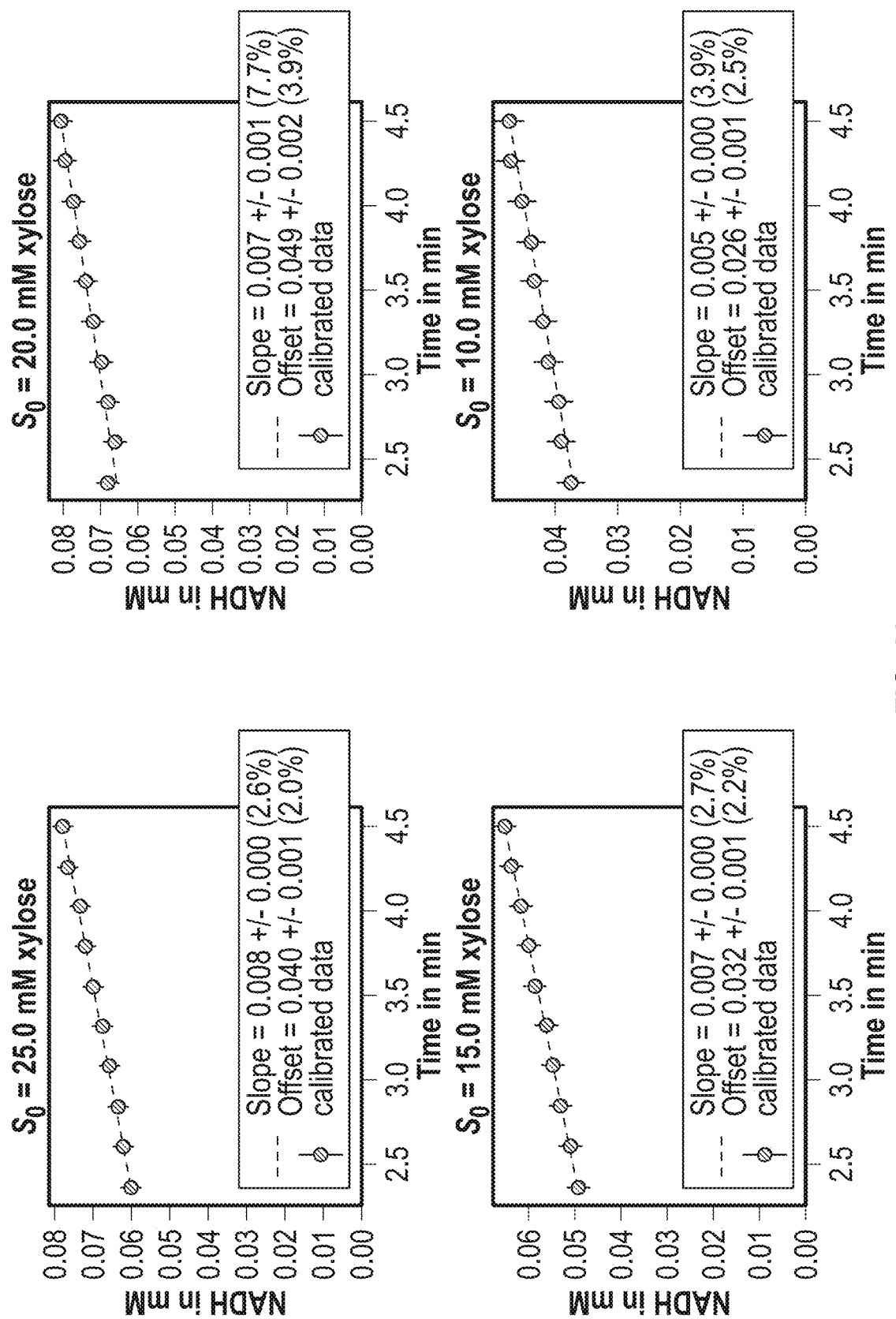
FIG. 20 shows the calculation of initial reaction rates for D-xylose conversion with IolG. Shown are the formations of NADH in mM after calibration of the absorption signal after approx. 2.5 minutes for 10 consecutive measurements (blue dots, approx. 2 minutes duration), for different D-xylene concentrations used respectively from 25 mM (top left) to 1 mM (bottom right). The respective initial reaction rates (red lines) result from the slope of the regression line in mM/min; the respective parameters of the calibration line with values and errors are shown in the individual legends.
Figure 20:
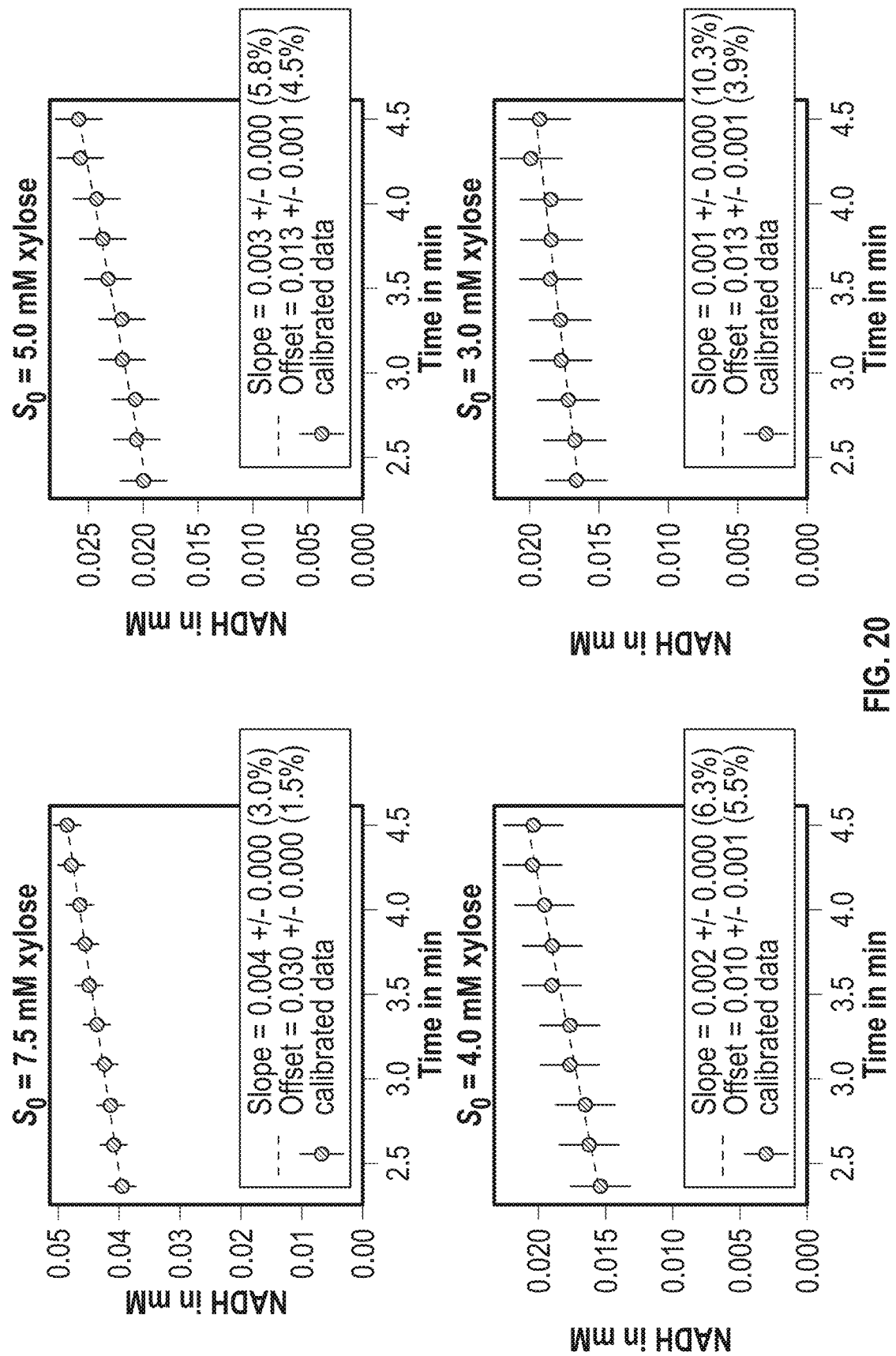
Figure 20:
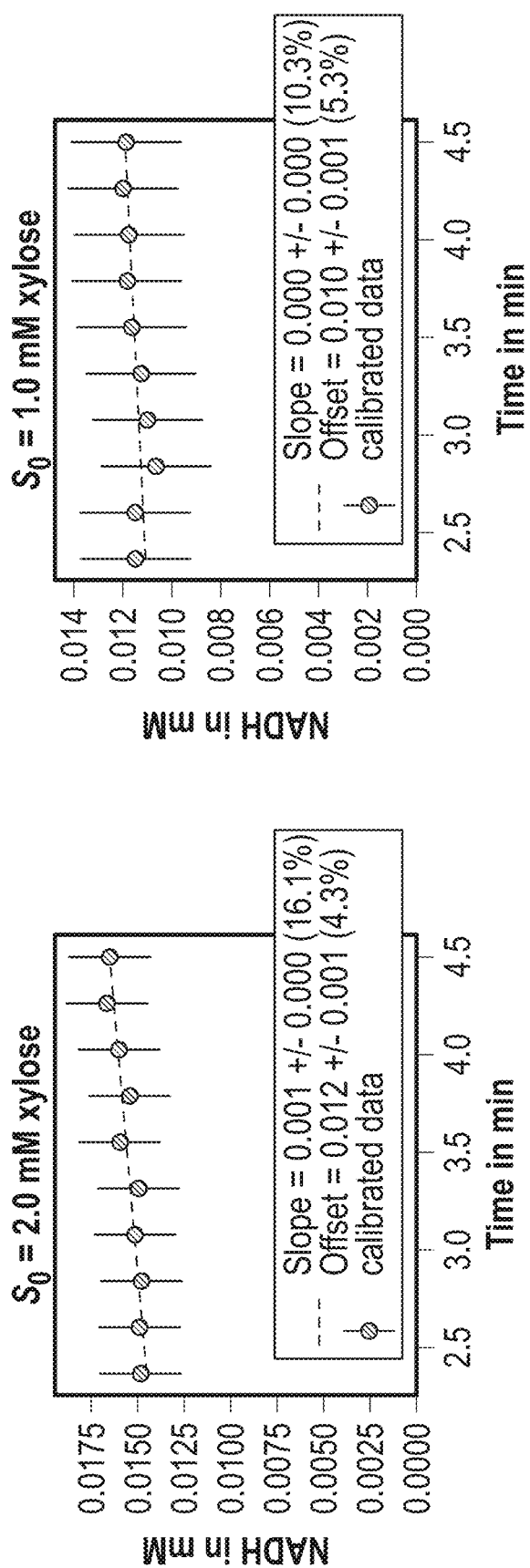
Figure 21:
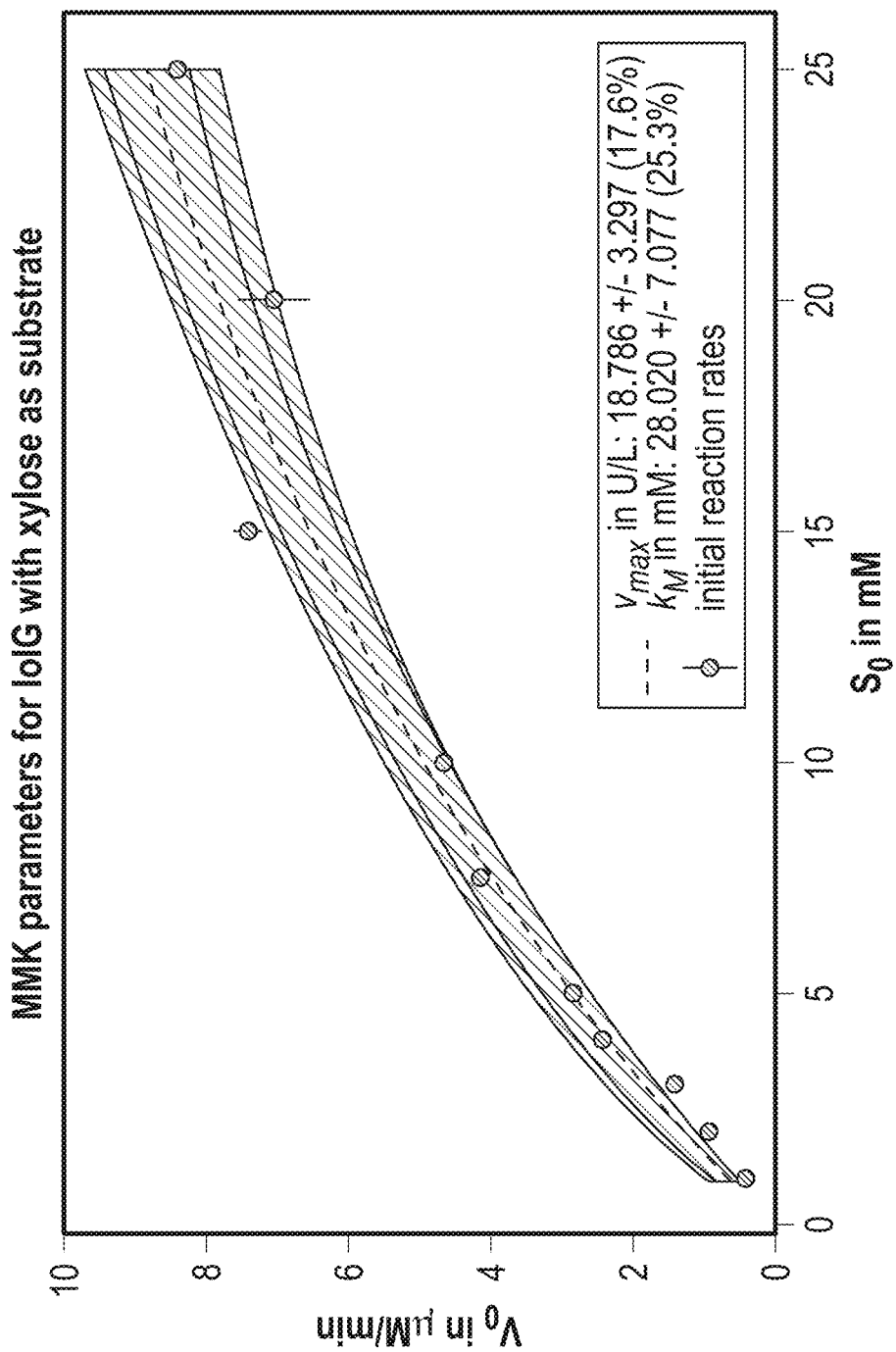
FIG. 21 shows the parameter estimation of Michaelis Menten enzyme kinetics from initial reaction rates in the conversion of D-xylose by the D-xylonate dehydrogenase IolG according to certain embodiments of the invention (black dots). The parameters were determined by weighted non-linear regression assuming normally distributed measurement errors and thus correspond to the maximum likelihood estimator of the parameters of the Michael Menten kinetics. The resulting kinetics are shown as a black dashed line; in addition, kinetics based on random values corresponding to the 2-dimensional normal distribution with covariance matrix of the maximum likelihood estimator are plotted as shaded areas.

FIG. 16 shows the D-xylonate formation of further variants of coryneform bacterial strains according to certain embodiments of the invention in which the functionality of operatively linked regulatory regions is modified or deleted. It shows the strain *C. glutamicum* WT PosiolT1 with modified promoter sequence in the gene region of the D-xylose transporter iolT1, the strain *C. glutamicum* PosiolT1 P$_{O5-O9}$iolC according to certain embodiments of the invention, in which, in addition to PosiolT1, the functionality of the operatively linked regulatory region of the nucleic acid sequence encoding the D-xylose dehydrogenase (P$_{O5-O9}$iolC) is modified and, in comparison, the strain *C. glutamicum* WT ΔiolR, with deletion of the gene for the regulator iolR. The experiments were carried out in shake flasks in defined CGXII medium with 10 gL$^{-1}$ D-glucose and 30 gL$^{-1}$ D-xylose. The strain WT *C. glutamicum* PosiolT1 with modified promoter sequence in the gene region of the D-xylose transporter IolT1 shows slightly increased D-xylonate production due to the deregulated expression of the D-xylose transporter IolT1. The maximum D-xylonate titer after 72 h is 74.73 mM here. The strain *C. glutamicum* WT ΔiolR with deletion of the gene for the regulator IolR shows a markedly increased D-xylonate production due to the deregulated expression of the D-xylose transporter IolT1 and the D-xylose dehydrogenase IolG. The maximum D-xylonate titer after 72 h is 205.53 mM here. The strain *C. glutamicum* P$_{O6}$iolT1 P$_{O5-O9}$iolC, with modified promoter sequence in the gene region of the D-xylose transporter iolT1 and modified functionality of the operatively linked regulatory region of the nucleic acid sequence encoding the D-xylose dehydrogenase ($P_{O5-O9}$iolC), shows a significantly increased D-xylonate production. The maximum D-xylonate titer after 72 h is 206.82 mM here.

Embodiments of the present invention thus clearly show that a markedly increased D-xylonate production is achieved by minimal and extremely defined nucleotide substitutions according to the invention in the 5' upstream regulatory regions of the relevant encoding gene sequences: And this without having to introduce genes or structures into the corynform bacterial strain, and also without the need for drastic deletions to be made on centrally acting regulators, which trigger widely undefined physiological effects in an organism, which is also desirable according to certain embodiments of the invention. The few targeted nucleotide substitutions according to certain embodiments of the invention are present in this case to an extent that they are also naturally found in nature, which distinguishes the coryneform bacterial strain according to certain embodiments of the invention as non-GMO.

The subject matter of the present invention also includes the following exemplary embodiments:

1. Coryneform bacterial cell, characterized in that the enhanced expression of the D-xylose dehydrogenase is based on modifications selected from the group comprising:
   a) modifying the regulation or signal structures for gene expression,
   b) modifying the transcription activity of the encoding nucleic acid sequence,
   c) increasing the gene copy number of the encoding nucleic acid sequence, and
   d) a combination of a)-c).

2. Coryneform bacterial cell according to subject matter 1, characterized in that the increased activity of the D-xylose dehydrogenase activity is based on modifications selected from the group comprising:
   a) increasing the expression of the encoding nucleic acid sequence,
   b) expressing a nucleic acid sequence or fragments or alleles thereof which encodes a D-xylose dehydrogenase with increased catalytic activity and/or substrate specificity,
   c) increasing the stability of the mRNA derived from the encoding nucleic acid sequence,
   d) modifying the catalytic activity and/or substrate specificity of a homologous D-xylose dehydrogenase for the conversion of D-xylose, and
   e) a combination of a)-d).

3. Coryneform bacterial cell according to any one of subject matters 1 or 2,
   a) wherein the activity of a D-xylose dehydrogenase according to the invention is increased,
   b) wherein a nucleic acid sequence according to the invention is enhancedly expressed,
   c) wherein a nucleic acid sequence encoding a myo-inositol/proton symporter (IolT1) according to SEQ ID NO. 3 or fragments or alleles thereof is enhancedly expressed,
   d) wherein the activity of a myo-inositol/proton symporter IolT1 having an amino acid sequence according to SEQ ID NO. 4 or fragments thereof is increased,
   e) having a nucleic acid sequence encoding a myo-inositol/proton symporter (IolT1) with one or more nucleotide substitutions or nucleotide deletions in the operatively linked IolR binding sites of the iolT1 gene, preferably selected from the group of nucleic acid sequences SEQ ID NO. 9 and SEQ ID NO. 10 or fragments or alleles thereof,
   f) wherein a nucleic acid sequence encoding a myo-inositol/proton symporter (IolT2) according to SEQ ID NO. 5 or fragments or alleles thereof is enhancedly expressed,
   g) wherein the activity of a myo-inositol/proton symporter IolT2 having an amino acid sequence according to SEQ ID NO. 6 or fragments thereof is increased,
   h) wherein both nucleic acid sequences encoding myo-inositol/proton symporters IolT1/2 are enhancedly expressed according to c) and f),
   i) wherein the activity of both myo-inositol/proton symporters IolT1/2 is increased according to d) and g),
   j) having a nucleic acid sequence according to the invention, wherein the functionality of one or more operatively linked IolR binding sites in the regulatory, non-coding region of the iolC gene cluster, containing iolG encoding a D-xylose dehydrogenase according to the invention, is reduced or turned off, or one or more IolR binding sites are partially or completely deleted,
   k) having a nucleic acid sequence encoding a D-xylose dehydrogenase with one or more nucleotide substitutions or nucleotide deletions in the operatively linked IolR binding sites of the iolC gene cluster, preferably selected from the group containing nucleic acid sequences according to SEQ ID NO. 7, SEQ ID NO. 8, SEQ ID NO. 63, and SEQ ID NO. 64 or fragments or alleles thereof,
   l) a nucleic acid sequence encoding a myo-inositol regulator IolR or fragments or alleles thereof is completely or partially deleted,
   m) the expression of an iolR gene is reduced or is absent,
   n) the activity of a myo-inositol regulator IolR is reduced or is completely turned off, or
   o) a combination of a)-n).

4. Process for preparing D-xylonate, preferably with coryneform bacteria, according to any one of subject matters 1 to 3, comprising the steps of:
   a) providing a solution containing water and a C5 carbon source,
   b) microbial reaction of the C5 carbon source in a solution according to step a) to form D-xylonate in the presence of a coryneform bacterial cell in which the expression of a nucleic acid sequence encoding a homologous D-xylose dehydrogenase is enhanced and/or in which the activity of a homologous D-xylose dehydrogenase is increased, and
   c) optional isolation and/or preparation of D-xylonate from the solution.

TABLE 1

| Reference | |
|---|---|
| Strain | |
| C. glutamicum ATCC13032 wild type | Abe et al., 1967 (https://doi.org/10.2323/jgam.13.279) |
| C. glutamicum ATCC13032 $P_{O6}$ iolT1 | Brüsseler et al., 2018(https://doi.org/10.1016/j.biortech.2017.10.098) |
| C. glutamicum ATCC13032 $P_{O6}$ iolT1 $P_{O13}$ iolC | herein |
| C. glutamicum ATCC13032 $P_{O6}$ iolT1 $P_{O5-O9}$ iolC | herein |
| C. glutamicum ATCC13032 $\Delta P_{O6}$ iolT1 | herein |
| C. glutamicum ATCC13032 $\Delta PO13$ iolC | herein |
| C. glutamicum ATCC13032 $\Delta P_{O5-O9}$ iolC | herein |
| C. glutamicum ATCC13032 $\Delta$iolG | herein |
| C. glutamicum ATCC13032 iolG$^1$ | herein |
| C. glutamicum ATCC13032 iolG$^2$ | herein |
| C. glutamicum ATCC13032 iolG$^3$ | herein |
| C. glutamicum ATCC13032 pEKEx3 iolG | herein |
| E.coli DH5α | Thermo Fisher Scientific (Waltham, MA, USA) |
| E.coli BL21(DE3) | Merck (Darmstadt, Germany) |
| Plasmid | |
| pEKEx3 | Gande et al., 2007 (https://doi.org/10.1128/JB.00254-07) |
| pk19mobsacB | Schäfer et al., 1994 (https://doi.org/10.1016/0378-1119(94)90324-7) |
| pET-28b | Merck (Darmstadt, Germany) |
| pk19mobsacB $P_{O6}$iolT1 | Brüsseler et al., 2018 (https://doi.org/10.1016/j.biortech.2017.10.098) |
| pk19mobsacB $P_{O13}$iolC | herein |
| pk19mobsacB $P_{O5-O9}$iolC | herein |
| pk19mobsacB $\Delta$ $P_{O6}$iolT1 | herein |
| pk19mobsacB $\Delta$ $P_{O13}$iolC | herein |
| pk19mobsacB $\Delta$ $P_{O5-O9}$iolC | herein |
| pk19mobsacB $\Delta$ iolG | herein |
| pk19mobsacB CgLP12 $P_{Tuf}$iolG | herein |
| pk19mobsacB CgLP4 $P_{Tuf}$iolG | herein |
| pk19mobsacB ncr cons $P_{Tuf}$iolG | herein |
| pEKEx3 iolG | herein |

TABLE 2

| Sequence | Description | Source |
|---|---|---|
| SEQ ID NO. 1 | Nucleic acid sequence of a D-xylose dehydrogenase gene (iolG) from coryneform bacteria | herein |
| SEQ ID NO. 2 | Amino acid sequence of a D-xylose dehydrogenase (IolG) from coryneform bacteria | herein |
| SEQ ID NO. 3 | Nucleic acid sequence of a myo-inositol/proton symporter gene (iolT1) from coryneform bacteria with 5' regulatory region | Ikeda and Nakagawa, 2003 (DOI 10.1007/S00253-003-1328-1) |
| SEQ ID NO. 4 | Amino acid sequence of a myo-inositol/proton symporter (IolT1) from coryneform bacteria | Ikeda and Nakagawa, 2003 (DOI 10.1007/S00253-003-1328-1) |
| SEQ ID NO. 5 | Nucleic acid sequence of a myo-inositol/proton symporter gene (iolT2) from coryneform bacteria | Ikeda and Nakagawa, 2003 (DOI 10.1007/S00253-003-1328-1) |
| SEQ ID NO. 6 | Amino acid sequence of a myo-inositol/proton symporter (IolT2) from coryneform bacteria | Ikeda and Nakagawa, 2003 (DOI 10.1007/S00253-003-1328-1) |
| SEQ ID NO. 7 | Nucleic acid sequence having one or more nucleotide substitutions in the operatively linked IolR binding sites of the iolC gene cluster containing the encoding region of the D-xylose dehydrogenase gene according to certain embodiments of the invention from coryneform bacteria; ($P_{O13}$iolC with 5' regulatory region and substitution at position 383 (C->G) and 384 (A->G)) | herein |
| SEQ ID NO. 8 | Nucleic acid sequence having one or more nucleotide deletions in the operatively linked IolR binding sites of the iolC gene cluster containing the encoding region of the D-xylose dehydrogenase gene according to certain embodiments of the invention from coryneform | herein |

TABLE 2-continued

| Sequence | Description | Source |
|---|---|---|
|  | bacteria; (ΔP013iolC with 5' regulatory region and deletion at position 383 (C) and 384 (A)) |  |
| SEQ ID NO. 9 | Nucleic acid sequence having one or more nucleotide substitutions in the operatively linked IolR binding sites of the iolT1 gene; (P06iolT1 with 5' regulatory region and substitution at position 383 (C->G) and 384 (A->G)) | herein |
| SEQ ID NO. 10 | Nucleic acid sequence having one or more nucleotide deletions in the operatively linked IolR binding sites of the iolT1 gene; (ΔP06iolT1 with 5' regulatory region and deletion at position 383 (C) and 384 (A)) | herein |
| SEQ ID NO. 11 | Primer PromiolT1_fw_fw | herein |
| SEQ ID NO. 12 | Primer PromiolT1fw_rev | herein |
| SEQ ID NO. 13 | Primer Piolt1_rev_fw | herein |
| SEQ ID NO. 14 | Primer Piolt1_rev_rev | herein |
| SEQ ID NO. 15 | Primer checkPromiolT1fw | herein |
| SEQ ID NO. 16 | Primer checkPromiolT1rev | herein |
| SEQ ID NO. 17 | Primer PO13 iolC fw | herein |
| SEQ ID NO. 18 | Primer PO13 iolC rev | herein |
| SEQ ID NO. 19 | Primer PO13 iolC rev_fw | herein |
| SEQ ID NO. 20 | Primer PO13 iolC rev_rev | herein |
| SEQ ID NO. 21 | Primer Check Prom iolC fw | herein |
| SEQ ID NO. 22 | Primer Check Prom iolC_rev | herein |
| SEQ ID NO. 23 | Primer DPO6iolT1_Fw_fw | herein |
| SEQ ID NO. 24 | Primer DPO6iolT1_Fw_rev | herein |
| SEQ ID NO. 25 | Primer DPO6iolT1_rev_fw | herein |
| SEQ ID NO. 26 | Primer DPO6iolT1_rev_rev | herein |
| SEQ ID NO. 27 | Primer DPO13iolC_fw_fw | herein |
| SEQ ID NO. 28 | Primer DPO13iolC_fw_rev | herein |
| SEQ ID NO. 29 | Primer DPO13iolC_rev_fw | herein |
| SEQ ID NO. 30 | Primer DPO13iolC_rev_rev | herein |
| SEQ ID NO. 31 | Primer iolG front fw | herein |
| SEQ ID NO. 32 | Primer iolG front rev | herein |
| SEQ ID NO. 33 | Primer iolG back fw | herein |
| SEQ ID NO. 34 | Primer iolG back rev | herein |
| SEQ ID NO. 35 | Primer check iolG fw | herein |
| SEQ ID NO. 36 | Primer check iolG rev | herein |
| SEQ ID NO. 37 | Primer NCS_PTuf_fw | herein |
| SEQ ID NO. 38 | Primer NCS_PTuf_rev | herein |
| SEQ ID NO. 39 | Primer NCS_Ptuf_iolG_fw | herein |
| SEQ ID NO. 40 | Primer NCS_Ptuf_iolG_rev | herein |
| SEQ ID NO. 41 | Primer NCS check fw | herein |
| SEQ ID NO. 42 | Primer NCS check rev | herein |
| SEQ ID NO. 43 | Primer CgLP4_fw_fw | herein |
| SEQ ID NO. 44 | Primer CgLP4_fw_rev | herein |
| SEQ ID NO. 45 | Primer CgLP4_PTuf_fw | herein |
| SEQ ID NO. 46 | Primer CgLP4_PTuf_rev | herein |
| SEQ ID NO. 47 | Primer CgLP4_iolG_fw | herein |
| SEQ ID NO. 48 | Primer CgLP4_iolG_rev | herein |
| SEQ ID NO. 49 | Primer CgLP4_rev_fw | herein |
| SEQ ID NO. 50 | Primer CgLP4_rev_rev | herein |
| SEQ ID NO. 51 | Primer CgLP4_Check_fw | herein |
| SEQ ID NO. 52 | Primer CgLP4_Check_rev | herein |
| SEQ ID NO. 53 | Primer CgLP12_fw_fw | herein |
| SEQ ID NO. 54 | Primer CgLP12_fw_rev | herein |
| SEQ ID NO. 55 | Primer CgLP12_PTuf_fw | herein |
| SEQ ID NO. 56 | Primer CgLP12_PTuf_rev | herein |
| SEQ ID NO. 57 | Primer CgLP12_iolG_fw | herein |
| SEQ ID NO. 58 | Primer CgLP12_iolG_rev | herein |
| SEQ ID NO. 59 | Primer CgLP12_rev_fw | herein |
| SEQ ID NO. 60 | Primer CgLP12_rev_rev | herein |
| SEQ ID NO. 61 | Primer CgLP12_Check_Fw | herein |
| SEQ ID NO. 62 | Primer CgLP12_Check_Rev | herein |
| SEQ ID NO. 63 | Nucleic acid sequence having one or more nucleotide substitutions in the operatively linked IolR binding sites of the iolC gene cluster containing the encoding region of the D-xylose dehydrogenase gene according to certain embodiments of the invention from coryneform bacteria; ($P_{06}$iolT1$\Delta P_{05\text{-}09}$iolC with 5' regulatory region and substitution at position 143 (A->G), 144 (C->G), 211 (A->G), and 212 (C->G)) | herein |
| SEQ ID NO. 64 | Nucleic acid sequence having one or more nucleotide deletions in the operatively linked IolR binding sites of the iolC gene cluster containing the encoding region of the D-xylose dehydrogenase gene according to certain embodiments of the invention from coryneform bacteria; ($P_{06}$iolT1$\Delta P_{05\text{-}09}$iolC with 5' regulatory region and deletion at position 143 (A), 144 (C), 211 (A), and 212(C)) | herein |
| SEQ ID NO. 65 | Primer CgPO5-PO9 iolC_fw_fw | herein |
| SEQ ID NO. 66 | Primer CgPO5-PO9 iolC_fw_rev | herein |
| SEQ ID NO. 67 | Primer Cg PO5-PO9iolC_rev_fw | herein |
| SEQ ID NO. 68 | Primer Cg PO5-PO9iolC_rev_rev | herein |
| SEQ ID NO. 69 | Primer Cg PO5-PO9iolC_check_fw | herein |
| SEQ ID NO. 70 | Primer Cg PO5-PO9iolC_check_rev | herein |
| SEQ ID NO. 71 | Primer Cg ΔPO5-PO9iolC_fw_fw | herein |
| SEQ ID NO. 72 | Primer Cg ΔPO5-PO9iolC_fw_rev | herein |
| SEQ ID NO. 73 | Primer Cg ΔPO5-PO9iolC_rev_fw | herein |
| SEQ ID NO. 74 | Primer Cg ΔPO5-PO9iolC_rev_rev | herein |
| SEQ ID NO. 75 | Primer Cg Check ΔPO5-PO9iol_fw | herein |
| SEQ ID NO. 76 | Primer Cg Check ΔPO5-PO9iolC_rev | herein |

While the invention has been illustrated and described in detail in the drawings and foregoing description, such illustration and description are to be considered illustrative or exemplary and not restrictive. It will be understood that changes and modifications may be made by those of ordinary skill within the scope of the following claims. In particular, the present invention covers further embodiments with any combination of features from different embodiments described above and below. Additionally, statements made herein characterizing the invention refer to an embodiment of the invention and not necessarily all embodiments.

The terms used in the claims should be construed to have the broadest reasonable interpretation consistent with the foregoing description. For example, the use of the article "a" or "the" in introducing an element should not be interpreted as being exclusive of a plurality of elements. Likewise, the recitation of "or" should be interpreted as being inclusive, such that the recitation of "A or B" is not exclusive of "A and B," unless it is clear from the context or the foregoing description that only one of A and B is intended. Further, the recitation of "at least one of A, B and C" should be interpreted as one or more of a group of elements consisting of A, B and C, and should not be interpreted as requiring at least one of each of the listed elements A, B and C, regardless of whether A, B and C are related as categories or otherwise. Moreover, the recitation of "A, B and/or C" or "at least one of A, B or C" should be interpreted as including any singular entity from the listed elements, e.g., A, any subset from the listed elements, e.g., A and B, or the entire list of elements A, B and C.

The invention claimed is:

1. A coryneform bacterial cell, wherein the coryneform bacterial cell has an enhanced expression and/or increased activity, compared to the expression of the respective parent gene or enzyme in a wild type coryneform bacterial cell, of a homologous D-xylose dehydrogenase comprising an amino acid sequence that has at least 70% identity to the amino acid sequence according to SEQ ID NO. 2, wherein the coryneform bacterial cell comprises a nucleic acid sequence with one or more nucleotide substitutions or nucleotide deletions in the operatively linked IolR binding sites of the iolT1 gene selected from the group containing nucleic acid sequences according to SEQ ID NO. 9 and SEQ ID NO. 10, which enhances expression and/or increases activity of the homologous D-xylose dehydrogenase in the coryneform bacterial cell.

2. The coryneform bacterial cell according to claim 1, wherein the coryneform bacterial cell comprises a first nucleic acid sequence, wherein the first nucleic acid sequence is
a) a nucleic acid sequence containing at least 70% identity to the nucleic acid sequence according to SEQ ID NO. 1,
b) a nucleic acid sequence which, under stringent conditions, hybridizes with a complementary sequence of a nucleic acid sequence according to SEQ ID NO. 1,
c) a nucleic acid sequence according to SEQ. ID NO. 1, or
d) a nucleic acid sequence encoding a D-xylose dehydrogenase corresponding to each of the nucleic acids according to a)-c) but which differs from these nucleic acid sequences according to a)-c) by the degeneracy of the genetic code or functionally neutral mutations, and wherein the functionality of one or more operatively linked IolR binding sites in the regulatory, non-coding region of the nucleic acid sequence encoding the D-xylose dehydrogenase in the iolC gene cluster is reduced or turned off, or one or more IolR binding sites are partially or completely deleted.

3. The coryneform bacterial cell according claim 1, wherein the coryneform bacterial cell has a nucleic acid sequence with one or more nucleotide substitutions or nucleotide deletions in the operatively linked IolR binding sites of the iolC gene cluster selected from the group containing nucleic acid sequences according to SEQ ID NO. 7 and SEQ ID NO. 8.

4. The coryneform bacterial cell according to claim 1, wherein the coryneform bacterial cell has a nucleic acid sequence with one or more nucleotide substitutions or nucleotide deletions in the operatively linked IolR binding sites of the iolC gene cluster selected from the group containing nucleic acid sequences according to SEQ ID NO. 63 and SEQ ID NO. 64.

5. The coryneform bacterial cell according to claim 1, wherein the coryneform bacterial cell is
*Corynebacterium, Brevibacterium, Corynebacterium glutamicum, Corynebacterium acetoglutamicum, Corynebacterium thermoaminogenes, Brevibacterium flavum, Brevibacterium lactofermentum*, or *Brevibacterium divaricatum*.

6. The coryneform bacterial cell according to claim 1, wherein the coryneform bacterial cell is *Corynebacterium glutamicum* ATCC13032, *Corynebacterium acetoglutamicum* ATCC15806, *Corynebacterium acetoacidophilum* ATCC13870, *Corynebacterium thermoaminogenes* FERM BP-1539, *Brevibacterium flavum* ATCC14067, *Brevibacterium lactofermentum* ATCC13869, or *Brevibacterium divaricatum* ATCC14020.

7. The coryneform bacterial cell according to claim 1, wherein the coryneform bacterial cell comprises an increased copy number of a nucleic acid sequence encoding D-xylose dehydrogenase, and wherein the increased copy number is chromosomally encoded.

8. The coryneform bacterial cell according to claim 1, wherein the coryneform bacterial cell comprises an increased copy number of a nucleic acid sequence encoding D-xylose dehydrogenase, and wherein the increased copy number is extra-chromosomally encoded.

9. The coryneform bacterial cell according to claim 2,
a) wherein the activity of the D-xylose dehydrogenase is increased,
b) wherein the first nucleic acid sequence is enhancedly expressed,
c) wherein the coryneform bacterial cell comprises a second nucleic acid sequence that encodes a myo-inositol/proton symporter (IolT1) according to SEQ ID NO. 3 or fragments or alleles thereof, and wherein the second nucleic acid sequence is enhancedly expressed,
d) wherein the myo-inositol/proton symporter IolT1 encoded by the second nucleic acid sequence comprises an amino acid sequence according to SEQ ID NO. 4 or fragments thereof, and wherein the activity of the IolT1 is increased,
e) wherein the second nucleic acid sequence encoding a myo-inositol/proton symporter (IolT1) comprises one or more nucleotide substitutions or nucleotide deletions in the operatively linked IolR binding sites of the iolT1 gene,
f) wherein the coryneform bacterial cell comprises a third nucleic acid sequence that encodes a myo-inositol/proton symporter (IolT2) according to SEQ ID NO. 5 or fragments or alleles thereof, and wherein the third nucleic acid sequence is enhancedly expressed,
g) wherein the myo-inositol/proton symporter IolT2 encoded by the third nucleic acid sequence comprises an amino acid sequence according to SEQ ID NO. 6 or fragments thereof, and wherein the activity of the IolT2 is increased,
h) wherein the second and third nucleic acid sequences encoding myo-inositol/proton symporters IolT1/2 are enhancedly expressed,
i) wherein the activity of both myo-inositol/proton symporters IolT1/2 is increased,
j) having the nucleic acid sequence encoding the D-xylose dehydrogenase comprises one or more nucleotide substitutions or nucleotide deletions in the operatively linked IolR binding sites of the iolC gene cluster, or
k) any combination of a)-j).

10. A process for preparing D-xylonate, comprising the steps of:
a) providing a solution containing water and a carbon source,
b) culturing the coryneform bacterial cell of claim 1 in the presence of the solution according to step a) to form D-xylonate.

11. The process according to claim 10, wherein the D-xylose dehydrogenase in step b) is encoded by a nucleic acid sequence which has at least 70% identity to the nucleic acid sequence according to SEQ ID NO. 1.

12. The process according to claim 10, wherein the carbon source is a) oligosaccharides or polysaccharides containing D-xylose units, b) D-xylose, c) biomass containing lignocellulose, cellulose, or hemicellulose, the hydrolysate thereof or extract obtained therefrom containing D-xylose units, or d) any combination of a)-c).

13. The process according to claim 10, wherein the carbon source is bagasse.

14. The process according to claim 10, wherein the culturing takes place discontinuously or continuously, preferably in batch, fed batch, repeated fed batch mode or as a one-pot hydrolysis fermentation process.

15. The process according to claim 10, wherein the solution comprises D glucose in addition to D-xylose.

16. The process according to claim 10, wherein the culturing takes place in fed batch mode.

17. The process according to claim 10, wherein the coryneform bacterial cell is not recombinantly modified.

* * * * *

```
                         SEQUENCE LISTING

<160> NUMBER OF SEQ ID NOS: 76

<210> SEQ ID NO 1
<211> LENGTH: 1011
<212> TYPE: DNA
<213> ORGANISM: Corynebacterium glutamicum
<220> FEATURE:
<221> NAME/KEY: iolG CDS D-Xylose-Dehydrogenase
<222> LOCATION: (1)..(1011)

<400> SEQUENCE: 1
atgagcaaga gccttcgcgt tggagttgtc ggtgcaggag ccatgggtgc tgaccacatc      60
gatcgcatca acaaccgcac ctctggtgca cacatctctg ccattattga gcccgacgca     120
gcacgtgccg ctgcagctgc agaagacgcg ccgggtgcac aggccttcac tcgcattgaa     180
gatgctatcg cagccgatgc tgtcgacgca gtgctgatcg ccgtaccagg tcagttccat     240
gagccagtac ttgtcccagc actagaagca ggccttccca tcctgtgtga aaagccactg     300
accccagatt ctgaatcctc actgcgcatc gtcgagctgg agcagaagct ggacaagcca     360
cacatccagg ttggtttcat gcgccgcttc gaccctgagt acaacaactt gcgcaaattg     420
gtggaatccg gcgaagctgg cgaactgctc atgctccgcg gcctgcaccg caacccaagt     480
gttggtgaga gctacaccca gtccatgctg atcaccgact ccgtcgtcca cgaattcgat     540
gtcatcccat ggctcgcagg ctcccgagtt gtctccgttg aagtgaagta cccaaagacc     600
tcctcactgg cgcactccgg cctcaaggaa ccaatcctgg tgatcatgga gctcgaaaac     660
ggcgtgcttg tcgacgtaga gatgaacgta aacattcaat tcggatacca ggtagcaacc     720
gaagcggtct ttgaaaaggg acttgcccgc atcggccagc catccggaat gcagcgctgg     780
cgcgacggtg aattcctgat caacgaacac accgatttca ccacccgttt cgctaccgcc     840
tacgaccgcc agatccagag ctgggtcgac gcagtccacg aaggcaccct ggtcgcaggc     900
cctaacgcat gggatggtta cctggttgca ctgtcatgcg aagctggtgt caaggcactc     960
gacggcggcg tcatcccagt tgatgcggca cctcgcccag atttctacgc t             1011

<210> SEQ ID NO 2
<211> LENGTH: 337
<212> TYPE: PRT
<213> ORGANISM: Corynebacterium glutamicum
<220> FEATURE:
<221> NAME/KEY: IolG Protein D-Xylose-Dehydrogenase
<222> LOCATION: (1)..(337)

<400> SEQUENCE: 2

Met Ser Lys Ser Leu Arg Val Gly Val Val Gly Ala Gly Ala Met Gly
1               5                   10                  15

Ala Asp His Ile Asp Arg Ile Asn Asn Arg Thr Ser Gly Ala His Ile
            20                  25                  30

Ser Ala Ile Ile Glu Pro Asp Ala Ala Arg Ala Ala Ala Ala Ala Glu
        35                  40                  45

Asp Ala Pro Gly Ala Gln Ala Phe Thr Arg Ile Glu Asp Ala Ile Ala
```

```
                50              55              60
    Ala Asp Ala Val Asp Ala Val Leu Ile Ala Val Pro Gly Gln Phe His
 65                      70                  75                  80

Glu Pro Val Leu Val Pro Ala Leu Glu Ala Gly Leu Pro Ile Leu Cys
                    85                  90                  95

Glu Lys Pro Leu Thr Pro Asp Ser Glu Ser Ser Leu Arg Ile Val Glu
                    100                 105                 110

Leu Glu Gln Lys Leu Asp Lys Pro His Ile Gln Val Gly Phe Met Arg
                115                 120                 125

Arg Phe Asp Pro Glu Tyr Asn Asn Leu Arg Lys Leu Val Glu Ser Gly
            130                 135                 140

Glu Ala Gly Glu Leu Leu Met Leu Arg Gly Leu His Arg Asn Pro Ser
145                 150                 155                 160

Val Gly Glu Ser Tyr Thr Gln Ser Met Leu Ile Thr Asp Ser Val Val
                    165                 170                 175

His Glu Phe Asp Val Ile Pro Trp Leu Ala Gly Ser Arg Val Val Ser
                180                 185                 190

Val Glu Val Lys Tyr Pro Lys Thr Ser Ser Leu Ala His Ser Gly Leu
                195                 200                 205

Lys Glu Pro Ile Leu Val Ile Met Glu Leu Glu Asn Gly Val Leu Val
            210                 215                 220

Asp Val Glu Met Asn Val Asn Ile Gln Phe Gly Tyr Gln Val Ala Thr
225                 230                 235                 240

Glu Ala Val Phe Glu Lys Gly Leu Ala Arg Ile Gly Gln Pro Ser Gly
                    245                 250                 255

Met Gln Arg Trp Arg Asp Gly Glu Phe Leu Ile Asn Glu His Thr Asp
                260                 265                 270

Phe Thr Thr Arg Phe Ala Thr Ala Tyr Asp Arg Gln Ile Gln Ser Trp
            275                 280                 285

Val Asp Ala Val His Glu Gly Thr Leu Val Ala Gly Pro Asn Ala Trp
290                 295                 300

Asp Gly Tyr Leu Val Ala Leu Ser Cys Glu Ala Gly Val Lys Ala Leu
305                 310                 315                 320

Asp Gly Gly Val Ile Pro Val Asp Ala Ala Pro Arg Pro Asp Phe Tyr
                    325                 330                 335

Ala

<210> SEQ ID NO 3
<211> LENGTH: 2253
<212> TYPE: DNA
<213> ORGANISM: Corynebacterium glutamicum
<220> FEATURE:
<221> NAME/KEY: iolT1-Gen mit 5' regulat Bereich und CDS
<222> LOCATION: (1)..(2253)

<400> SEQUENCE: 3
accttgattg atcatgtcga ggaaagccgt acggctttcc tctgggattg ttctacgaat    60
gcccacttcg cacccttcgg gttgctcgtg gtgcattcac cccctgaacc cgcctagggt   120
ttgatgcaaa aattcgttcg actttatggc cagacctcac gcctgtggtg aaaaattgat   180
cagcaaacac ccaggtttca cattcgcccc accagtccca aaatgatgac gttccagagc   240
gccgcctgac ggcaatttgt gcccactttg acacaagtgg tcgatcgacg tctcgagccg   300
cttaaacggg cgattatcgc cccaccattc ccgatgtccg ctcctcgcac gcttttgta    360 atgacattag gatctttaag cagtgaatga ggtgacaatg tcacctaaca aaggtgtcaa   420
```

-continued

```
acagccccaa tcactacccc ctccaccccc gcacccttat ccagaaactc ccatgctcca      480
acatttccag aggggggcagt ttctgacatt aaccacataa ctcctgcatc aaaccgcagc      540
taacagccac acccctgctg aaaatcccga atggaaaacc atacccaagc agacaccccc      600
acccctaagt attaccaatt actcaaaagt attcaaaaaa agtttgttat gtacgattga      660
cgggcaatat cgtgtctgcc acgattaaag acattggtga tgtgaatcac tgcctactac      720
atcgtgtttc gtgaccctgc acctccaagt aagggcacga caaacttagg agacaagatg      780
gctagtacct tcattcaggc cgacagccct gaaaaaagta agaagctgcc cccactcaca      840
gaaggtccgt atagaaagcg gctattctac gttgcactag ttgcgacgtt tggtgggctg      900
ctcttcggat atgacaccgg agtaatcaac ggtgcactca acccaatgac acgtgagctc      960
ggactaaccg cgttcaccga gggtgttgta acttcttccc tgctgtttgg tgcagcagct     1020
ggtgcgatgt ttttcggtcg catttccgac aactggggtc gccggaaaac aatcatctca     1080
cttgcagtag ctttctttgt cggcaccatg atctgcgtgt ttgctccatc ttttgcagta     1140
atggttgtcg acgtgtgct tcttggactc gcagttggtg gcgcttccac tgttgtccct     1200
gtctacctgg ctgaacttgc tccttttgaa atccgtggct cactggctgg ccgtaatgag     1260
ttgatgattg ttgttggtca gctcgcagct tttgtcatca atgcgattat tggaaatgtt     1320
tttggacacc acgatggtgt gtggcgctac atgctggcaa ttgccgcaat cccagcaatt     1380
gccctcttct ttggaatgct ccgagttcca gaatccccac gctggcttgt tgagcgagga     1440
cgcattgatg aggctcgcgc agttcttgaa accattcgcc ctctagaacg tgcccatgca     1500
gaagttgctg atgttgaaca cctagcaaga gaagagcacg ccgtttccga aagtccatg      1560 ggcttaaggg aaattttgtc cagcaagtgg cttgtgcgca tcctcctggt aggtatcgga     1620
ttgggtgtcg cacagcagct gaccggcatc aactccatca tgtactacgg ccaggttgtt     1680
ctcattgagg ctggttttctc cgagaatgca gctctgatcg ccaacgtggc gccaggagtg     1740
atcgcagttg tcggtgcatt catcgcactg tggatgatgg atcgtatcaa ccgccgtacc     1800
accctcatta ccggttattc tctcaccacc attagccacg tattgatcgg tatcgcatcc     1860
gtagcattcc cagtcggcga tcctcttcgc ccctacgtta tcttgactct ggttgtggtc     1920
ttcgtgggat ccatgcagac cttcctcaac gtagctacct gggttatgct ctctgagctc     1980
ttcccgctgg caatgcgcgg tttcgcaatc ggtatctcag tgttcttcct ctggatcgca     2040
aacgcgttcc tcggattgtt cttcccaacc atcatggaag cagtaggact aaccggaacc     2100
ttcttcatgt tcgccggaat cggtgtggtt gccttgatct tcatctacac ccaggttcct     2160
gaaactcgtg gacgtacctt ggaggagatt gatgaggatg ttacttccgg tgtcattttc     2220
aacaaggaca tccgaaaagg aaaggtgcac taa                                  2253
```

<210> SEQ ID NO 4
<211> LENGTH: 491
<212> TYPE: PRT
<213> ORGANISM: Corynebacterium glutamicum
<220> FEATURE:
<221> NAME/KEY: IolT1-Protein
<222> LOCATION: (1)..(491)

<400> SEQUENCE: 4

Met Ala Ser Thr Phe Ile Gln Ala Asp Ser Pro Glu Lys Ser Lys Lys
1               5                   10                  15

Leu Pro Pro Leu Thr Glu Gly Pro Tyr Arg Lys Arg Leu Phe Tyr Val
            20                  25                  30

```
Ala Leu Val Ala Thr Phe Gly Gly Leu Leu Phe Gly Tyr Asp Thr Gly
         35                  40                  45

Val Ile Asn Gly Ala Leu Asn Pro Met Thr Arg Glu Leu Gly Leu Thr
 50                  55                  60

Ala Phe Thr Glu Gly Val Val Thr Ser Ser Leu Leu Phe Gly Ala Ala
 65                  70                  75                  80

Ala Gly Ala Met Phe Phe Gly Arg Ile Ser Asp Asn Trp Gly Arg Arg
                 85                  90                  95

Lys Thr Ile Ile Ser Leu Ala Val Ala Phe Phe Val Gly Thr Met Ile
            100                 105                 110

Cys Val Phe Ala Pro Ser Phe Ala Val Met Val Val Gly Arg Val Leu
            115                 120                 125

Leu Gly Leu Ala Val Gly Gly Ala Ser Thr Val Val Pro Val Tyr Leu
        130                 135                 140

Ala Glu Leu Ala Pro Phe Glu Ile Arg Gly Ser Leu Ala Gly Arg Asn
145                 150                 155                 160

Glu Leu Met Ile Val Val Gly Gln Leu Ala Ala Phe Val Ile Asn Ala
                165                 170                 175

Ile Ile Gly Asn Val Phe Gly His His Asp Gly Val Trp Arg Tyr Met
            180                 185                 190

Leu Ala Ile Ala Ala Ile Pro Ala Ile Ala Leu Phe Phe Gly Met Leu
        195                 200                 205

Arg Val Pro Glu Ser Pro Arg Trp Leu Val Glu Arg Gly Arg Ile Asp
210                 215                 220

Glu Ala Arg Ala Val Leu Glu Thr Ile Arg Pro Leu Glu Arg Ala His
225                 230                 235                 240

Ala Glu Val Ala Asp Val Glu His Leu Ala Arg Glu Glu His Ala Val
                245                 250                 255

Ser Glu Lys Ser Met Gly Leu Arg Glu Ile Leu Ser Ser Lys Trp Leu
            260                 265                 270

Val Arg Ile Leu Leu Val Gly Ile Gly Leu Gly Val Ala Gln Gln Leu
        275                 280                 285

Thr Gly Ile Asn Ser Ile Met Tyr Tyr Gly Gln Val Val Leu Ile Glu
        290                 295                 300

Ala Gly Phe Ser Glu Asn Ala Ala Leu Ile Ala Asn Val Ala Pro Gly
305                 310                 315                 320

Val Ile Ala Val Val Gly Ala Phe Ile Ala Leu Trp Met Met Asp Arg
                325                 330                 335

Ile Asn Arg Arg Thr Thr Leu Ile Thr Gly Tyr Ser Leu Thr Thr Ile
            340                 345                 350

Ser His Val Leu Ile Gly Ile Ala Ser Val Ala Phe Pro Val Gly Asp
        355                 360                 365

Pro Leu Arg Pro Tyr Val Ile Leu Thr Leu Val Val Val Phe Val Gly
370                 375                 380

Ser Met Gln Thr Phe Leu Asn Val Ala Thr Trp Val Met Leu Ser Glu
385                 390                 395                 400

Leu Phe Pro Leu Ala Met Arg Gly Phe Ala Ile Gly Ile Ser Val Phe
                405                 410                 415

Phe Leu Trp Ile Ala Asn Ala Phe Leu Gly Leu Phe Phe Pro Thr Ile
            420                 425                 430

Met Glu Ala Val Gly Leu Thr Gly Thr Phe Phe Met Phe Ala Gly Ile
        435                 440                 445
```

```
Gly Val Val Ala Leu Ile Phe Ile Tyr Thr Gln Val Pro Glu Thr Arg
            450                 455                 460

Gly Arg Thr Leu Glu Glu Ile Asp Glu Asp Val Thr Ser Gly Val Ile
465                 470                 475                 480

Phe Asn Lys Asp Ile Arg Lys Gly Lys Val His
                485                 490

<210> SEQ ID NO 5
<211> LENGTH: 1524
<212> TYPE: DNA
<213> ORGANISM: Corynebacterium glutamicum
<220> FEATURE:
<221> NAME/KEY: iolT2-Gen
<222> LOCATION: (1)..(1524)

<400> SEQUENCE: 5
atgacggaca tcaaggccac atcaagtaca tcggccacta cagcaccaac agcaggccga       60
ccagcgcgtc gacttggaca aatttccctc gtcgcctgtc tcggcggact tctcttcggc      120
tatgacaccg gtgtcgccaa cggcgccgaa ggccacatgg cacaagaact cggactcaac      180
gtgctgcagc tcggcgttgt catcagttca ctggttttcg ctgcagcctt ggcgcgctg       240 ttcgctgggc gtatctcgga cgaaatcggg cgtcgaaaag caattatcac tttgtccgtg      300
ctgttcttcc tcggatcaat cctcgtcgta ttctcccccg ccggtgagct ggggcagttc      360 tacgaccag gatttgccac cttggtcacc gggcgcatca tgttgggtct cgcggttggc       420
ggcgcctcca cagtagttcc ggtgtacctc gctgaactcg caccactaga aatccgcggc      480
tccctgaccg gccgaaacga gcttgctatc gtcaccggcc agctgcttgc cttcgtgatc      540
aacgcgctta tcgccgtcac cctacacgga gttattgatg aatctggcg catcatgttc       600 gccgtctgtg ccctccctgc cgtcgccctc ttcctcggca tgctgcggat gccggaatca      660
ccacgctggc tggtcaacca ggggcgttac gacgacgccc gccgcgtcat ggagaccgtc      720
cgtacccctg agcgtgcgaa agccgaaatg gatgaaatca tcgcggtgca ctctgaaaac      780
aatgcggcac ttcctggtgt taagcagtct tcgggccagg cttcaggcca ggtttctagc      840
aagcacaccc acatgtccat cggcgaagtc ctcagcaaca aatggctggt tcgtctgctc      900
atcgccggca tcggtgttgc agttgcccag cagctcaccg gcatcaacgc catcatgtac      960
tacggaaccc gcgtcctcga ggaatccggc atgagcgcag aaatggctgt ggttgccaac     1020
attgctttcg gtgccgttgc cgtcatcggt ggactgatcg cactgcgcaa catggaccgc     1080
ctggatcgcc gcaccacctt catcatcggc ctgtcactga ccaccacctt ccacttttg      1140 atcgcagctg ccggcactct ccttccagaa ggtaactcca ttcgaccatt cgccatcatg     1200
atccttgttg ttgggttcgt gctctccatg cagactttcc tcaacgttgc agtgtgggtg     1260
tggctggcgg aaatcttccc agtccgaatg aagggtatcg gcaccggtat ttcggtattc     1320
tgcggttggg gcatcaatgg cgtcctagcg ttgttcttcc cagcactggt ctccggcgtg     1380
ggtatcacct tctccttcct tatcttcgca gtcgtcggag tcattgccct ggcgttcgtc     1440
accaagtttg ttcctgaaac ccgtggccgc tcacttgaag aactcgatca cgcagcattc     1500
accggccaga tcttcaagaa ggct                                            1524

<210> SEQ ID NO 6
<211> LENGTH: 508
<212> TYPE: PRT
<213> ORGANISM: Corynebacterium glutamicum
<220> FEATURE:
<221> NAME/KEY: IolT2-Protein
```

<222> LOCATION: (1)..(508)

<400> SEQUENCE: 6

```
Met Thr Asp Ile Lys Ala Thr Ser Ser Thr Ser Ala Thr Thr Ala Pro
1               5                   10                  15

Thr Ala Gly Arg Pro Ala Arg Arg Leu Gly Gln Ile Ser Leu Val Ala
            20                  25                  30

Cys Leu Gly Gly Leu Leu Phe Gly Tyr Asp Thr Gly Val Ala Asn Gly
        35                  40                  45

Ala Glu Gly His Met Ala Gln Glu Leu Gly Leu Asn Val Leu Gln Leu
    50                  55                  60

Gly Val Val Ile Ser Ser Leu Val Phe Ala Ala Phe Gly Ala Leu
65                  70                  75                  80

Phe Ala Gly Arg Ile Ser Asp Glu Ile Gly Arg Arg Lys Ala Ile Ile
                85                  90                  95

Thr Leu Ser Val Leu Phe Phe Leu Gly Ser Ile Leu Val Val Phe Ser
            100                 105                 110

Pro Ala Gly Glu Leu Gly Gln Phe Tyr Gly Pro Gly Phe Ala Thr Leu
        115                 120                 125

Val Thr Gly Arg Ile Met Leu Gly Leu Ala Val Gly Gly Ala Ser Thr
130                 135                 140

Val Val Pro Val Tyr Leu Ala Glu Leu Ala Pro Leu Glu Ile Arg Gly
145                 150                 155                 160

Ser Leu Thr Gly Arg Asn Glu Leu Ala Ile Val Thr Gly Gln Leu Leu
                165                 170                 175

Ala Phe Val Ile Asn Ala Leu Ile Ala Val Thr Leu His Gly Val Ile
            180                 185                 190

Asp Gly Ile Trp Arg Ile Met Phe Ala Val Cys Ala Leu Pro Ala Val
        195                 200                 205

Ala Leu Phe Leu Gly Met Leu Arg Met Pro Glu Ser Pro Arg Trp Leu
    210                 215                 220

Val Asn Gln Gly Arg Tyr Asp Asp Ala Arg Arg Val Met Glu Thr Val
225                 230                 235                 240

Arg Thr Pro Glu Arg Ala Lys Ala Glu Met Asp Glu Ile Ile Ala Val
                245                 250                 255

His Ser Glu Asn Asn Ala Ala Leu Pro Gly Val Lys Gln Ser Ser Gly
            260                 265                 270

Gln Ala Ser Gly Gln Val Ser Ser Lys His Thr His Met Ser Ile Gly
        275                 280                 285

Glu Val Leu Ser Asn Lys Trp Leu Val Arg Leu Leu Ile Ala Gly Ile
    290                 295                 300

Gly Val Ala Val Ala Gln Gln Leu Thr Gly Ile Asn Ala Ile Met Tyr
305                 310                 315                 320

Tyr Gly Thr Arg Val Leu Glu Glu Ser Gly Met Ser Ala Glu Met Ala
                325                 330                 335

Val Val Ala Asn Ile Ala Phe Gly Ala Val Ala Val Ile Gly Gly Leu
            340                 345                 350

Ile Ala Leu Arg Asn Met Asp Arg Leu Asp Arg Arg Thr Thr Phe Ile
        355                 360                 365

Ile Gly Leu Ser Leu Thr Thr Thr Phe His Leu Leu Ile Ala Ala Ala
    370                 375                 380

Gly Thr Leu Leu Pro Glu Gly Asn Ser Ile Arg Pro Phe Ala Ile Met
385                 390                 395                 400
```

```
Ile Leu Val Val Gly Phe Val Leu Ser Met Gln Thr Phe Leu Asn Val
                405                 410                 415

Ala Val Trp Val Trp Leu Ala Glu Ile Phe Pro Val Arg Met Lys Gly
            420                 425                 430

Ile Gly Thr Gly Ile Ser Val Phe Cys Gly Trp Gly Ile Asn Gly Val
        435                 440                 445

Leu Ala Leu Phe Phe Pro Ala Leu Val Ser Gly Val Gly Ile Thr Phe
    450                 455                 460

Ser Phe Leu Ile Phe Ala Val Val Gly Val Ile Ala Leu Ala Phe Val
465                 470                 475                 480

Thr Lys Phe Val Pro Glu Thr Arg Gly Arg Ser Leu Glu Glu Leu Asp
                485                 490                 495

His Ala Ala Phe Thr Gly Gln Ile Phe Lys Lys Ala
                500                 505

<210> SEQ ID NO 7
<211> LENGTH: 1399
<212> TYPE: DNA
<213> ORGANISM: Corynebacterium glutamicum
<220> FEATURE:
<221> NAME/KEY: iolC-Gen mit 5' regulat Bereich Substitution
<222> LOCATION: (383)..(384)
<223> OTHER INFORMATION: Substitution an Pos 383 C->G Substitution an
      Pos 384 A->G

<400> SEQUENCE: 7
gatgtctcct ttcgttgccc acccaacaag ctcatgtaaa tgtgttagga catttgaaca      60
atgtaactga gttgcgggtg gtggtcttgg taaatccgtg ttcatgcagg acttttgtgt     120
catccagggc ttttattgat ctgacattat cacttgcatt agggaatgag tagcgaaact     180
tagtgaaaag ggcagagttt gcaggtcata acgtgcaact tgttaaccc cgcaccttcc      240 aaagcgaggg ggttttcgtc gacaagcaaa atctttgaat gaaaaccggg cgttgccct      300 ggggttttgc gcgttttcgg gaatcgtttt agaaaatttt cggaaatgta ttgctttgtc     360
aggacaatgt gttattgtca tgggatgcga tcgtgagggt cgccacattc catcaaaaat     420
gagtgaaggg ttgcatcgcc acatgactaa cttgacgagc actcacgaag tcctagctat     480
cggccgcttg ggcgtagata tttacccact tcaaagtgga gtaggactgg ccgatgttca     540
atctttcggc aagtacctcg gcggaagcgc agcaaacgtt tctgttgcag ccgcccgcca     600
tggacacaat tccgcactgc tgtcccgtgt gggaaatgat cctttcggcg agtacctgct     660
tgctgagctg gagcgtttgg gcgtggacaa ccagtacgtt gccaccgatc agactttaa     720 gaccccagtg accttctgtg aaattttccc accggatgat ttcccactgt acttctaccg     780
cgaaccaaag gctccggatc tcaatattga atccgcagac gtcagcctgg acgatgtgcg     840
cgaagccgat attttgtggt tcacactcac tggtttcagt gaagagccaa gccgcggcac     900
acaccgcgag atcttgacta ctcgtgcgaa ccgtcgccac accatctttg atctggacta     960
ccgaccaatg ttctgggaat ccccagaaga ggccaccaag caggcggaat gggcgttgca    1020
gcattccacg gtggcggttg gcaacaagga agaatgcgaa atcgcagtgg gcgagaccga    1080
gccagagcgc gcgggccgag cactgttgga acgcggtgtg gagttggcca tcgtcaagca    1140
gggacctaag ggtgtcatgg cgatgaccaa ggacgaaacc gtagaagttc ctccgttctt    1200
cgtcgatgtc atcaacggtc ttggtgccgg cgatgcattc ggcggcgcgc tgtgccacgg    1260
tctgctctct gaatggccgt tggaaaaggt tctccgttt gccaacaccg cgggtgcgct    1320
tgtggcgtcc cgtcttgaat gctccaccgc aatgcctact accgatgagg tggaagcctc    1380
```

```
cctcaaccag aaagtctga                                           1399

<210> SEQ ID NO 8
<211> LENGTH: 1397
<212> TYPE: DNA
<213> ORGANISM: Corynebacterium glutamicum
<220> FEATURE:
<221> NAME/KEY: iolC-Gen mit 5' regulat Bereich Deletion
<222> LOCATION: (383)..(384)
<223> OTHER INFORMATION: Deletion Pos 383 und 384

<400> SEQUENCE: 8
gatgtctcct ttcgttgccc acccaacaag ctcatgtaaa tgtgttagga catttgaaca     60
atgtaactga gttgcgggtg gtggtcttgg taaatccgtg ttcatgcagg acttttgtgt    120
catccagggc ttttattgat ctgacattat cacttgcatt agggaatgag tagcgaaact    180
tagtgaaaag ggcagagttt gcaggtcata acgtgcaact ttgttaaccc cgcaccttcc    240
aaagcgaggg ggttttcgtc gacaagcaaa atctttgaat gaaaaccggg gcgttgccct    300
ggggttttgc gcgttttcgg gaatcgtttt agaaaatttt cggaaatgta ttgctttgtc    360
aggacaatgt gttattgtca tgatgcgatc gtgagggtcg ccacattcca tcaaaaatga    420
gtgaagggtt gcatcgccac atgactaact tgacgagcac tcacgaagtc ctagctatcg    480
gccgcttggg cgtagatatt tacccacttc aaagtggagt aggactggcc gatgttcaat    540
ctttcggcaa gtacctcggc ggaagcgcag caaacgtttc tgttgcagcc gcccgccatg    600
gacacaattc cgcactgctg tcccgtgtgg gaaatgatcc tttcggcgag tacctgcttg    660
ctgagctgga gcgtttgggc gtggacaacc agtacgttgc caccgatcag acttttaaga    720
ccccagtgac cttctgtgaa attttcccac cggatgattt cccactgtac ttctaccgcg    780
aaccaaaggc tccggatctc aatattgaat ccgcagacgc cagcctggac gatgtgcgcg    840
aagccgatat tttgtggttc acactcactg gtttcagtga agagccaagc cgcggcacac    900
accgcgagat cttgactact cgtgcgaacc gtcgccacac catctttgat ctggactacc    960
gaccaatgtt ctgggaatcc ccagaagagg ccaccaagca ggcggaatgg gcgttgcagc   1020
attccacggt ggcggttggc aacaaggaag aatgcgaaat cgcagtgggc gagaccgagc   1080
cagagcgcgc gggccgagca ctgttggaac gcggtgtgga gttggccatc gtcaagcagg   1140
gacctaaggg tgtcatggcg atgaccaagg acgaaaccgt agaagttcct ccgttcttcg   1200
tcgatgtcat caacggtctt ggtgccggcg atgcattcgg cggcgcgctg tgccacggtc   1260
tgctctctga atggccgttg gaaaaggttc tccgttttgc caacaccgcg ggtgcgcttg   1320
tggcgtcccg tcttgaatgc tccaccgcaa tgcctactac cgatgaggtg aagcctccc    1380 tcaaccagaa agtctga                                                 1397

<210> SEQ ID NO 9
<211> LENGTH: 2253
<212> TYPE: DNA
<213> ORGANISM: Corynebacterium glutamicum
<220> FEATURE:
<221> NAME/KEY: iolT1-Gen mit 5' regulat Bereich Substitution
<222> LOCATION: (665)..(666)
<223> OTHER INFORMATION: Substitution an Pos 665 C->G Substitution an
      Pos 666 A->G

<400> SEQUENCE: 9
accttgattg atcatgtcga ggaaagccgt acggctttcc tctgggattg ttctacgaat     60
gcccacttcg caccccttcgg gttgctcgtg gtgcattcac ccctgaacc cgcctagggt    120
```

```
ttgatgcaaa aattcgttcg actttatggc cagacctcac gcctgtggtg aaaaattgat      180
cagcaaacac ccaggtttca cattcgcccc accagtccca aaatgatgac gttccagagc      240
gccgcctgac ggcaatttgt gcccactttg acacaagtgg tcgatcgacg tctcgagccg      300
cttaaacggg cgattatcgc cccaccattc ccgatgtccg ctcctcgcac gcttttttgta     360 atgacattag gatctttaag cagtgaatga ggtgacaatg tcacctaaca aaggtgtcaa     420
acagccccaa tcactacccc ctccaccccc gcacccttat ccagaaactc ccatgctcca     480
acatttccag agggggcagt ttctgacatt aaccacataa ctcctgcatc aaaccgcagc     540
taacagccca ccccctgctg aaaatcccga atggaaaacc atacccaagc agacaccccc     600 accctaagt attaccaatt actcaaaagt attcaaaaaa gtttgttat gtacgattga       660 cgggggatat cgtgtctgcc acgattaaag acattggtga tgtgaatcac tgcctactac     720
atcgtgtttc gtgaccctgc acctccaagt aagggcacga caaacttagg agacaagatg     780
gctagtacct tcattcaggc cgacagccct gaaaaaagta agaagctgcc cccactcaca     840
gaaggtccgt atagaaagcg gctattctac gttgcactag ttgcgacgtt tggtgggctg     900
ctcttcggat atgacaccgg agtaatcaac ggtgcactca acccaatgac acgtgagctc     960
ggactaaccg cgttcaccga gggtgttgta acttcttccc tgctgtttgg tgcagcagct    1020
ggtgcgatgt ttttcggtcg catttccgac aactgggggtc gccggaaaac aatcatctca    1080
cttgcagtag cttctttgt cggcaccatg atctgcgtgt ttgctccatc ttttgcagta     1140
atggttgtcg gacgtgtgct tcttggactc gcagttggtg gcgcttccac tgttgtccct    1200
gtctacctgg ctgaacttgc tccttttgaa atccgtggct cactggctgg ccgtaatgag    1260
ttgatgattg ttgttggtca gctcgcagct tttgtcatca atgcgattat tggaaatgtt    1320
tttggacacc acgatggtgt gtggcgctac atgctggcaa ttgccgcaat cccagcaatt    1380
gccctcttct ttggaatgct ccgagttcca gaatccccac gctggcttgt tgagcgagga    1440
cgcattgatg aggctcgcgc agttcttgaa accattcgcc ctctagaacg tgcccatgca    1500
gaagttgctg atgttgaaca cctagcaaga gaagagcacg ccgtttccga gaagtccatg    1560
ggcttaaggg aaattttgtc cagcaagtgg cttgtgcgca tcctcctggt aggtatcgga    1620
ttgggtgtcg cacagcagct gaccggcatc aactccatca tgtactacgg ccaggttgtt    1680
ctcattgagc tggtttctc cgagaatgca gctctgatcg ccaacgtggc gccaggagtg    1740
atcgcagttg tcggtgcatt catcgcactg tggatgatgg atcgtatcaa ccgccgtacc    1800
accctcatta ccgttattc tctcaccacc attagccacg tattgatcgg tatcgcatcc    1860
gtagcattcc cagtcggcga tcctcttcgc ccctacgtta tcttgactct ggttgtggtc    1920
ttcgtgggat ccatgcagac cttcctcaac gtagctacct gggttatgct ctctgagctc    1980
ttcccgctgg caatgcgcgg tttcgcaatc ggtatctcag tgttcttcct ctggatcgca    2040
aacgcgttcc tcgattgtt cttcccaacc atcatggaag cagtaggact aaccggaacc    2100
ttcttcatgt tcgccggaat cggtgtggtt gccttgatct tcatctacac ccaggttcct    2160
gaaactcgtg gacgtacctt ggaggagatt gatgaggatg ttacttccgg tgtcatttc    2220 aacaaggaca tccgaaaagg aaaggtgcac taa                                  2253

<210> SEQ ID NO 10
<211> LENGTH: 2251
<212> TYPE: DNA
<213> ORGANISM: Corynebacterium glutamicum
<220> FEATURE:
```

<221> NAME/KEY: iolT1-Gen mit 5' regulat Bereich mit Deletion
<222> LOCATION: (665)..(666)
<223> OTHER INFORMATION: Deletion an Pos 665 und 666

<400> SEQUENCE: 10

```
accttgattg atcatgtcga ggaaagccgt acggctttcc tctgggattg ttctacgaat      60
gcccacttcg cacccttcgg gttgctcgtg gtgcattcac ccctgaacc cgcctagggt     120
ttgatgcaaa aattcgttcg actttatggc cagacctcac gcctgtggtg aaaaattgat    180
cagcaaacac ccaggtttca cattcgcccc accagtccca aaatgatgac gttccagagc    240
gccgcctgac ggcaatttgt gcccactttg acacaagtgg tcgatcgacg tctcgagccg    300
cttaaacggg cgattatcgc cccaccattc ccgatgtccg ctcctcgcac gcttttttgta   360
atgacattag gatctttaag cagtgaatga ggtgacaatg tcacctaaca aaggtgtcaa    420
acagccccaa tcactacccc ctccaccccc gcacccttat ccagaaactc ccatgctcca    480
acatttccag aggggggcagt ttctgacatt aaccacataa ctcctgcatc aaaccgcagc   540
taacagccac acccctgctg aaaatcccga atggaaaacc atacccaagc agacacccc    600
accctaagt attaccaatt actcaaaagt attcaaaaaa agtttgttat gtacgattga     660
cgggatatcg tgtctgccac gattaaagac attggtgatg tgaatcactg cctactacat   720
cgtgtttcgt gaccctgcac ctccaagtaa gggcacgaca aacttaggag caagatggc   780
tagtaccttc attcaggccg acagccctga aaaagtaag aagctgcccc cactcacaga    840
aggtccgtat agaaagcggc tattctacgt tgcactagtt gcgacgtttg gtgggctgct    900
cttcggatat gacaccggag taatcaacgg tgcactcaac ccaatgacac gtgagctcgg   960
actaaccgcg ttcaccgagg gtgttgtaac ttcttccctg ctgtttggtg cagcagctgg  1020
tgcgatgttt ttcggtcgca tttccgacaa ctggggtcgc cggaaaacaa tcatctcact  1080
tgcagtagct ttcttttgtcg gcaccatgat ctgcgtgttt gctccatctt ttgcagtaat  1140
ggttgtcgga cgtgtgcttc ttggactcgc agttggtggc gcttccactg ttgtccctgt  1200
ctacctggct gaacttgctc cttttgaaat ccgtggctca ctggctggcc gtaatgagtt  1260
gatgattgtt gttggtcagc tcgcagcttt tgtcatcaat gcgattattg gaaatgtttt  1320
tggacaccac gatggtgtgt ggcgctacat gctggcaatt gccgcaatcc cagcaattgc  1380
cctcttcttt ggaatgctcc gagttccaga atccccacgc tggcttgttg agcgaggacg  1440
cattgatgag gctcgcgcag ttcttgaaac cattcgccct ctagaacgtg cccatgcaga  1500
agttgctgat gttgaacacc tagcaagaga agagcacgcc gtttccgaga agtccatggg  1560
cttaagggaa attttgtcca gcaagtggct tgtgcgcatc ctcctggtag gtatcggatt  1620
gggtgtcgca cagcagctga ccggcatcaa ctccatcatg tactacggcc aggttgttct  1680
cattgaggct ggtttctccg agaatgcagc tctgatcgcc aacgtggcgc caggagtgat  1740
cgcagttgtc ggtgcattca tcgcactgtg gatgatggat cgtatcaacc gccgtaccac  1800
cctcattacc ggttattctc tcaccaccat tagccacgta ttgatcggta tcgcatccgt  1860
agcattccca gtcggcgatc ctcttcgccc ctacgttatc ttgactctgg ttgtggtctt  1920
cgtgggatcc atgcagacct tcctcaacgt agctacctgg gttatgctct ctgagctctt  1980
cccgctggca atgcgcggtt tcgcaatcgg tatctcagtg ttcttcctct ggatcgcaaa  2040
cgcgttcctc ggattgttct tcccaaccat catggaagca gtaggactaa ccggaacctt  2100
cttcatgttc gccggaatcg gtgtggttgc cttgatcttc atctacaccc aggttcctga  2160
aactcgtgga cgtaccttgg aggagattga tgaggatgtt acttccggtg tcatttcaa   2220
```

```
caaggacatc cgaaaaggaa aggtgcacta a                              2251
```

<210> SEQ ID NO 11
<211> LENGTH: 42
<212> TYPE: DNA
<213> ORGANISM: Unknown
<220> FEATURE:
<223> OTHER INFORMATION: artificial
<220> FEATURE:
<221> NAME/KEY: PromiolT1_fw_fw
<222> LOCATION: (1)..(42)
<223> OTHER INFORMATION: Primer

<400> SEQUENCE: 11

```
tgcatgcctg caggtcgact gaaaaattga tcagcaaaca cc                  42
```

<210> SEQ ID NO 12
<211> LENGTH: 38
<212> TYPE: DNA
<213> ORGANISM: Unknown
<220> FEATURE:
<223> OTHER INFORMATION: primer
<220> FEATURE:
<221> NAME/KEY: PromiolT1fw_rev
<222> LOCATION: (1)..(38)
<223> OTHER INFORMATION: Primer

<400> SEQUENCE: 12

```
ggcagacacg atatcccccg tcaatcgtac atagggaa                       38
```

<210> SEQ ID NO 13
<211> LENGTH: 30
<212> TYPE: DNA
<213> ORGANISM: Unknown
<220> FEATURE:
<223> OTHER INFORMATION: primer
<220> FEATURE:
<221> NAME/KEY: Piolt1_rev_fw
<222> LOCATION: (1)..(30)
<223> OTHER INFORMATION: Primer

<400> SEQUENCE: 13

```
cgggggatat cgtgtctgcc acgattaaag                                30
```

<210> SEQ ID NO 14
<211> LENGTH: 38
<212> TYPE: DNA
<213> ORGANISM: Unknown
<220> FEATURE:
<223> OTHER INFORMATION: primer
<220> FEATURE:
<221> NAME/KEY: piolt1_rev_rev
<222> LOCATION: (1)..(38)
<223> OTHER INFORMATION: Primer

<400> SEQUENCE: 14

```
ttgtaaaacg acggccagtg gagtccaaga agcacacg                       38
```

<210> SEQ ID NO 15
<211> LENGTH: 24
<212> TYPE: DNA
<213> ORGANISM: Unknown
<220> FEATURE:
<223> OTHER INFORMATION: primer
<220> FEATURE:
<221> NAME/KEY: checkPromiolT1fw
<222> LOCATION: (1)..(24)
<223> OTHER INFORMATION: Primer

<400> SEQUENCE: 15
tacgaatgcc cacttcgcac cctt                                              24

<210> SEQ ID NO 16
<211> LENGTH: 26
<212> TYPE: DNA
<213> ORGANISM: Unknown
<220> FEATURE:
<223> OTHER INFORMATION: primer
<220> FEATURE:
<221> NAME/KEY: checkPromiolT1rev
<222> LOCATION: (1)..(26)
<223> OTHER INFORMATION: Primer

<400> SEQUENCE: 16
caactcatta cggccagcca gtgagc                                            26

<210> SEQ ID NO 17
<211> LENGTH: 38
<212> TYPE: DNA
<213> ORGANISM: Unknown
<220> FEATURE:
<223> OTHER INFORMATION: primer
<220> FEATURE:
<221> NAME/KEY: PO13 iolC fw
<222> LOCATION: (1)..(38)
<223> OTHER INFORMATION: Primer

<400> SEQUENCE: 17
tgcatgcctg caggtcgact ggatgccgtc ttcgaggc                                38

<210> SEQ ID NO 18
<211> LENGTH: 33
<212> TYPE: DNA
<213> ORGANISM: Unknown
<220> FEATURE:
<223> OTHER INFORMATION: primer
<220> FEATURE:
<221> NAME/KEY: PO13 iolC rev
<222> LOCATION: (1)..(33)
<223> OTHER INFORMATION: Primer

<400> SEQUENCE: 18
gaccctcacg atcgcatccc atgacaataa cac                                    33

<210> SEQ ID NO 19
<211> LENGTH: 29
<212> TYPE: DNA
<213> ORGANISM: Unknown
<220> FEATURE:
<223> OTHER INFORMATION: primer
<220> FEATURE:
<221> NAME/KEY: PO13 iolC rev_fw
<222> LOCATION: (1)..(29)
<223> OTHER INFORMATION: Primer

<400> SEQUENCE: 19
gggatgcgat cgtgagggtc gccacattc                                         29

<210> SEQ ID NO 20
<211> LENGTH: 42
<212> TYPE: DNA
<213> ORGANISM: Unknown
<220> FEATURE:
<223> OTHER INFORMATION: primer
<220> FEATURE:
<221> NAME/KEY: PO13 iolC rev_rev
<222> LOCATION: (1)..(42)
<223> OTHER INFORMATION: Primer

<400> SEQUENCE: 20
ttgtaaaacg acggccagtg cttggctctt cactgaaacc ag                          42

<210> SEQ ID NO 21
<211> LENGTH: 25
<212> TYPE: DNA
<213> ORGANISM: Unknown
<220> FEATURE:
<223> OTHER INFORMATION: primer
<220> FEATURE:
<221> NAME/KEY: Check Prom iolC fw
<222> LOCATION: (1)..(25)
<223> OTHER INFORMATION: Primer

<400> SEQUENCE: 21
tctcgttttc taggcgtgct ccggg                                             25

<210> SEQ ID NO 22
<211> LENGTH: 22
<212> TYPE: DNA
<213> ORGANISM: Unknown
<220> FEATURE:
<223> OTHER INFORMATION: primer
<220> FEATURE:
<221> NAME/KEY: Check Prom iolC_rev
<222> LOCATION: (1)..(22)
<223> OTHER INFORMATION: Primer

<400> SEQUENCE: 22
cgacggttcg cacgagtagt ca                                                22

<210> SEQ ID NO 23
<211> LENGTH: 38
<212> TYPE: DNA
<213> ORGANISM: Unknown
<220> FEATURE:
<223> OTHER INFORMATION: Primer
<220> FEATURE:
<221> NAME/KEY: DPO6iolT1_Fw_fw
<222> LOCATION: (1)..(38)
<223> OTHER INFORMATION: Primer

<400> SEQUENCE: 23
tgcatgcctg caggtcgact aattgatcag caaacacc                               38

<210> SEQ ID NO 24
<211> LENGTH: 29
<212> TYPE: DNA
<213> ORGANISM: Unknown
<220> FEATURE:
<223> OTHER INFORMATION: Primer
<220> FEATURE:
<221> NAME/KEY: DPO6iolT1_Fw_rev
<222> LOCATION: (1)..(29)
<223> OTHER INFORMATION: Primer

<400> SEQUENCE: 24
atcgtggcag acacgatatc ccgtcaatc                                         29

<210> SEQ ID NO 25
<211> LENGTH: 31
<212> TYPE: DNA
<213> ORGANISM: Unknown
<220> FEATURE:
<223> OTHER INFORMATION: Primer
<220> FEATURE:
<221> NAME/KEY: DPO6iolT1_rev_fw
<222> LOCATION: (1)..(31)

<223> OTHER INFORMATION: Primer

<400> SEQUENCE: 25
gatatcgtgt ctgccacgat taaagacatt g                                    31

<210> SEQ ID NO 26
<211> LENGTH: 38
<212> TYPE: DNA
<213> ORGANISM: Unknown
<220> FEATURE:
<223> OTHER INFORMATION: Primer
<220> FEATURE:
<221> NAME/KEY: DPO6iolT1_rev_rev
<222> LOCATION: (1)..(38)
<223> OTHER INFORMATION: Primer

<400> SEQUENCE: 26
ttgtaaaacg acggccagtg actgcgagtc caagaagc                             38

<210> SEQ ID NO 27
<211> LENGTH: 38
<212> TYPE: DNA
<213> ORGANISM: Unknown
<220> FEATURE:
<223> OTHER INFORMATION: Primer
<220> FEATURE:
<221> NAME/KEY: DPO13iolC_fw_fw
<222> LOCATION: (1)..(38)
<223> OTHER INFORMATION: Primer

<400> SEQUENCE: 27
tgcatgcctg caggtcgact ccgtcttcga ggcgttgg                             38

<210> SEQ ID NO 28
<211> LENGTH: 28
<212> TYPE: DNA
<213> ORGANISM: Unknown
<220> FEATURE:
<223> OTHER INFORMATION: Primer
<220> FEATURE:
<221> NAME/KEY: DPO13iolC_fw_rev
<222> LOCATION: (1)..(28)
<223> OTHER INFORMATION: Primer

<400> SEQUENCE: 28
gtggcgaccc tcacgatcgc atcccatg                                        28

<210> SEQ ID NO 29
<211> LENGTH: 28
<212> TYPE: DNA
<213> ORGANISM: Unknown
<220> FEATURE:
<223> OTHER INFORMATION: Primer
<220> FEATURE:
<221> NAME/KEY: DPO13iolC_rev_fw
<222> LOCATION: (1)..(28)
<223> OTHER INFORMATION: Primer

<400> SEQUENCE: 29
gcgatcgtga gggtcgccac attccatc                                        28

<210> SEQ ID NO 30
<211> LENGTH: 38
<212> TYPE: DNA
<213> ORGANISM: Unknown
<220> FEATURE:
<223> OTHER INFORMATION: Primer
<220> FEATURE:
<221> NAME/KEY: DPO13iolC_rev_rev -continued
<222> LOCATION: (1)..(38)
<223> OTHER INFORMATION: Primer

<400> SEQUENCE: 30
ttgtaaaacg acggccagtg cgcggcttgg ctcttcac         38

<210> SEQ ID NO 31
<211> LENGTH: 39
<212> TYPE: DNA
<213> ORGANISM: Unknown
<220> FEATURE:
<223> OTHER INFORMATION: Primer
<220> FEATURE:
<221> NAME/KEY: iolG vorne fw
<222> LOCATION: (1)..(39)
<223> OTHER INFORMATION: Primer

<400> SEQUENCE: 31
tgcatgcctg caggtcgact gaagagttcg gcatgaagc        39

<210> SEQ ID NO 32
<211> LENGTH: 34
<212> TYPE: DNA
<213> ORGANISM: Unknown
<220> FEATURE:
<223> OTHER INFORMATION: Primer
<220> FEATURE:
<221> NAME/KEY: iolG vorne rev
<222> LOCATION: (1)..(34)
<223> OTHER INFORMATION: Primer

<400> SEQUENCE: 32
tactcccggg catatggcga aggctcttgc tcat             34

<210> SEQ ID NO 33
<211> LENGTH: 52
<212> TYPE: DNA
<213> ORGANISM: Unknown
<220> FEATURE:
<223> OTHER INFORMATION: Primer
<220> FEATURE:
<221> NAME/KEY: iolG hinten fw
<222> LOCATION: (1)..(52)
<223> OTHER INFORMATION: Primer

<400> SEQUENCE: 33
gagccttcgc catatgcccg ggagtactgg atccgttgat gcggcacctc gc    52

<210> SEQ ID NO 34
<211> LENGTH: 43
<212> TYPE: DNA
<213> ORGANISM: Unknown
<220> FEATURE:
<223> OTHER INFORMATION: Primer
<220> FEATURE:
<221> NAME/KEY: iolG hinten rev
<222> LOCATION: (1)..(43)
<223> OTHER INFORMATION: Primer

<400> SEQUENCE: 34
ttgtaaaacg acggccagtg atgactcgcc atgcttcaat acc    43

<210> SEQ ID NO 35
<211> LENGTH: 25
<212> TYPE: DNA
<213> ORGANISM: Unknown
<220> FEATURE:
<223> OTHER INFORMATION: Primer
<220> FEATURE:

<221> NAME/KEY: check iolG fw
<222> LOCATION: (1)..(25)
<223> OTHER INFORMATION: Primer

<400> SEQUENCE: 35
cgacgttgct ggtcttgctt ccaag                                          25

<210> SEQ ID NO 36
<211> LENGTH: 25
<212> TYPE: DNA
<213> ORGANISM: Unknown
<220> FEATURE:
<223> OTHER INFORMATION: Primer
<220> FEATURE:
<221> NAME/KEY: check iolG rev
<222> LOCATION: (1)..(25)
<223> OTHER INFORMATION: Primer

<400> SEQUENCE: 36
ggttagtgat gtagcgcagg ccgtg                                          25

<210> SEQ ID NO 37
<211> LENGTH: 41
<212> TYPE: DNA
<213> ORGANISM: Unknown
<220> FEATURE:
<223> OTHER INFORMATION: Primer
<220> FEATURE:
<221> NAME/KEY: NCS_PTuf_fw
<222> LOCATION: (1)..(41)
<223> OTHER INFORMATION: Primer

<400> SEQUENCE: 37
tttaaattgt gtccatgagg cacagggtag ctggtagttt g                        41

<210> SEQ ID NO 38
<211> LENGTH: 30
<212> TYPE: DNA
<213> ORGANISM: Unknown
<220> FEATURE:
<223> OTHER INFORMATION: Primer
<220> FEATURE:
<221> NAME/KEY: NCS_PTuf_rev
<222> LOCATION: (1)..(30)
<223> OTHER INFORMATION: Primer

<400> SEQUENCE: 38
tcttgctcat acgcgttcct cctggacttc                                     30

<210> SEQ ID NO 39
<211> LENGTH: 28
<212> TYPE: DNA
<213> ORGANISM: Unknown
<220> FEATURE:
<223> OTHER INFORMATION: Primer
<220> FEATURE:
<221> NAME/KEY: NCS_Ptuf_iolG_fw
<222> LOCATION: (1)..(28)
<223> OTHER INFORMATION: Primer

<400> SEQUENCE: 39
aggaacgcgt atgagcaaga gccttcgc                                       28

<210> SEQ ID NO 40
<211> LENGTH: 40
<212> TYPE: DNA
<213> ORGANISM: Unknown
<220> FEATURE:
<223> OTHER INFORMATION: Primer

```
<220> FEATURE:
<221> NAME/KEY: NCS_Ptuf_iolG_rev
<222> LOCATION: (1)..(40)
<223> OTHER INFORMATION: Primer

<400> SEQUENCE: 40
cgaagcatat gcccgggagt ttaagcgtag aaatctgggc                    40

<210> SEQ ID NO 41
<211> LENGTH: 26
<212> TYPE: DNA
<213> ORGANISM: Unknown
<220> FEATURE:
<223> OTHER INFORMATION: Primer
<220> FEATURE:
<221> NAME/KEY: NCS check fw
<222> LOCATION: (1)..(26)
<223> OTHER INFORMATION: Primer

<400> SEQUENCE: 41
cggaatgatc ttgacccttg ttggtg                                   26

<210> SEQ ID NO 42
<211> LENGTH: 26
<212> TYPE: DNA
<213> ORGANISM: Unknown
<220> FEATURE:
<223> OTHER INFORMATION: Primer
<220> FEATURE:
<221> NAME/KEY: NCS check rev
<222> LOCATION: (1)..(26)
<223> OTHER INFORMATION: Primer

<400> SEQUENCE: 42
atcaagcaga tctctgagct gctggc                                   26

<210> SEQ ID NO 43
<211> LENGTH: 38
<212> TYPE: DNA
<213> ORGANISM: Unknown
<220> FEATURE:
<223> OTHER INFORMATION: Primer
<220> FEATURE:
<221> NAME/KEY: CgLP4_fw_fw
<222> LOCATION: (1)..(38)
<223> OTHER INFORMATION: Primer

<400> SEQUENCE: 43
tgcatgcctg caggtcgact cttctgggtc ggcgatac                      38

<210> SEQ ID NO 44
<211> LENGTH: 30
<212> TYPE: DNA
<213> ORGANISM: Unknown
<220> FEATURE:
<223> OTHER INFORMATION: Primer
<220> FEATURE:
<221> NAME/KEY: CgLP4_fw_rev
<222> LOCATION: (1)..(30)
<223> OTHER INFORMATION: Primer

<400> SEQUENCE: 44
ctaccctgtg catcaaaaaa tccgccgttc                               30

<210> SEQ ID NO 45
<211> LENGTH: 31
<212> TYPE: DNA
<213> ORGANISM: Unknown
<220> FEATURE:
```

<223> OTHER INFORMATION: Primer
<220> FEATURE:
<221> NAME/KEY: CgLP4_PTuf_fw
<222> LOCATION: (1)..(31)
<223> OTHER INFORMATION: Primer

<400> SEQUENCE: 45 tttttttgatg cacagggtag ctggtagttt g                                                          31

<210> SEQ ID NO 46
<211> LENGTH: 30
<212> TYPE: DNA
<213> ORGANISM: Unknown
<220> FEATURE:
<223> OTHER INFORMATION: Primer
<220> FEATURE:
<221> NAME/KEY: CgLP4_PTuf_rev
<222> LOCATION: (1)..(30)
<223> OTHER INFORMATION: Primer

<400> SEQUENCE: 46
tcttgctcat acgcgttcct cctggacttc                                                             30

<210> SEQ ID NO 47
<211> LENGTH: 28
<212> TYPE: DNA
<213> ORGANISM: Unknown
<220> FEATURE:
<223> OTHER INFORMATION: Primer
<220> FEATURE:
<221> NAME/KEY: CgLP4_iolG_fw
<222> LOCATION: (1)..(28)
<223> OTHER INFORMATION: Primer

<400> SEQUENCE: 47
aggaacgcgt atgagcaaga gccttcgc                                                               28

<210> SEQ ID NO 48
<211> LENGTH: 30
<212> TYPE: DNA
<213> ORGANISM: Unknown
<220> FEATURE:
<223> OTHER INFORMATION: Primer
<220> FEATURE:
<221> NAME/KEY: CgLP4_iolG_rev
<222> LOCATION: (1)..(30)
<223> OTHER INFORMATION: Primer

<400> SEQUENCE: 48
ctcacttagt ttaagcgtag aaatctgggc                                                             30

<210> SEQ ID NO 49
<211> LENGTH: 28
<212> TYPE: DNA
<213> ORGANISM: Unknown
<220> FEATURE:
<223> OTHER INFORMATION: Primer
<220> FEATURE:
<221> NAME/KEY: CgLP4_rev_fw
<222> LOCATION: (1)..(28)
<223> OTHER INFORMATION: Primer

<400> SEQUENCE: 49
ctacgcttaa actaagtgag tttggatg                                                               28

<210> SEQ ID NO 50
<211> LENGTH: 40
<212> TYPE: DNA
<213> ORGANISM: Unknown

```
<220> FEATURE:
<223> OTHER INFORMATION: Primer
<220> FEATURE:
<221> NAME/KEY: CgLP4_rev_rev
<222> LOCATION: (1)..(40)
<223> OTHER INFORMATION: Primer

<400> SEQUENCE: 50
ttgtaaaacg acggccagtg tagtacgcgg ataaatgatc                              40

<210> SEQ ID NO 51
<211> LENGTH: 22
<212> TYPE: DNA
<213> ORGANISM: Unknown
<220> FEATURE:
<223> OTHER INFORMATION: Primer
<220> FEATURE:
<221> NAME/KEY: CgLP4_Check_fw
<222> LOCATION: (1)..(22)
<223> OTHER INFORMATION: Primer

<400> SEQUENCE: 51
tgcaggtcac tgtggaaaat cg                                                 22

<210> SEQ ID NO 52
<211> LENGTH: 24
<212> TYPE: DNA
<213> ORGANISM: Unknown
<220> FEATURE:
<223> OTHER INFORMATION: Primer
<220> FEATURE:
<221> NAME/KEY: CgLP4_Check_rev
<222> LOCATION: (1)..(24)
<223> OTHER INFORMATION: Primer

<400> SEQUENCE: 52
aatcagcatc acccatccct tcac                                               24

<210> SEQ ID NO 53
<211> LENGTH: 40
<212> TYPE: DNA
<213> ORGANISM: Unknown
<220> FEATURE:
<223> OTHER INFORMATION: Primer
<220> FEATURE:
<221> NAME/KEY: CgLP12_fw_fw
<222> LOCATION: (1)..(40)
<223> OTHER INFORMATION: Primer

<400> SEQUENCE: 53
tgcatgcctg caggtcgact cgttgaagac tccgtcaaac                              40

<210> SEQ ID NO 54
<211> LENGTH: 30
<212> TYPE: DNA
<213> ORGANISM: Unknown
<220> FEATURE:
<223> OTHER INFORMATION: Primer
<220> FEATURE:
<221> NAME/KEY: CgLP12_fw_rev
<222> LOCATION: (1)..(30)
<223> OTHER INFORMATION: Primer

<400> SEQUENCE: 54
ctaccctgtg atatgccgat tgcaagaaac                                         30

<210> SEQ ID NO 55
<211> LENGTH: 31
<212> TYPE: DNA
```

```
<213> ORGANISM: Unknown
<220> FEATURE:
<223> OTHER INFORMATION: Primer
<220> FEATURE:
<221> NAME/KEY: CgLP12_PTuf_fw
<222> LOCATION: (1)..(31)
<223> OTHER INFORMATION: Primer

<400> SEQUENCE: 55
atcggcatat cacagggtag ctggtagttt g                               31

<210> SEQ ID NO 56
<211> LENGTH: 30
<212> TYPE: DNA
<213> ORGANISM: Unknown
<220> FEATURE:
<223> OTHER INFORMATION: Primer
<220> FEATURE:
<221> NAME/KEY: CgLP12_PTuf_rev
<222> LOCATION: (1)..(30)
<223> OTHER INFORMATION: Primer

<400> SEQUENCE: 56
tcttgctcat acgcgttcct cctggacttc                                 30

<210> SEQ ID NO 57
<211> LENGTH: 28
<212> TYPE: DNA
<213> ORGANISM: Unknown
<220> FEATURE:
<223> OTHER INFORMATION: Primer
<220> FEATURE:
<221> NAME/KEY: CgLP12_iolG_fw
<222> LOCATION: (1)..(28)
<223> OTHER INFORMATION: Primer

<400> SEQUENCE: 57
aggaacgcgt atgagcaaga gccttcgc                                   28

<210> SEQ ID NO 58
<211> LENGTH: 33
<212> TYPE: DNA
<213> ORGANISM: Unknown
<220> FEATURE:
<223> OTHER INFORMATION: Primer
<220> FEATURE:
<221> NAME/KEY: CgLP12_iolG_rev
<222> LOCATION: (1)..(33)
<223> OTHER INFORMATION: Primer

<400> SEQUENCE: 58 atttttgac tgattaagcg tagaaatctg ggc                              33

<210> SEQ ID NO 59
<211> LENGTH: 34
<212> TYPE: DNA
<213> ORGANISM: Unknown
<220> FEATURE:
<223> OTHER INFORMATION: Primer
<220> FEATURE:
<221> NAME/KEY: CgLP12_rev_fw
<222> LOCATION: (1)..(34)
<223> OTHER INFORMATION: Primer

<400> SEQUENCE: 59
ctacgcttaa tcagtcaaaa aatgttgaaa tcag                            34

<210> SEQ ID NO 60
<211> LENGTH: 39
```

```
<212> TYPE: DNA
<213> ORGANISM: Unknown
<220> FEATURE:
<223> OTHER INFORMATION: Primer
<220> FEATURE:
<221> NAME/KEY: CgLP12_rev_rev
<222> LOCATION: (1)..(39)
<223> OTHER INFORMATION: Primer

<400> SEQUENCE: 60
ttgtaaaacg acggccagtg ttggcgcttc tttgaagag                    39

<210> SEQ ID NO 61
<211> LENGTH: 25
<212> TYPE: DNA
<213> ORGANISM: Unknown
<220> FEATURE:
<223> OTHER INFORMATION: Primer
<220> FEATURE:
<221> NAME/KEY: CgLP12_Check_Fw
<222> LOCATION: (1)..(25)
<223> OTHER INFORMATION: Primer

<400> SEQUENCE: 61
ctcaaggtca tccgtgaaat gtggc                                  25

<210> SEQ ID NO 62
<211> LENGTH: 24
<212> TYPE: DNA
<213> ORGANISM: Unknown
<220> FEATURE:
<223> OTHER INFORMATION: Primer
<220> FEATURE:
<221> NAME/KEY: CgLP12_Check_Rev
<222> LOCATION: (1)..(24)
<223> OTHER INFORMATION: Primer

<400> SEQUENCE: 62
ttggctttcc atgctttgag gact                                   24

<210> SEQ ID NO 63
<211> LENGTH: 1399
<212> TYPE: DNA
<213> ORGANISM: Corynebacterium glutamicum
<220> FEATURE:
<221> NAME/KEY: iolC-Gen mit 5' regulat Bereich Substitution
<222> LOCATION: (143)..(212)
<223> OTHER INFORMATION: Substitution an Pos 143 (A->G) Substitution an
      Pos 144 (C->G) Substitution an Pos 211 (A->G) Substitution an Pos
      212 (C->G)

<400> SEQUENCE: 63
gatgtctcct ttcgttgccc acccaacaag ctcatgtaaa tgtgttagga catttgaaca    60
atgtaactga gttgcgggtg gtggtcttgg taaatccgtg ttcatgcagg acttttgtgt   120
catccagggc ttttattgat ctgggattat cacttgcatt agggaatgag tagcgaaact   180
tagtgaaaag ggcagagttt gcaggtcata gggtgcaact tgttaaccc cgcaccttcc    240 aaagcgaggg ggttttcgtc gacaagcaaa atctttgaat gaaaaccggg gcgttgccct   300
ggggttttgc gcgttttcgg gaatcgtttt agaaaatttt cggaaatgta ttgctttgtc   360
aggacaatgt gttattgtca tgacatgcga tcgtgagggt cgccacattc catcaaaaat   420
gagtgaaggg ttgcatcgcc acatgactaa cttgacgagc actcacgaag tcctagctat   480
cggccgcttg ggcgtagata tttacccact tcaaagtgga gtaggactgg ccgatgttca   540
atctttcggc aagtacctcg gcggaagcgc agcaaacgtt tctgttgcag ccgcccgcca   600
```

```
tggacacaat tccgcactgc tgtcccgtgt gggaaatgat cctttcggcg agtacctgct    660
tgctgagctg gagcgtttgg gcgtggacaa ccagtacgtt gccaccgatc agactttaa     720 gaccccagtg accttctgtg aaattttccc accggatgat ttcccactgt acttctaccg    780
cgaaccaaag gctccggatc tcaatattga atccgcagac gtcagcctgg acgatgtgcg    840
cgaagccgat attttgtggt tcacactcac tggtttcagt gaagagccaa gccgcggcac    900
acaccgcgag atcttgacta ctcgtgcgaa ccgtcgccac accatctttg atctggacta    960
ccgaccaatg ttctgggaat ccccagaaga ggccaccaag caggcggaat gggcgttgca   1020
gcattccacg gtggcggttg gcaacaagga agaatgcgaa atcgcagtgg gcagaccga    1080 gccagagcgc gcgggccgag cactgttgga acgcggtgtg gagttggcca tcgtcaagca   1140
gggacctaag ggtgtcatgg cgatgaccaa ggacgaaacc gtagaagttc ctccgttctt   1200
cgtcgatgtc atcaacggtc ttggtgccgg cgatgcattc ggcggcgcgc tgtgccacgg   1260
tctgctctct gaatggccgt tggaaaaggt tctccgtttt gccaacaccg cgggtgcgct   1320
tgtggcgtcc cgtcttgaat gctccaccgc aatgcctact accgatgagg tggaagcctc   1380
cctcaaccag aaagtctga                                                1399
```

<210> SEQ ID NO 64
<211> LENGTH: 1395
<212> TYPE: DNA
<213> ORGANISM: Corynebacterium glutamicum
<220> FEATURE:
<221> NAME/KEY: iolC-Gen mit 5' regulat Bereich Deletion
<222> LOCATION: (143)..(212)
<223> OTHER INFORMATION: Deletion an Pos 143, Pos 144, Pos 211 und Pos 212

<400> SEQUENCE: 64

```
gatgtctcct ttcgttgccc acccaacaag ctcatgtaaa tgtgttagga catttgaaca     60
atgtaactga gttgcgggtg gtggtcttgg taaatccgtg ttcatgcagg acttttgtgt    120
catccagggc tttattgat ctgattatca cttgcattag gaatgagta gcgaaactta     180 gtgaaaaggg cagagtttgc aggtcatagt gcaactttgt taaccccgca ccttccaaag    240 cgaggggtt tcgtcgaca agcaaaatct ttgaatgaaa accggggcgt tgccctgggg     300
ttttgcgcgt tttcgggaat cgttttagaa aattttcgga aatgtattgc tttgtcagga    360
caatgtgtta ttgtcatgac atgcgatcgt gagggtcgcc acattccatc aaaaatgagt    420
gaagggttgc atcgccacat gactaacttg acgagcactc acgaagtcct agctatcggc    480
cgcttgggcg tagatattta cccacttcaa agtggagtag gactggccga tgttcaatct    540
ttcggcaagt acctcggcgg aagcgcagca acgtttctg ttgcagccgc cgccatgga     600 cacaattccg cactgctgtc ccgtgtggga atgatccctt cggcgagta cctgcttgct    660 gagctggagc gtttgggcgt ggacaaccag tacgttgcca ccgatcagac ttttaagacc    720
ccagtgacct tctgtgaaat ttcccaccg atgatttcc cactgtactt ctaccgcgaa    780
ccaaaggctc cggatctcaa tattgaatcc gcagacgtca gcctggacga tgtgcgcgaa    840
gccgatattt tgtggttcac actcactggt ttcagtgaag agccaagccg gcacacac     900 cgcgagatct tgactactcg tgcgaaccgt cgccacacca tctttgatct ggactaccga    960
ccaatgttct gggaatcccc agaagaggcc accaagcagg cggaatgggc gttgcagcat   1020
tccacggtgg cggttggcaa caaggaagaa tgcgaaatcg cagtgggcga gaccgagcca   1080
gagcgcgcgg gccgagcact gttggaacgc ggtgtggagt tggccatcgt caagcaggga   1140
```

```
cctaagggtg tcatggcgat gaccaaggac gaaaccgtag aagttcctcc gttcttcgtc    1200
gatgtcatca acggtcttgg tgccggcgat gcattcggcg gcgcgctgtg ccacggtctg    1260
ctctctgaat ggccgttgga aaaggttctc cgttttgcca acaccgcggg tgcgcttgtg    1320
gcgtcccgtc ttgaatgctc caccgcaatg cctactaccg atgaggtgga agcctccctc    1380
aaccagaaag tctga                                                     1395
```

```
<210> SEQ ID NO 65
<211> LENGTH: 39
<212> TYPE: DNA
<213> ORGANISM: Artificial Sequence
<220> FEATURE:
<223> OTHER INFORMATION: Primer
<220> FEATURE:
<221> NAME/KEY: PO5-PO9 iolC_fw_fw
<222> LOCATION: (1)..(39)
<223> OTHER INFORMATION: Primer

<400> SEQUENCE: 65
tgcatgcctg caggtcgact ggttggcgtt tttgaggtc                            39

<210> SEQ ID NO 66
<211> LENGTH: 51
<212> TYPE: DNA
<213> ORGANISM: Artificial Sequence
<220> FEATURE:
<223> OTHER INFORMATION: Primer
<220> FEATURE:
<221> NAME/KEY: PO5-PO9 iolC_fw_rev
<222> LOCATION: (1)..(51)
<223> OTHER INFORMATION: Primer

<400> SEQUENCE: 66
taagtttcgc tactcattcc ctaatgcaag tgataatccc agatcaataa a              51

<210> SEQ ID NO 67
<211> LENGTH: 56
<212> TYPE: DNA
<213> ORGANISM: Artificial Sequence
<220> FEATURE:
<223> OTHER INFORMATION: Primer
<220> FEATURE:
<221> NAME/KEY: PO5-PO9 iolC_rev_fw
<222> LOCATION: (1)..(56)
<223> OTHER INFORMATION: Primer

<400> SEQUENCE: 67
ggaatgagta gcgaaactta gtgaaaaggg cagagtttgc aggtcatagg gtgcaa        56

<210> SEQ ID NO 68
<211> LENGTH: 38
<212> TYPE: DNA
<213> ORGANISM: Artificial Sequence
<220> FEATURE:
<223> OTHER INFORMATION: Primer
<220> FEATURE:
<221> NAME/KEY: PO5-PO9 iolC_rev_rev
<222> LOCATION: (1)..(38)
<223> OTHER INFORMATION: Primer

<400> SEQUENCE: 68
ttgtaaaacg acggccagtg tccagctcag caagcagg                            38

<210> SEQ ID NO 69
<211> LENGTH: 25
<212> TYPE: DNA
<213> ORGANISM: Artificial Sequence
```

```
<220> FEATURE:
<223> OTHER INFORMATION: Primer
<220> FEATURE:
<221> NAME/KEY: PO5-PO9 iolC_check_fw
<222> LOCATION: (1)..(25)
<223> OTHER INFORMATION: Primer

<400> SEQUENCE: 69
gagttttcct gcgatggcgg aactt                                 25

<210> SEQ ID NO 70
<211> LENGTH: 25
<212> TYPE: DNA
<213> ORGANISM: Artificial Sequence
<220> FEATURE:
<223> OTHER INFORMATION: Primer
<220> FEATURE:
<221> NAME/KEY: PO5-PO9 iolC_check_rev
<222> LOCATION: (1)..(25)
<223> OTHER INFORMATION: Primer

<400> SEQUENCE: 70
ggggtcttaa aagtctgatc ggtgg                                 25

<210> SEQ ID NO 71
<211> LENGTH: 39
<212> TYPE: DNA
<213> ORGANISM: Artificial Sequence
<220> FEATURE:
<223> OTHER INFORMATION: Primer
<220> FEATURE:
<221> NAME/KEY: dPO5-PO9iolC_fw_fw
<222> LOCATION: (1)..(38)
<223> OTHER INFORMATION: Primer

<400> SEQUENCE: 71
tgcatgcctg caggtcgact ggttggcgtt tttgaggtc                  39

<210> SEQ ID NO 72
<211> LENGTH: 59
<212> TYPE: DNA
<213> ORGANISM: Artificial Sequence
<220> FEATURE:
<223> OTHER INFORMATION: Primer
<220> FEATURE:
<221> NAME/KEY: dPO5-PO9iolC_fw_rev
<222> LOCATION: (1)..(59)
<223> OTHER INFORMATION: Primer

<400> SEQUENCE: 72
taagtttcgc tactcattcc ctaatgcaag tgataatcag atcaataaaa gccctggat      59

<210> SEQ ID NO 73
<211> LENGTH: 66
<212> TYPE: DNA
<213> ORGANISM: Artificial Sequence
<220> FEATURE:
<223> OTHER INFORMATION: Primer
<220> FEATURE:
<221> NAME/KEY: dPO5-PO9iolC_rev_fw
<222> LOCATION: (1)..(66)
<223> OTHER INFORMATION: Primer

<400> SEQUENCE: 73
ggaatgagta gcgaaactta gtgaaaaggg cagagtttgc aggtcatagt gcaactttgt     60
taaccc                                                               66

<210> SEQ ID NO 74
```

```
<211> LENGTH: 38
<212> TYPE: DNA
<213> ORGANISM: Artificial Sequence
<220> FEATURE:
<223> OTHER INFORMATION: Primer
<220> FEATURE:
<221> NAME/KEY: dPO5-PO9iolC_rev_rev
<222> LOCATION: (1)..(38)
<223> OTHER INFORMATION: Primer

<400> SEQUENCE: 74
ttgtaaaacg acggccagtg tccagctcag caagcagg                              38

<210> SEQ ID NO 75
<211> LENGTH: 25
<212> TYPE: DNA
<213> ORGANISM: Artificial Sequence
<220> FEATURE:
<223> OTHER INFORMATION: Primer
<220> FEATURE:
<221> NAME/KEY: dPO5-PO9iolC_check_fw
<222> LOCATION: (1)..(25)
<223> OTHER INFORMATION: Primer

<400> SEQUENCE: 75 gagttttct gcgatggcgg aactt                                             25

<210> SEQ ID NO 76
<211> LENGTH: 25
<212> TYPE: DNA
<213> ORGANISM: Artificial Sequence
<220> FEATURE:
<223> OTHER INFORMATION: Primer
<220> FEATURE:
<221> NAME/KEY: dPO5-PO9iolC_check_rev
<222> LOCATION: (1)..(25)
<223> OTHER INFORMATION: Primer

<400> SEQUENCE: 76
ggggtcttaa aagtctgatc ggtgg                                            25
```